US009458253B2

(12) United States Patent
Döring et al.

(10) Patent No.: US 9,458,253 B2
(45) Date of Patent: Oct. 4, 2016

(54) AMINO SILANE-MODIFIED POLYMERS

(75) Inventors: Christian Döring, Markranstädt (DE); Susanne Knoll, Leipzig (DE); Daniel Heidenreich, Schkopau (DE); Sven Thiele, Halle (DE)

(73) Assignee: TRINSEO EUROPE GMBH, Horgen (CH)

( * ) Notice: Subject to any disclaimer, the term of this patent is extended or adjusted under 35 U.S.C. 154(b) by 17 days.

(21) Appl. No.: 14/427,021

(22) PCT Filed: Sep. 14, 2012

(86) PCT No.: PCT/EP2012/068121
§ 371 (c)(1),
(2), (4) Date: Jul. 6, 2015

(87) PCT Pub. No.: WO2014/040640
PCT Pub. Date: Mar. 20, 2014

(65) Prior Publication Data
US 2016/0060368 A1    Mar. 3, 2016

(51) Int. Cl.
| | |
|---|---|
| *C08C 19/25* | (2006.01) |
| *C08C 19/20* | (2006.01) |
| *C08F 4/46* | (2006.01) |
| *C08F 4/60* | (2006.01) |
| *C08F 4/58* | (2006.01) |
| *C08C 19/44* | (2006.01) |
| *C08L 15/00* | (2006.01) |
| *C07F 7/08* | (2006.01) |
| *C07F 7/10* | (2006.01) |
| *C08L 9/06* | (2006.01) |
| *C08F 136/06* | (2006.01) |
| *C08F 136/08* | (2006.01) |

(52) U.S. Cl.
CPC ............ *C08C 19/25* (2013.01); *C07F 7/0801* (2013.01); *C07F 7/10* (2013.01); *C08C 19/20* (2013.01); *C08C 19/44* (2013.01); *C08F 4/46* (2013.01); *C08F 4/58* (2013.01); *C08F 4/6001* (2013.01); *C08L 9/06* (2013.01); *C08L 15/00* (2013.01); *C08F 136/06* (2013.01); *C08F 136/08* (2013.01)

(58) Field of Classification Search
None
See application file for complete search history.

(56) References Cited

U.S. PATENT DOCUMENTS

| | | |
|---|---|---|
| 3,078,254 A | 2/1963 | Zelinski et al. |
| 3,244,664 A | 4/1966 | Zelinski et al. |
| 3,281,383 A | 10/1966 | Zelinski et al. |
| 3,629,213 A | 12/1971 | Onishi et al. |
| 3,692,874 A | 9/1972 | Farrar et al. |
| 3,951,936 A | 4/1976 | Hanlon |
| 3,978,103 A | 8/1976 | Meyer-Simon et al. |
| 4,048,206 A | 9/1977 | Voronkov et al. |
| 4,474,908 A | 10/1984 | Wagner |
| 4,616,069 A | 10/1986 | Watanabe et al. |
| 4,689,368 A | 8/1987 | Jenkins |
| 4,931,376 A | 6/1990 | Ikematsu et al. |
| 5,086,136 A | 2/1992 | Takashima et al. |
| 5,089,574 A | 2/1992 | Castner |
| 5,134,199 A | 7/1992 | Hattori et al. |
| 5,448,002 A | 9/1995 | Castner |
| 5,753,579 A | 5/1998 | Jalics et al. |
| 5,753,761 A | 5/1998 | Sandstrom et al. |
| 5,834,573 A | 11/1998 | Castner |
| 6,018,007 A | 1/2000 | Lynch |
| 6,103,842 A | 8/2000 | Halasa et al. |
| 6,184,168 B1 | 2/2001 | Lynch |
| 6,229,036 B1 | 5/2001 | Batz-Sohn et al. |
| 6,310,152 B1 | 10/2001 | Castner |
| 6,489,415 B2 | 12/2002 | Hsu et al. |
| 6,617,406 B2 | 9/2003 | Castner |
| 6,627,715 B2 | 9/2003 | Halasa et al. |
| 6,693,160 B1 | 2/2004 | Halasa et al. |
| 6,777,569 B1 | 8/2004 | Westmeyer et al. |
| 6,984,687 B2 | 1/2006 | Henning et al. |
| 8,236,882 B2 | 8/2012 | Klockmann et al. |
| 2006/0241241 A1* | 10/2006 | Yan ............... C08C 19/44 524/588 |
| 2008/0287601 A1* | 11/2008 | Thiele ............ B60C 1/0016 524/588 |
| 2010/0056711 A1 | 3/2010 | Fujii et al. |
| 2010/0186869 A1* | 7/2010 | Sandstrom ........ B60C 1/00 152/564 |
| 2013/0165578 A1* | 6/2013 | Francik ........... C08C 19/20 524/516 |

FOREIGN PATENT DOCUMENTS

| | | |
|---|---|---|
| EP | 0964008 A1 | 12/1999 |
| EP | 0924214 B1 | 8/2002 |
| EP | 1367069 A1 | 12/2003 |
| JP | H11-301794 A | 11/1999 |
| JP | 2007-284572 A | 11/2007 |
| WO | WO 97/06192 | 2/1997 |
| WO | WO 2007/047943 A2 | 4/2007 |

(Continued)

OTHER PUBLICATIONS

International Search Report for PCT/EP2012/068121 dated Jul. 18, 2013, 4 pages.

(Continued)

*Primary Examiner* — Marc Zimmer
(74) *Attorney, Agent, or Firm* — Brinks Gilson & Lione; G. Peter Nichols

(57) ABSTRACT

Modified macromolecular compounds obtainable by using specific amino silane polymerization initiator compounds and optionally chain end-modifying compounds are described. Polymer compositions including such modified macromolecular compounds and the use of such compositions in the preparation of vulcanized (crosslinked) elastomeric polymer compositions and articles are described.

35 Claims, No Drawings

(56) References Cited

FOREIGN PATENT DOCUMENTS

| WO | WO 2008/156788 A2 | 12/2008 |
| WO | WO 2009/148932 A1 | 12/2009 |
| WO | WO 2011/031943 A1 | 3/2011 |
| WO | WO 2011/082277 A1 | 7/2011 |
| WO | WO 2012/091753 A1 | 7/2012 |

OTHER PUBLICATIONS

Written Opinion for PCT/EP2012/068121 dated Jul. 18, 2013, 6 pages.
International Preliminary Report on Patentability for PCT/EP2012/068121 dated Mar. 17, 2015, 7 pages.

* cited by examiner

AMINO SILANE-MODIFIED POLYMERS

This application claims priority to International Application No. PCT/EP2012/068121 filed Sep. 14, 2012 the entire contents of which are incorporated herein by reference.

FIELD OF THE INVENTION

This invention relates to modified macromolecular compounds obtainable by using specific amino silane polymerization initiator compounds and optionally chain end-modifying compounds. The invention also relates to elastomeric polymer compositions comprising such modified macromolecular compounds and the use of such compositions in the preparation of vulcanized (crosslinked) elastomeric polymer compositions and articles. The vulcanized elastomeric polymer compositions have relatively low hysteresis loss and are useful in many articles, including tire treads having low heat build up, low rolling resistance, good wet grip and ice grip, in combination with a good balance of other desirable physical and chemical properties, for example, abrasion resistance and tensile strength and excellent processability.

BACKGROUND OF THE INVENTION

It is generally accepted that increasing oil prices and national legislation requiring the reduction of automotive carbon dioxide emissions force tire and rubber producers to contribute to produce "fuel-efficient" and thus fuel- or gas-saving tires. One general approach to obtain fuel-efficient tires is to produce tire formulations which have reduced hysteresis loss. A major source of hysteresis in vulcanized elastomeric polymers is attributed to free polymer chain ends, i.e. the section of the elastomeric polymer chain between the last cross-link and the end of the polymer chain. This free end of the polymer does not participate in the efficient elastically recoverable process and, as a result, energy transmitted to this section of the polymer is lost. The dissipated energy leads to a pronounced hysteresis under dynamic deformation. Another source of hysteresis in vulcanized elastomeric polymers is attributed to an insufficient distribution of filler particles in the vulcanized elastomeric polymer composition. The hysteresis loss of a cross-linked elastomeric polymer composition is related to its tan δ value at 60° C. (see ISO 4664-1:2005; Rubber, Vulcanized or thermoplastic; Determination of dynamic properties—part 1: General guidance). In general, vulcanized elastomeric polymer compositions having relatively small tan δ values at 60° C. are preferred as having lower hysteresis loss. In the final tire product, this translates into a lower rolling resistance and better fuel economy.

It is generally accepted that a lower rolling resistance tire can be made at the expense of deteriorated wet grip properties. For example, if, in a random solution styrene-butadiene rubber (random SSBR), the polystyrene unit concentration is relatively reduced with respect to the total polybutadiene unit concentration, and the 1,2-polydiene unit concentration is kept constant, the SSBR glass transition temperature is reduced and, as consequence, both tan δ at 60° C. and tan δ at 0° C. are reduced, generally corresponding to improved rolling resistance and deteriorated wet grip performance of the tire. Similarly, if, in a random solution styrene-butadiene rubber (random SSBR), the 1,2-polybutadiene unit concentration is relatively reduced with respect to the total polybutadiene unit concentration, and the polystyrene unit concentration is kept constant, the SSBR glass transition temperature is reduced and, as consequence, both tan δ at 60° C. and tan δ at 0° C. are reduced, generally corresponding to improved rolling resistance and deteriorated wet grip performance of the tire. Accordingly, when assessing the rubber vulcanizate performance correctly, both the rolling resistance, related to tan δ at 60° C., and the wet grip, related to tan δ at 0° C., should be monitored along with the tire heat build up.

One generally accepted approach to reducing hysteresis loss is to reduce the number of free chain ends of elastomeric polymers. Various techniques have been described in the literature, including the use of "coupling agents," such as tin tetrachloride, which may functionalize the polymer chain end and react with components of an elastomeric composition, for example with a filler or with unsaturated portions of a polymer. Examples of such techniques and coupling agents are described in the following patents: U.S. Pat. Nos. 3,281,383 3,244,664 and 3,692,874 (for example, tetrachlorosilane); U.S. Pat. Nos. 3,978,103; 4,048,206; 4,474,908; 6,777,569 (blocked mercaptosilanes) and U.S. Pat. No. 3,078,254 (a multi-halogen-substituted hydrocarbon, such as 1,3,5-tri(bromo methyl)benzene); U.S. Pat. No. 4,616,069 (tin compound and organic amino or amine compound); and U.S. 2005/0124740.

The use of "coupling agents" as reactants with living polymers more often than not leads to the formation of polymer blends comprising one fraction of linear or uncoupled polymers and one or more fractions comprising more than two polymer arms at the coupling point. The reference article "Synthesis of end-functionalized polymer by means of living anionic polymerization," Journal of Macromolecular Chemistry and Physics, 197, (1996), 3135-3148, describes the synthesis of "polystyrene-containing" and "polyisoprene-containing" living polymers with hydroxy (—OH) and mercapto (—SH) functional end caps, obtained by reaction of the living polymers with haloalkanes containing silyl ether and silyl thioether functions. The tertiary-butyldimethylsilyl (TBDMS) group is preferred as a protecting group for the —OH and —SH functions in the termination reactions, because the corresponding silyl ethers and thioethers are found to be both stable and compatible with anionic living polymers.

WO2007/047943 describes the use of a silane-sulfide omega chain end modifier to produce a chain end-modified elastomeric polymer, used as component in a vulcanized elastomeric polymer composition or a tire tread. Although cured rubber hysteresis properties can be improved significantly, the effect is limited since only one polymer chain end can be functionalized by using the modifier compound described.

WO9706192 describes a copolymer produced by copolymerizing an alkenyl-substituted aromatic hydrocarbon and a conjugated diene with a protected functional organometallic initiator. WO9706192 does not provide cured polymer or copolymers, so that the impact of the moiety derived from the organometallic initiator in the (co)polymer on cured rubber hysteresis properties is not known.

WO2011031943 describes a polymerization initiator comprising at least two protected primary amine groups and at least one alkali or alkaline earth metal, as well as the polymers made by using the specified polymerization initiators.

WO2011082277 reports on a "metallated aminosilane compound for initiating an anionic polymerization" comprising the reaction product of (1) at least one metallating agent and (2) at least one specific alkylaminosilane compound. While the components (1) and (2) are described in detail, hardly any structural information is given with respect to the "metallated aminosilane compound for initiating an anionic polymerization", and none is given for the polymer structure element derived from the initiator system used.

There is a need for modification methods and resulting modified macromolecular compounds that can be used to further optimize dynamic silica and carbon black vulcanizate properties, including low hysteresis properties, corresponding to a high wet grip and low rolling resistance property in tires. In addition, there is a need to further decrease the vulcanizate heat built up during thermal exposure and under mechanical stress. These needs have been met by the following invention. Particularly, there is a need for an efficient organometal initiator which improves cured modified polymer hysteresis properties when used either alone or in combination with chain end modifiers, the combined embodiment leading to significantly enhanced performance property improvements.

SUMMARY OF THE INVENTION

The present invention provides a modified macromolecular compound (also referred to as a modified elastomeric macromolecular compound) of the following Formula A:

$$\left[ HO-\underset{R^4}{\overset{R^3}{\underset{|}{Si}}}-\underset{R^6}{\overset{R^5}{\underset{|}{C}}}-P \right]_p -K \quad \text{Formula A}$$

wherein
$R^3$ and $R^4$ are each independently selected from —OH, $(C_1\text{-}C_{18})$ alkyl, $(C_6\text{-}C_{18})$ aryl and $(C_7\text{-}C_{18})$ aralkyl;
$R^5$ and $R^6$ are each independently selected from hydrogen, $(C_1\text{-}C_{18})$ alkyl, $(C_6\text{-}C_{18})$ aryl and $(C_7\text{-}C_{18})$ aralkyl;
P is an elastomeric diene polymer chain comprising monomer units derived from at least one of the following monomers: butadiene, isoprene, styrene and alpha-methylstyrene; and
K represents a hydrogen atom or $$-\underset{(OR^1)_m}{\overset{(R^2)_n}{\underset{|}{Si}}}-Y-S-Z$$

wherein
$R^1$ is independently selected from a hydrogen atom and $(C_1\text{-}C_4)$ alkyl;
$R^2$ is independently selected from $(C_1\text{-}C_{18})$ alkyl;
Y is at least divalent and is $(C_1\text{-}C_{18})$ alkyl, which may be substituted with one or more of the following groups: tertiary amine group, silyl group, $(C_7\text{-}C_{18})$ aralkyl group and $(C_6\text{-}C_{18})$ aryl group; and
Z represents hydrogen or $$-\underset{R^8}{\overset{R^7}{\underset{|}{M^1}}}-T$$

wherein
$M^1$ is a silicon atom or a tin atom; $R^7$ and $R^8$ are independently selected from $(C_1\text{-}C_{18})$ alkyl, $(C_6\text{-}C_{18})$ aryl and $(C_7\text{-}C_{18})$ aralkyl; and T represents $R^{11}$ or $$-S-Y-\underset{(OR^{10})_u}{\overset{(R^9)_t}{\underset{|}{Si}}}-(D)_o$$

wherein
Y is as defined above;
$R^9$ is independently selected from $(C_1\text{-}C_{18})$ alkyl;
$R^{10}$ is independently selected from a hydrogen atom and $(C_1\text{-}C_4)$ alkyl;
$R^{11}$ is selected from $(C_1\text{-}C_{18})$ alkyl, $(C_6\text{-}C_{18})$ aryl and $(C_7\text{-}C_{18})$ aralkyl; and
D represents $OR^1$ or $$-P-\underset{R^6}{\overset{R^5}{\underset{|}{C}}}-\underset{R^4}{\overset{R^3}{\underset{|}{Si}}}-OH$$

wherein
$R^1$, P, $R^3$, $R^4$, $R^5$ and $R^6$ are as defined above; and
p and o are each independently selected from an integer of 1, 2 and 3; m, n, t and u are each independently selected from an integer of 0, 1 and 2; and wherein p is 1 if K is H and otherwise p+m+n=3 and t+u+o=3.

The invention further provides a method of making the modified macromolecular compound of Formula A, comprising the steps of
(i) polymerizing in solution at least one elastomeric diene monomer with at least one amino silane polymerization initiator compound of Formula 4 or Formula 5

Formula 4

Formula 5 or Lewis base adducts thereof, wherein
$R^{3a}$ is independently selected from —N($R^{28}$)$R^{29}$, ($C_1$-$C_{18}$) alkyl, ($C_6$-$C_{18}$) aryl and ($C_7$-$C_{18}$) aralkyl;
$R^{4a}$ is independently selected from —N($R^{30}$)$R^{31}$, ($C_1$-$C_{18}$) alkyl, ($C_6$-$C_{18}$) aryl and ($C_7$-$C_{18}$) aralkyl;
$R^5$ and $R^6$ are as defined above;
$M^2$ is lithium, sodium or potassium;
$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ are each independently selected from hydrogen, ($C_1$-$C_{18}$) alkyl, ($C_6$-$C_{18}$) aryl and ($C_7$-$C_{18}$) aralkyl;
$R^{26}$, $R^{27}$, $R^{28}$, $R^{29}$, $R^{30}$ and $R^{31}$ are each independently selected from ($C_1$-$C_{18}$) alkyl, ($C_6$-$C_{18}$) aryl and ($C_7$-$C_{18}$) aralkyl;
q is selected from an integer of 1, 2, 3, 4 and 5; and
r is selected from an integer of 1, 2 and 3;
(ii) optionally reacting the polymer resulting from step (i) in solution with a chain end-modifying compound of Formula 6

Formula 6

$$\begin{array}{c} (R^2)_n \quad\quad R^7 \\ | \quad\quad\quad | \\ Si-Y-S-M^1-T \\ | \quad\quad\quad | \\ (OR^{1a})_s \quad R^8 \end{array}$$

wherein
$M^1$, Y, $R^2$, $R^7$, $R^8$ and n are as defined above;
$R^{1a}$ is independently selected from ($C_1$-$C_4$) alkyl;
s is an integer of 1, 2 or 3; and n+s=3;
T represents $R^{11}$ or $$\begin{array}{c} (R^9)_t \\ | \\ -S-Y-Si \\ | \\ (OR^{10a})_v \end{array}$$

wherein
Y, $R^9$, $R^{11}$ and t are as defined above;
$R^{10a}$ is independently selected from ($C_1$-$C_4$) alkyl;
v is an integer of 1, 2 or 3; and t+v=3; and
(iii) optionally contacting the polymer resulting from step (i) or (ii) with a protonating agent.

In accordance with the invention, the amino silane polymerization initiator compound of Formula 4 or Formula 5, which constitutes another aspect of the invention, can be obtained in a step (ia) by reacting
a compound of Formula 9

Formula 9

$$\begin{array}{c} R^{26} \quad R^{3a} \quad R^5 \\ \phantom{R^{26}}\backslash \quad | \quad\quad | \\ N-Si-C-X \\ / \quad | \quad\quad | \\ R^{27} \quad R^{4a} \quad R^6 \end{array}$$

wherein
X is a chlorine atom, a bromine atom or a iodine atom; and
$R^{3a}$, $R^{4a}$, $R^5$, $R^6$, $R^{26}$ and $R^{27}$ are as defined above;
an alkali metal selected from lithium, sodium and potassium; and
a compound selected from Formula 10 and Formula 11

Formula 10

$$\begin{array}{c} R^{12} \quad\quad\quad R^{18} \quad\quad\quad R^{15} \\ \phantom{R^{12}} O \phantom{xx} \phantom{[} \phantom{xx} O \phantom{]} \phantom{xx} \\ \phantom{xx} \diagup\phantom{x}\diagdown\phantom{x} [ \phantom{x} C \phantom{x} ]_q \phantom{x} \diagup\phantom{x}\diagdown \\ R^{13} \quad\quad R^{14} \quad R^{19} \quad R^{17} \quad R^{16} \end{array}$$

Formula 11

$$\begin{array}{c} R^{22} \backslash \phantom{x} N \phantom{x} \quad [ R^{20} \quad ] \quad N \phantom{x} / R^{25} \\ \phantom{x} / \phantom{xxx} \backslash \phantom{x} C \phantom{x} / \phantom{xxx} \backslash R^{24} \\ R^{23} \quad\quad [ \phantom{x} R^{21} \phantom{x} ]_r \end{array}$$

wherein
$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$, q and r are as defined above.

The modified macromolecular compound of Formula A of the present invention is usually obtained in the form of a polymer composition comprising at least one modified macromolecular compound of Formula A and one or more further components selected from components which (i) are added to or formed as a result of the polymerization process used for making the modified macromolecular compound and components which (ii) remain after solvent removal ("first polymer composition"). Such components include, but are not limited to, for example, stabilizer compounds, further modified or non-modified polymers, processing aids, softeners and anti-stickiness agents.

The modified macromolecular compound of Formula A of the present invention can furthermore be provided in the form of a polymer composition comprising at least one modified macromolecular compound of Formula A, for example in the form of the first polymer composition, and at least one filler ("second polymer composition").

The invention also provides a vulcanized polymer composition comprising the reaction product of at least the following:
1) at least one vulcanization agent; and
2) the first or second polymer composition as described herein.

The invention also provides a method for making a vulcanized polymer composition comprising reacting at least the following components:
1) at least one vulcanization agent; and
2) the first or second polymer composition as described herein.

DETAILED DESCRIPTION OF THE INVENTION

The present invention provides a modified macromolecular compound of Formula A as generally defined above.

In a preferred embodiment, the modified macromolecular compound has the following Formula 1:

Formula 1

$$\left[ HO-\underset{\underset{R^4}{|}}{\overset{\overset{R^3}{|}}{Si}}-\underset{\underset{R^6}{|}}{\overset{\overset{R^5}{|}}{C}}-P \right]_p \underset{\underset{(OR^1)_m}{|}}{\overset{\overset{(R^2)_n}{|}}{Si}}-Y-S-Z$$

wherein $R^1$, $R^2$, $R^3$, $R^4$, $R^5$, $R^6$, Y, P and Z; and n, m and p are as generally defined above.

In one preferred embodiment, Y is divalent and is ($C_1$-$C_{18}$) alkyl.

In one preferred embodiment, $R^5$ and $R^6$ are each independently selected from hydrogen and ($C_1$-$C_{18}$) alkyl and $R^7$ and $R^8$ are each independently selected from ($C_1$-$C_{18}$) alkyl and $R^3$ and $R^4$ are each independently selected from —OH and ($C_1$-$C_{18}$) alkyl.

In one preferred embodiment, $R^3$, $R^4$, $R^7$ and $R^8$ are each independently selected from ($C_1$-$C_{18}$) alkyl and $R^5$ and $R^6$ are each independently selected from hydrogen and ($C_1$-$C_{18}$) alkyl.

In one preferred embodiment, p and o are each independently selected from an integer of 1 and 2; m and u are each independently selected from an integer of 1 and 2; n and t are each independently selected from an integer of 0 and 1.

In one embodiment, referred to as "Embodiment 1", the modified macromolecular compound is represented by Formula 1 as generally defined above, wherein $R^1$, $R^2$, $R^4$, $R^5$, $R^6$, Y, P and n, m and p are as generally defined above; $R^3$ is selected from —OH and ($C_1$-$C_{18}$) alkyl; Z is represented by -$M^1(R^7)(R^8)$(T); $M^1$ is a silicon atom or a tin atom; $R^7$ and $R^8$ are each independently selected from ($C_1$-$C_{18}$) alkyl; and T represents

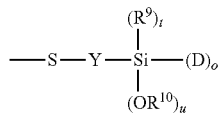

wherein Y, $R^9$, $R^{10}$ and D, and t, u und o are as generally defined above.

In one preferred embodiment, Y is divalent and is ($C_1$-$C_{18}$) alkyl.

In one preferred embodiment, $R^5$ and $R^6$ are each independently selected from hydrogen and ($C_1$-$C_{18}$) alkyl and; $R^3$ and $R^4$ are each independently selected from —OH and ($C_1$-$C_{18}$) alkyl.

In one preferred embodiment, $R^3$ and $R^4$ are each independently selected from ($C_1$-$C_{18}$) alkyl and $R^5$ and $R^6$ are each independently selected from hydrogen and ($C_1$-$C_{18}$) alkyl.

In one preferred embodiment, p and o are each independently selected from an integer of 1 and 2; m and u are each independently selected from an integer of 2 and 3; and n and t are each independently selected from an integer of 0 and 1.

In another embodiment, referred to as "Embodiment 2", the modified macromolecular compound is represented by Formula 1 as generally defined above, wherein $R^1$, $R^2$, $R^4$, $R^5$, $R^6$, Y, P and n, m and p are as generally defined above; $R^3$ is selected from —OH and ($C_1$-$C_{18}$) alkyl; Z is represented by -$M^1(R^7)(R^8)$(T); $M^1$ is a silicon atom or a tin atom; $R^7$ and $R^8$ are each independently selected from ($C_1$-$C_{18}$) alkyl; and T is represented by $R^{11}$, wherein $R^{11}$ is selected from ($C_1$-$C_{18}$) alkyl.

In one preferred embodiment, Y is divalent and is ($C_1$-$C_{18}$) alkyl.

In one preferred embodiment, $R^5$ and $R^6$ are each independently selected from hydrogen and ($C_1$-$C_{18}$) alkyl and $R^3$ and $R^4$ are each independently selected from —OH and ($C_1$-$C_{18}$) alkyl.

In one preferred embodiment, $R^3$ and $R^4$ are each independently selected from ($C_1$-$C_{18}$) alkyl and $R^5$ and $R^6$ are each independently selected from hydrogen and ($C_1$-$C_{18}$) alkyl.

In one preferred embodiment, p is selected from an integer of 1 and 2; m is selected from an integer of 2 and 3; and n is each an integer of 0 or 1.

The invention further provides a method of making the modified macromolecular compound of Formula A, comprising the step (i) and optionally one or both of steps (ii) and (iii) as generally defined above.

In one embodiment, step (ii) is an essential step, and Formula A takes the form of Formula 1.

In one preferred embodiment, $M^2$ is lithium.

In one preferred embodiment, $R^{3a}$ is selected from —N($R^{28}$)$R^{29}$ and ($C_1$-$C_{18}$) alkyl, wherein $R^{28}$ and $R^{29}$ are as generally defined above.

In one preferred embodiment, $R^{3a}$, $R^{4a}$, $R^{22}$, $R^{23}$, $R^{24}$, $R^{25}$, $R^{26}$ and $R^{27}$ are each independently selected from ($C_1$-$C_{18}$) alkyl and $R^5$, $R^6$, $R^{18}$, $R^{19}$, $R^{20}$ and $R^{21}$ are each independently selected from hydrogen and ($C_1$-$C_{18}$) alkyl and $R^{12}$, $R^{13}$, $R^{14}$, $R^{15}$, $R^{16}$ and $R^{17}$ are each independently selected from hydrogen and ($C_1$-$C_6$) alkyl.

In one preferred embodiment, Y is divalent and is ($C_1$-$C_{18}$) alkyl.

In one preferred embodiment, q is 1 and r is 2.

In one preferred embodiment, s and v are each independently selected from an integer of 2 and 3; and n and t are each independently selected from an integer of 0 and 1.

In one preferred embodiment, the invention provides a method of making the modified macromolecular compound of Formula 1, defined according to Embodiment 1, comprising the steps (i) and (ii) and optionally step (iii) as generally defined above, wherein the chain end-modifying compound of Formula 6 has the following Formula 7

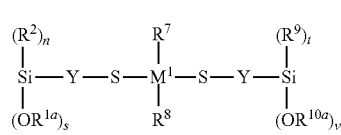

Formula 7 wherein
$M^1$, Y, $R^{1a}$, $R^2$, n and s are as generally defined for Formula 6;
$R^7$, $R^8$ and $R^9$ are each independently selected from ($C_1$-$C_{18}$) alkyl;
$R^{10a}$ is independently selected from ($C_1$-$C_4$) alkyl;
t is selected from an integer of 0, 1 and 2; v is selected from an integer of 1, 2 and 3; and t+v=3.

In one preferred embodiment, $M^2$ is lithium.

In one preferred embodiment, $R^{3a}$ is selected from —N($R^{28}$)$R^{29}$ and ($C_1$-$C_{18}$) alkyl, wherein $R^{28}$ and $R^{29}$ are as generally defined above.

In one preferred embodiment, $R^{3a}$, $R^{4a}$, $R^{22}$, $R^{23}$, $R^{24}$, $R^{25}$, $R^{26}$ and $R^{27}$ are each independently selected from ($C_1$-$C_{18}$) alkyl and $R^5$, $R^6$, $R^{18}$, $R^{19}$, $R^{20}$ and $R^{21}$ are each independently selected from hydrogen and ($C_1$-$C_{18}$) alkyl and $R^{12}$, $R^{13}$, $R^{14}$, $R^{15}$, $R^{16}$ and $R^{17}$ are each independently selected from hydrogen and ($C_1$-$C_6$) alkyl.

In one preferred embodiment, Y is divalent and is ($C_1$-$C_{18}$) alkyl.

In one preferred embodiment, q is 1 and r is 2.

In one preferred embodiment, s and v are each independently selected from an integer of 2 and 3; and n and t are each independently selected from an integer of 0 and 1.

In another preferred embodiment, the invention provides a method of making the modified macromolecular compound of Formula 1, defined according to Embodiment 2, comprising the steps (i) and (ii) and optionally step (iii) as generally defined above, wherein the chain end-modifying compound of Formula 6 has the following Formula 8

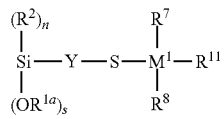

Formula 8 wherein $M^1$, Y, $R^{1a}$, $R^2$, n and s are as generally defined for Formula 6; $R^7$ and $R^8$ are each independently selected from ($C_1$-$C_{18}$) alkyl; and $R^{11}$ is selected from ($C_1$-$C_{18}$) alkyl; ($C_7$-$C_{18}$) aralkyl and ($C_6$-$C_{18}$) aryl.

In one preferred embodiment, $M^2$ is lithium.

In one preferred embodiment, $R^{3a}$ is selected from —N($R^{28}$)$R^{29}$ and ($C_1$-$C_{18}$) alkyl.

In one preferred embodiment, $R^{3a}$, $R^{4a}$, $R^{22}$, $R^{23}$, $R^{24}$, $R^{25}$, $R^{26}$ and $R^{27}$ are each independently selected from ($C_1$-$C_{18}$) alkyl and $R^5$, $R^6$, $R^{18}$, $R^{19}$, $R^{20}$ and $R^{21}$ are each independently selected from hydrogen and ($C_1$-$C_{18}$) alkyl and $R^{12}$, $R^{13}$, $R^{14}$, $R^{15}$; $R^{16}$ and $R^{17}$ are each independently selected from hydrogen and ($C_1$-$C_6$) alkyl.

In one preferred embodiment, Y is divalent and is ($C_1$-$C_{18}$) alkyl.

In one preferred embodiment, q is 1 and r is 2.

In one preferred embodiment, s is selected from an integer of 2 and 3; and n is selected from an integer of 0 and 1.

In accordance with a particularly preferred aspect of the invention, the amino silane polymerization initiator compound of Formula 4 or Formula 5 used in step (i) of the above-described methods is obtained in a step (ia) by reacting a compound of Formula 9 as generally defined above, an alkali metal selected from lithium, sodium and potassium, and a compound of Formula 10 or Formula 11, respectively, as generally defined above.

In one preferred embodiment, $M^2$ is lithium.

In one preferred embodiment, $R^3$, $R^4$, $R^{22}$, $R^{23}$, $R^{24}$, $R^{25}$, $R^{26}$ and $R^{27}$ are each independently selected from ($C_1$-$C_{18}$) alkyl and $R^5$, $R^6$, $R^{18}$, $R^{19}$, $R^{20}$ and $R^{21}$ are each independently selected from hydrogen and ($C_1$-$C_{18}$) alkyl and $R^{12}$, $R^{13}$, $R^{14}$, $R^{15}$, $R^{16}$ and $R^{17}$ are each independently selected from hydrogen and ($C_1$-$C_6$) alkyl.

In one preferred embodiment, the alkali metal in step (ia) is lithium.

In one preferred embodiment, Y is divalent and is ($C_1$-$C_{18}$) alkyl.

In one preferred embodiment, q is 1 and r is 2.

In one preferred embodiment, s and v are each independently selected from an integer of 2 and 3; and n and t are each independently selected from an integer of 0 and 1.

The amino silane polymerization initiator compounds of Formula 4 and Formula 5, as defined above generally and in preferred embodiments, constitute additional aspects of the present invention.

In one preferred embodiment, the invention more preferably provides a method of making the modified macromolecular compound of Formula 1, defined according to Embodiment 1, comprising the steps (ia), (i) and (ii) and optionally step (iii) as generally defined above, wherein a compound of Formula 7 as defined above is used as the chain end-modifying compound.

In one preferred embodiment, $M^2$ is lithium.

In one preferred embodiment, $R^3$, $R^4$, $R^{22}$, $R^{23}$, $R^{24}$, $R^{25}$, $R^{26}$ and $R^{27}$ are each independently selected from ($C_1$-$C_{18}$) alkyl and $R^5$, $R^6$, $R^{18}$, $R^{19}$, $R^{20}$ and $R^{21}$ are each independently selected from hydrogen and ($C_1$-$C_{18}$) alkyl and $R^{12}$, $R^{13}$, $R^{14}$, $R^{15}$; $R^{16}$ and $R^{17}$ are each independently selected from hydrogen and ($C_1$-$C_6$) alkyl.

In one preferred embodiment, the alkali metal in step (ia) is lithium.

In one preferred embodiment, Y is divalent and is ($C_1$-$C_{18}$) alkyl.

In one preferred embodiment, q is 1 and r is 2.

In one preferred embodiment, s and v are each independently selected from an integer of 2 and 3; and n and t are each independently selected from an integer of 0 and 1.

In another preferred embodiment, the invention more preferably provides a method of making the modified macromolecular compound of Formula 1, defined according to Embodiment 2, comprising the steps (ia), (i) and (ii) and optionally step (iii) as generally defined above, wherein a compound of Formula 8 as defined above is used as the chain end-modifying compound.

In one preferred embodiment, $M^2$ is lithium.

In one preferred embodiment, $R^3$, $R^4$, $R^{22}$, $R^{23}$, $R^{24}$, $R^{25}$, $R^{26}$ and $R^{27}$ are each independently selected from ($C_1$-$C_{18}$) alkyl and $R^5$, $R^6$, $R^{18}$, $R^{19}$, $R^{20}$ and $R^{21}$ are each independently selected from hydrogen and ($C_1$-$C_{18}$) alkyl and $R^{12}$, $R^{13}$, $R^{14}$, $R^{15}$, $R^{16}$ and $R^{17}$ are each independently selected from hydrogen and ($C_1$-$C_6$) alkyl.

In one preferred embodiment, the alkali metal in step (ia) is lithium.

In one preferred embodiment, Y is divalent and is ($C_1$-$C_{18}$) alkyl.

In one preferred embodiment, q is 1 and r is 2.

In one preferred embodiment, s is selected from an integer of 2 and 3; and n is selected from an integer of 0 and 1.

The invention further provides a polymer composition comprising at least one modified macromolecular compound of Formula A, preferably of Formula 1, as defined above generally and in preferred embodiments ("first polymer composition"). In one embodiment, the modified macromolecular compound is defined according to Embodiment 1. In another embodiment, the modified macromolecular compound is defined according to Embodiment 2.

In another embodiment, the first polymer composition constitutes the product obtained from the method for making the modified macromolecular compound of Formula A, preferably of Formula 1, after removal of reaction solvent. In one embodiment, the polymer composition further comprises an oil which is not the reaction solvent.

In one embodiment, the first polymer composition can constitute the solvent-free result of a polymer manufacturing process. In such case, the polymer composition comprises the at least one modified macromolecular compound of Formula A, preferably of Formula 1, as defined above generally and in preferred embodiments, and typically components which (i) are added to or formed as a result of the polymerization process used for making the modified macromolecular compound prior to solvent removal, and which (ii) remain in the formed polymer composition after solvent removal. For example, the specified components may, but do not have to include, and are not limited to, for example, one or more selected from stabilizer compounds, alternative modified or non-modified polymers, processing aids, softeners and anti-stickiness agents.

In one embodiment, the polymer composition of the present invention comprises the at least one modified macromolecular compound of Formula A, preferably of Formula 1, as defined above generally and in preferred embodiments, and at least one filler ("second polymer composition").

In one preferred embodiment, the at least one filler comprises silica.

In one preferred embodiment, the at least one filler comprises carbon black.

In one embodiment, the second polymer composition further comprises an oil.

In one further embodiment, the second polymer composition comprises a vulcanization agent.

In one embodiment, the second polymer composition is the result of a mechanical mixing process involving the first polymer composition and at least one filler. The second polymer composition typically includes components which are added to the (solvent-free) first polymer composition and which remain in the composition after completion of the mechanical mixing process. Therefore, the specified components comprised in the second polymer composition include at least one filler and may, but do not have to include, and are not limited to alternative (solvent-free) modified or non-modified polymers, stabilizers and softeners.

The invention also provides a vulcanized polymer composition comprising the reaction product of at least the following:
1) at least one vulcanization agent; and
2) the first polymer composition or second polymer composition as described herein.

In one preferred embodiment of the vulcanized polymer composition, component 2) is the second polymer composition as described herein.

The vulcanized polymer composition is understood to mean the result of a reactive polymer-polymer crosslink forming process which is performed on the first or second polymer composition comprising at least one vulcanization agent. The reactive process converts an essentially uncrosslinked elastomeric polymer composition into a crosslinked elastomeric polymer composition, here referred to as a vulcanized polymer composition.

The invention also provides a method for making a vulcanized polymer composition comprising reacting at least the following components:
1) at least one vulcanization agent; and
2) the first polymer composition or second polymer composition as described herein.

In one preferred embodiment of the method for making the vulcanized polymer composition, component 2) is the second polymer composition as described herein.

In the polymer compositions and vulcanized polymer compositions of the present invention, two or more different modified macromolecular compounds of the invention may be used.

The present invention also provides an article comprising at least one component formed from a vulcanized polymer composition in accordance with the present invention. In one embodiment, the article is a tire or tire tread.

The following embodiments apply to all applicable aspects and embodiments described herein.

In general, the elastomeric diene polymer chain of the modified macromolecular compound may be selected from the group consisting of modified styrene-butadiene copolymers, modified polybutadiene, modified butadiene-isoprene copolymers, modified polyisoprene and modified butadiene-styrene-isoprene terpolymers.

Polymer compositions and vulcanized polymer composition in accordance with the present invention may further comprise at least one polymer selected from the group consisting of styrene-butadiene copolymers, including but not limited to solution styrene-butadiene rubber (SSBR) and emulsion styrene-butadiene rubber (ESBR); polybutadiene, including polybutadiene with a 1,4-cis-polybutadiene concentration ranging from 90 to 99 percent, from 30 to 70 percent, or from 2 to 25 percent, based on weight; butadiene-isoprene copolymers; polyisoprene; butadiene-styrene-isoprene terpolymers; and combinations thereof.

Amino Silane Polymerization Initiator Compounds

The amino silane polymerization initiator compounds of Formula 4 and Formula 5 of the present invention include within their scope the following compounds represented by Formula 4a, Formula 4b, Formula 4c, Formula 5a, Formula 5b and Formula 5c:

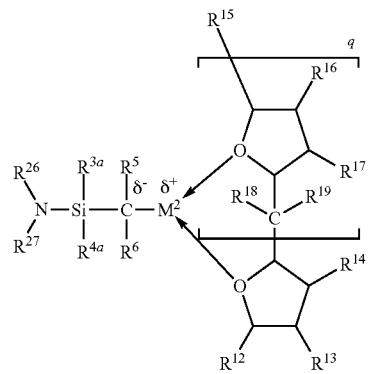

Formula 4a

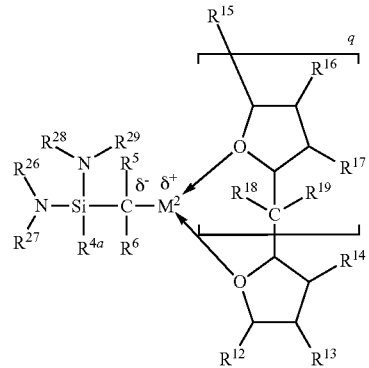

Formula 4b

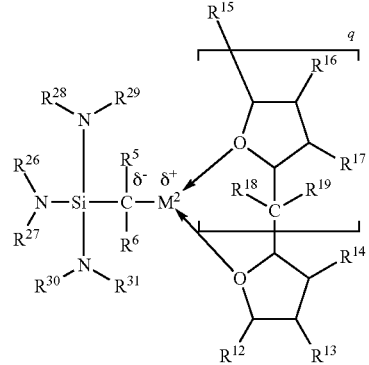

Formula 4c

-continued

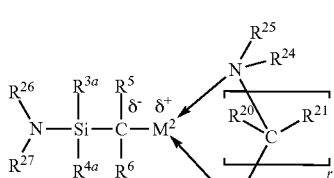

Formula 5a

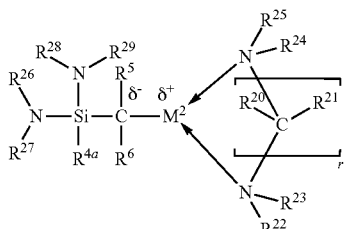

Formula 5b

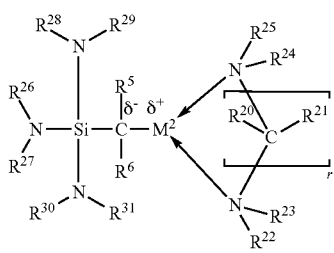

Formula 5c and Lewis base adducts thereof,
wherein
$M^2$ is lithium, sodium or potassium;
$R^5$, $R^6$, $R^{12}$, $R^{13}$, $R^{14}$, $R^{15}$, $R^{16}$, $R^{17}$, $R^{18}$, $R^{19}$, $R^{20}$ and $R^{21}$ are each independently selected from hydrogen, $(C_1\text{-}C_8)$ alkyl, $(C_6\text{-}C_{18})$ aryl and $(C_7\text{-}C_{18})$ aralkyl;
$R^{3a}$, $R^{4a}$, $R^{22}$, $R^{23}$, $R^{24}$, $R^{25}$, $R^{26}$, $R^{27}$, $R^{28}$, $R^{29}$, $R^{30}$ and $R^{31}$ are each independently selected from $(C_1\text{-}C_{18})$ alkyl, $(C_6\text{-}C_{18})$ aryl and $(C_7\text{-}C_{18})$ aralkyl;
r is selected from an integer of 1, 2 and 3; q is selected from an integer of 1, 2, 3, 4 and 5.

In one embodiment, the amino silane polymerization initiator compound comprises one tertiary amine group and is represented by Formula 4a, or Lewis base adducts thereof, wherein $M^2$ is lithium; $R^{3a}$, $R^{4a}$, $R^{26}$ and $R^{27}$ are each independently selected from $(C_1\text{-}C_{18})$ alkyl; $R^5$, $R^6$, $R^{18}$ and $R^{19}$ are each independently selected from hydrogen and $(C_1\text{-}C_{18})$ alkyl; and $R^{12}$, $R^{13}$, $R^{14}$, $R^{15}$, $R^{16}$ and $R^{17}$ are each independently selected from hydrogen and $(C_1\text{-}C_6)$ alkyl; and q is 1.

In one embodiment, the amino silane polymerization initiator compound comprises two tertiary amine groups and is represented by Formula 4b, or Lewis base adducts thereof, wherein $M^2$ is lithium; $R^{4a}$, $R^{26}$, $R^{27}$, $R^{28}$ and $R^{29}$ are each independently selected from $(C_1\text{-}C_{18})$ alkyl; $R^5$, $R^6$, $R^{18}$ and $R^{19}$ are each independently selected from hydrogen and $(C_1\text{-}C_{18})$ alkyl; and $R^{12}$, $R^{13}$, $R^{14}$, $R^{15}$, $R^{16}$ and $R^{17}$ are each independently selected from hydrogen and $(C_1\text{-}C_6)$ alkyl; and q is 1.

In one embodiment, the amino silane polymerization initiator compound comprises three tertiary amine groups and is represented by Formula 4c, or Lewis base adducts thereof, wherein $M^2$ is lithium; $R^{26}$, $R^{27}$, $R^{28}$, $R^{29}$, $R^{30}$ and $R^{31}$ are each independently selected from $(C_1\text{-}C_{18})$ alkyl; $R^5$, $R^6$, $R^{18}$ and $R^{19}$ are each independently selected from hydrogen and $(C_1\text{-}C_{18})$ alkyl; and $R^{12}$, $R^{13}$, $R^{14}$, $R^{15}$, $R^{16}$ and $R^{17}$ are each independently selected from hydrogen and $(C_1\text{-}C_6)$ alkyl; and q is 1.

In one embodiment, the amino silane polymerization initiator compound comprises one covalently single bound tertiary amine group and two coordinatively bound secondary amine groups and is represented by Formula 5a, or Lewis base adducts thereof, wherein $M^2$ is lithium; $R^5$, $R^6$, $R^{20}$ and $R^{21}$ are each independently selected from hydrogen and $(C_1\text{-}C_{18})$ alkyl; $R^{3a}$, $R^{4a}$, $R^{22}$, $R^{23}$, $R^{24}$, $R^{25}$, $R^{26}$ and $R^{27}$ are each independently selected from $(C_1\text{-}C_{18})$ alkyl; and r is 2.

In one embodiment, the amino silane polymerization initiator compound comprises two covalently single bound tertiary amine groups and two coordinatively bound secondary amine groups and is represented by Formula 5b, or Lewis base adducts thereof, wherein $M^2$ is lithium; $R^5$, $R^6$, $R^{20}$ and $R^{21}$ are each independently selected from hydrogen and $(C_1\text{-}C_{18})$ alkyl; $R^{4a}$, $R^{22}$, $R^{23}$, $R^{24}$, $R^{25}$, $R^{26}$, $R^{27}$, $R^{28}$ and $R^{29}$ are each independently selected from $(C_1\text{-}C_{18})$ alkyl; and r is 2.

In one embodiment, the amino silane polymerization initiator compound comprises three covalently single bound tertiary amine groups and two coordinatively bound secondary amine groups and is represented by Formula 5c, or Lewis base adducts thereof, wherein $M^2$ is lithium; $R^5$, $R^6$, $R^{20}$ and $R^{21}$ are each independently selected from hydrogen and $(C_1\text{-}C_{18})$ alkyl; $R^{22}$, $R^{23}$, $R^{24}$, $R^{25}$, $R^{26}$, $R^{27}$, $R^{28}$, $R^{29}$, $R^{30}$ and $R^{31}$ are each independently selected from $(C_1\text{-}C_{18})$ alkyl; and r is 2.

In one embodiment, $R^5$ and $R^6$ in Formulas 4a, 4b, 4c, 5a, 5b and 5c are each hydrogen.

In one embodiment, $R^{12}$, $R^{13}$, $R^{14}$, $R^{15}$, $R^{16}$, $R^{17}$, $R^{18}$ and $R^{19}$ in Formulas 4a, 4b and 4c are each independently selected from hydrogen, methyl, ethyl and i-propyl; and q is 1.

In one embodiment, $R^{22}$, $R^{23}$, $R^{24}$ and $R^{25}$ in Formulas 5a, 5b and 5c are each independently selected from methyl, ethyl and i-propyl; and $R^{20}$ and $R^{21}$ are each independently selected from hydrogen and methyl; and r is 2.

Among the amino silane polymerization initiator compounds represented by Formulas 4a, 4b, 4c, 5a, 5b and 5c, Formulas 4a, 4b, 5a and 5b are preferred, and Formulas 4a and 5b are most preferred.

Two or more amino silane polymerization initiator compounds may be used in combination.

In one embodiment of the amino silane polymerization initiator compounds of Formula 4 and Formula 5 and the method of manufacturing the same from a compound of Formula 9 and a Lewis base of Formula 10 or 11, X is a chlorine or bromine atom; $R^{3a}$ is selected from $-N(R^{28})R^{29}$ and $(C_1\text{-}C_{18})$ alkyl; $R^{4a}$ is selected from $-N(R^{30})R^{31}$ and $(C_1\text{-}C_{18})$ alkyl; $R^{26}$, $R^{27}$, $R^{28}$, $R^{29}$, $R^{30}$ and $R^{31}$ are each independently selected from $(C_1\text{-}C_{18})$ alkyl; $R^5$ and $R^6$ are each independently selected from hydrogen and $(C_1\text{-}C_{18})$ alkyl; $R^{18}$, $R^{19}$, $R^{20}$ and $R^{21}$ are each independently selected from hydrogen and $(C_1\text{-}C_{18})$ alkyl; $R^{12}$, $R^{13}$, $R^{14}$, $R^{15}$, $R^{16}$ and $R^{17}$ are each independently selected from hydrogen and $(C_1\text{-}C_6)$ alkyl; $R^{22}$, $R^{23}$, $R^{24}$ and $R^{25}$ are each independently selected from $(C_1\text{-}C_{18})$ alkyl; q is 1 and r is 2.

In one preferred embodiment of the amino silane polymerization initiator compounds of Formula 4 and Formula 5 and the method of manufacturing the same from a compound of Formula 9 and a Lewis base of Formula 10 or 11, X is a chlorine or bromine atom; $R^{3a}$ is selected from $-N(R^{28})R^{29}$ and $(C_1\text{-}C_{18})$ alkyl; $R^{4a}$ is selected from $(C_1\text{-}C_{18})$ alkyl; $R^{26}$, $R^{27}$, $R^{28}$ and $R^{29}$ are each independently selected from $(C_1-C_{18})$ alkyl; $R^5$ and $R^6$ are each independently selected from hydrogen and $(C_1-C_{18})$ alkyl; $R^{18}$, $R^{19}$, $R^{20}$ and $R^{21}$ are each independently selected from hydrogen and $(C_1-C_{18})$ alkyl; $R^{12}$, $R^{13}$, $R^{14}$, $R^{15}$, $R^{16}$ and $R^{17}$ are each independently selected from hydrogen and $(C_1-C_6)$ alkyl; $R^{22}$, $R^{23}$, $R^{24}$ and $R^{25}$ are each independently selected from $(C_1-C_{18})$ alkyl; q is 1 and r is 2.

In one preferred embodiment of the amino silane polymerization initiator compounds of Formula 4 and Formula 5 and the method of manufacturing the same from a compound of Formula 9 and a Lewis base of Formula 10 or 11, X is a chlorine atom; $R^{3a}$ and $R^{4a}$ are selected from $(C_1-C_{18})$ alkyl; $R^{26}$ and $R^{27}$ are each independently selected from $(C_1-C_{18})$ alkyl; $R^5$ and $R^6$ are each independently selected from hydrogen and $(C_1-C_{18})$ alkyl; $R^{12}$, $R^{13}$, $R^{14}$, $R^{15}$, $R^{16}$, $R^{17}$, $R^{18}$, $R^{19}$, $R^{20}$ and $R^{21}$ are each independently selected from hydrogen and $(C_1-C_4)$ alkyl; $R^{22}$, $R^{23}$, $R^{24}$ and $R^{25}$ are each independently selected from $(C_1-C_4)$ alkyl; q is 1 and r is 2; and the alkali metal is lithium.

Useful amino halogenated amino silane polymerization initiator precursor compounds of Formula 9 include the following:

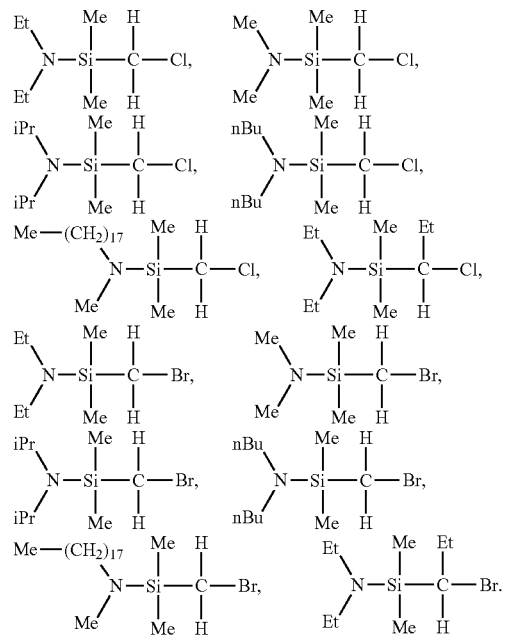

In step (ia) in the synthesis of the amino silane polymerization initiator compound of Formula 4 or 5, the reaction between the amino silane polymerization initiator precursor compound of Formula 9 and the alkali metal is preferably performed in a nonpolar solvent, including hydrocarbon solvent, including aliphatic and aromatic solvent, preferably aliphatic solvent, such as hexane, heptane, pentane, isopar, cyclohexane and methylcyclohexane, for a period ranging from 5 seconds to 3 days, preferably from 1 minute to 2 days, even more preferably from 10 minutes to 18 hours, at a temperature ranging from −60° C. to 130° C., preferably from 0° C. to 100° C. and even more preferably from 20° C. to 70° C., using a molar ratio of the "amino silane polymerization initiator precursor compound" of Formula 9 to alkali metal of usually from 1 to 16, preferably from 1.5 to 8, and even more preferably from 1.8 to 4.0.

The subsequent addition of Lewis base of Formula 10 or Formula 11 is preferably performed in a nonpolar solvent, including hydrocarbon solvent, including aliphatic and aromatic solvent, preferably aliphatic solvent, such as hexane, heptane, pentane, isopar, cyclohexane and methylcyclohexane, usually for a period ranging from 1 second to 5 hours, preferably from 2 seconds to 1 hours, even more preferably from 5 seconds to 15 minutes, at a temperature ranging, for example, from −80° C. to 130° C., preferably from −10° C. to 100° C. and even more preferably from 20° C. to 80° C., using a molar ratio of "amino silane polymerization initiator precursor compound" to "chelating Lewis base" of usually from 0.1 to 30, preferably from 0.5 to 10 and even more preferably from 0.8 to 4.0.

Useful amino silane polymerization initiator compounds of Formula 4 and 5 include the following:

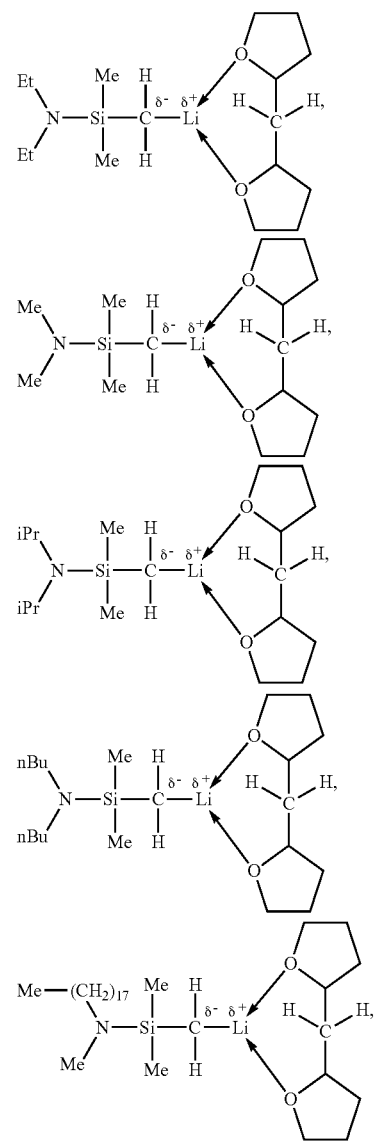

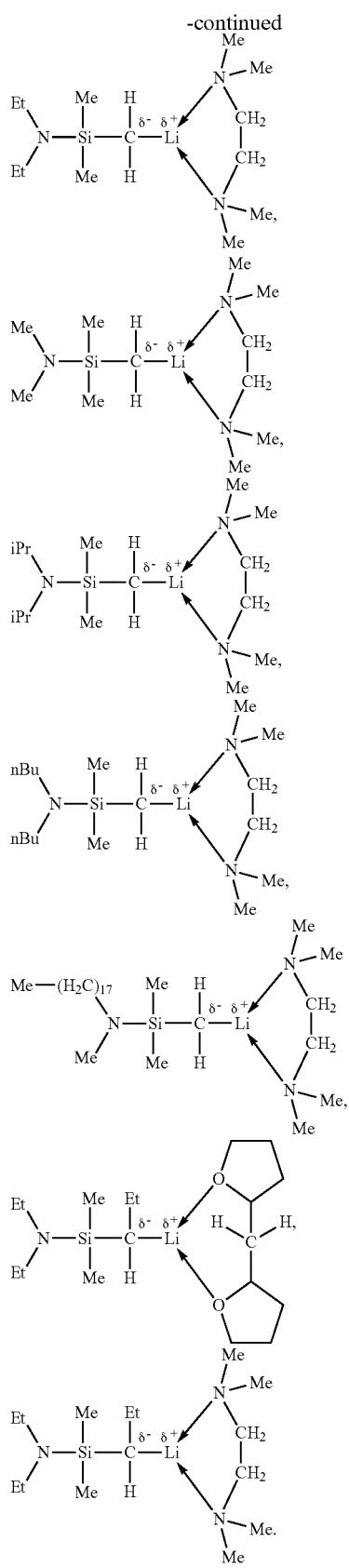

In a preferred embodiment, the amino silane polymerization initiator compounds (described herein) are reacted first with monomers to form living polymers, which are also referred to as alpha-modified living macromolecular compounds. The living polymers are then reacted with the chain end modifier compounds of Formula 6 to form alpha,omega-modified polymers, also referred to herein as modified macromolecular compounds.

Some amino silane polymerization initiator compounds of the present invention may optionally be used together with coupling agents (as described herein) to form branched modified macromolecular compounds.

Randomizer Agents

In addition to the Lewis bases of Formula 10 or 11 required for the formation of the amino silane polymerization initiator compounds of Formula 4 and 5, respectively, additional Lewis bases may optionally be added to the polymerization mixture to adjust the microstructure (the content of vinyl bonds) of the conjugated diolefin portion of diolefin-type homo-, co- or terpolymer, or to adjust the composition distribution of the aromatic vinyl compound in the conjugated diene monomer-containing co- or terpolymer, and thus for example to serve as a randomizer component. The additional Lewis bases are, for example, but not limited to, ether compounds, such as diethyl ether, di-n-butyl ether, ethylene glycol diethyl ether, ethylene glycol dibutylether, diethylene glycol dimethyl ether, propylene glycol dimethyl ether, propylene glycol diethyl ether, propylene glycol dibutylether, alkyltetrahydroforylethers, such as, methyltetrahydrofurylether, ethyltetrahydrofurylether, propyltetrahydrofurylether, butyltetrahydrofurylether, hexyltetrahydrofurylether, octyltetrahydrofurylether, tetrahydrofuran, 2,2-(bistetrahydrofurfuryl)propane, bistetrahydrofurfurylformal, methyl ether of tetrahydrofurfuryl alcohol, ethyl ether of tetrahydrofurfuryl alcohol, butyl ether of tetrahydrofurfuryl alcohol, α-methoxytetrahydrofuran, dimethoxybenzene and dimethoxyethane, and tertiary amine compounds, such as butyl ether of triethylamine, pyridine, N,N,N',N'-tetramethyl ethylenediamine, dipiperidinoethane, methyl ether of N,N-diethylethanolamine, ethyl ether of N,N-diethylethanolamine and N,N-diethylethanolamine.

The above-mentioned optional Lewis bases are used for forming the Lewis base adducts referred to in the definition of the amino silane polymerization initiator compounds of Formula 4 and 5.

Coupling Agents

Coupling agents include tin tetrachloride, tin tetrabromide, tin tetrafluoride, tin tetraiodide, silicon tetrachloride, silicon tetrabromide, silicon tetrafluoride, silicon tetraiodide, alkyl tin and alkyl silicon trihalides or dialkyl tin and dialkyl silicon dihalides. Polymers (macromoleculear compounds) coupled with tin or silicon tetrahalides have a maximum of four arms, polymers coupled with alkyl tin and alkyl silicon trihalides have a maximum of three arms, and polymers coupled with dialkyl tin and dialkyl silicon dihalides have a maximum of two arms. Hexahalo disilanes or hexahalo disiloxanes can also be used as coupling agents resulting in polymers with a maximum of six arms. Useful tin and silicon halides coupling agents include: $SnCl_4$, $(R_1)_2SnCl_2$, $R_1SnCl_3$, $SiCl_4$, $(R_1)_2SiCl_2$, $R_1SiCl_3$, $Cl_3Si$—$SiCl_3$, $Cl_3Si$—$O$—$SiCl_3$, $Cl_3Sn$—$SnCl_3$ and $Cl_3Sn$—$O$—$SnCl_3$ wherein $R_1$ is a hydrocarbyl group, preferably an alkyl group. Examples of tin and silicon alkoxides coupling agents further include: $Sn(OMe)_4$, $Si(OMe)_4$, $Sn(OEt)_4$ and $Si(OEt)_4$. The most preferred coupling agents are: $SnCl_4$, $SiCl_4$, $Sn(OMe)_4$ and $Si(OMe)_4$.

The coupling agents may be added intermittently (or at regular or irregular intervals) or continuously during the polymerization, but are preferably added at a conversion rate of the polymerization of more than 80 percent, and more preferably at a conversion rate of more than 90 percent.

For example, a coupling agent can be continuously added during the polymerization, in cases where asymmetrical coupling is desired. This continuous addition is normally done in a reaction zone separate from the zone where the bulk of the polymerization is occurring. The coupling agent can be added in a hydrocarbon solution, for example, in cyclohexane, to the polymerization admixture, with suitable mixing for distribution and reaction. The coupling agent will typically be added only after a high degree of conversion has already been attained. For instance, the coupling agent will normally be added only after a monomer conversion of greater than about 80 percent has been realized. It will typically be preferred for the monomer conversion to reach at least about 90 percent before the coupling agent is added. Polymers coupled with coupling agents have a minimum of two polymer chain arms.

Preferably, a substantial amount of the polymer chain ends is not terminated prior to the reaction with the coupling agent; that is, living polymer chain ends are present and capable of reacting with the coupling agent in a polymer chain coupling reaction. The coupling reaction occur before, after or during the addition of the chain end-modifying compound of Formula 6. Preferably, the coupling reaction is completed prior to the addition of the chain end-modifying compound. In one embodiment, as a result of the coupling reaction, 80 percent or less of the living polymer chains are reacted with the coupling agent. Preferably 65 percent or less of the polymer chains are reacted with the coupling agent, and more preferably 50 percent or less of the polymer chains are reacted with the coupling agent.

In some embodiments, between 10 and 30 percent of the living polymer chain ends, as determined by GPC, are reacted with coupling agent(s), prior to the addition of the chain end-modifying compound. In other embodiments, between 20 and 35 percent of the living polymer chain ends are reacted with coupling agent(s), prior to the addition of the chain end-modifying compound. In yet other embodiment, between 35 and 50 percent of the living polymer chain ends are reacted with coupling agent(s), prior to the addition of the chain end-modifying compound. The coupling agent may be directly added into the polymer solution without dilution; however, it may be beneficial to provide addition of the coupling agent in solution, such as an inert solvent (for example, cyclohexane). For instance, if different types of coupling agents are used, from 0.01 to 2.0 mol, preferably from 0.02 to 1.5 mol, and more preferably from 0.04 to 0.6 mol, of the coupling agent is utilized for every 4.0 moles of living and thus anionic polymer chain ends.

A combination of coupling agents comprising tin or silicon, as described before, can optionally be used to couple the polymer. A combination of different coupling agents, such as $Bu_2SnCl_2$ and $SnCl_4$; $Me_2SiCl_2$ and $Si(OMe)_4$; $Me_2SiCl_2$ and $SiCl_4$; $SnCl_4$ and $Si(OMe)_4$; $SnCl_4$ and $SiCl_4$ can also be used to couple polymer chains. It is particularly desirable to utilize a combination of tin and silicon coupling agents in tire tread compounds that contain both silica and carbon black. In such cases, the molar ratio of the tin to the silicon compound employed for coupling the elastomeric polymer will normally be within the range of from 20:80 to 95:5; more typically from 40:60 to 90:10, and preferably from 60:40 to 85:15. Most typically, a range of from about 0.001 to 4.5 mmol of coupling agent (tin and silicon compound, silicon coupling agents) is employed per 100 grams of the elastomeric polymer. It is normally preferred to utilize from about 0.05 to about 0.5 mmol of the coupling agent per 100 grams of polymer to obtain the desired Mooney viscosity and to enable subsequent chain end functionalization of the remaining living polymer fraction. Larger quantities tend to produce polymers containing terminally reactive groups or insufficient coupling and only enable an insufficient chain end-modification.

In one embodiment, from 0.01 to less than 5.0 mol, preferably from 0.05 to 2.5 mol, and more preferably from 0.1 to 1.5 mol, of the coupling agent is utilized for every 10.0 moles of living lithium polymer chain ends. The coupling agent can be added in a hydrocarbon solution (e.g. in cyclohexane) to the polymerization admixture in the reactor, with suitable mixing for distribution and reaction.

The polymer coupling reaction may be carried out in a temperature range of from 0° C. to 150° C., preferably from 15° C. to 120° C., and even more preferably from 40° C. to 100° C. There is no limitation for the duration of the coupling reaction. However, with respect to an economical polymerization process, for example, in the case of a batch polymerization process, the coupling reaction is usually stopped at about 5 to 60 minutes after the addition of the coupling agent.

The coupling agent can be added in a hydrocarbon solution, for example in cyclohexane, to the polymerization admixture in the reactor with suitable mixing for distribution and reaction.

Chain End-Modifying Compounds

For further control of polymer properties, a chain end-modifying compound of Formula 6 can be employed in the present invention. The term "chain end-modifying compound" is intended to mean the compounds of the present invention described herein with reference to Formula 6, including Formula 7 and Formula 8, described above and in more detail below.

The chain end-modifying compound includes compounds of Formula 7 as generally defined above.

In one embodiment, Y is a ($C_1$-$C_{16}$) divalent alkyl group or ($C_1$-$C_{16}$) divalent aralkyl group.

In one embodiment, Y is alkylene. In a further embodiment, the alkylene is selected from —$CH_2$— (methylene), –$(CH_2)_2$— (ethylidene), –$(CH_2)_3$— (propylidene) and —$(CH_2)_4$-(butylidene).

In one embodiment, Y is a divalent aralkylene group. In a further embodiment, the aralkylene group is selected from —$CH_2$—$C_6H_4$—$CH_2$— (xylidene) and —$C_6H_4$—$C(CH_3)_2$—$C_6H_4$—.

In one embodiment, $R^2$, $R^7$, $R^8$ and $R^9$ are each independently a ($C_1$-$C_{16}$) alkyl. In a further embodiment, the alkyl is selected from $CH_3$— (methyl), $CH_3$—$CH_2$— (ethyl), $CH_3$—$(CH_2)_2$-(propyl), $CH_3$—$(CH_2)_3$ (n-butyl) and $CH_3$—$C(CH_3)_2$ (tert-butyl).

In one embodiment of Formula 7, Y is selected from the group consisting of linear $C_1$-$C_{10}$ alkyl (divalent), cyclic $C_6$-$C_{12}$ alkyl (divalent), $C_6$-$C_{15}$ aryl (divalent) and $C_7$-$C_{12}$ alkylaryl (divalent).

In one embodiment of Formula 7, n and t are each independently selected from an integer of 0 and 1; s and v are each independently selected from an integer of 2 and 3.

In one embodiment, the chain end-modifying compound is the compound of Formula 7 where $M^1$ is a silicon atom; s and v are each an integer selected from 2 and 3; and n and t are each an integer selected from 0 and 1. Specific preferred species of the chain end-modifying compound of Formula 7 include the following:

$(MeO)_3Si$—$(CH_2)_3$—S—$Si(Me)_2$—S—$(CH_2)_3$—$Si(OMe)_3$,
$(MeO)_3Si$—$(CH_2)_3$—S—$Si(Et)_2$—S—$(CH_2)_3$—$Si(OMe)_3$, (MeO)₃Si—(CH₂)₃—S—Si(Bu)₂-S—(CH₂)₃—Si(OMe)₃,
(EtO)₃Si—(CH₂)₃—S—Si(Me)₂-S—(CH₂)₃—Si(OEt)₃,
(EtO)₃Si—(CH₂)₃—S—Si(Et)₂-S—(CH₂)₃—Si(OEt)₃,
(EtO)₃Si—(CH₂)₃—S—Si(Bu)₂-S—(CH₂)₃—Si(OEt)₃,
(PrO)₃Si—(CH₂)₃—S—Si(Me)₂-S—(CH₂)₃—Si(OPr)₃,
(PrO)₃Si—(CH₂)₃—S—Si(Et)₂-S—(CH₂)₃—Si(OPr)₃,
(PrO)₃Si—(CH₂)₃—S—Si(Bu)₂-S—(CH₂)₃—Si(OPr)₃,
(MeO)₃Si—(CH₂)₂—S—Si(Me)₂-S—(CH₂)₂—Si(OMe)₃,
(MeO)₃Si—(CH₂)₂—S—Si(Et)₂-S—(CH₂)₂—Si(OMe)₃,
(MeO)₃Si—(CH₂)₂—S—Si(Bu)₂-S—(CH₂)₂—Si(OMe)₃,
(EtO)₃Si—(CH₂)₂—S—Si(Me)₂-S—(CH₂)₂—Si(OEt)₃,
(EtO)₃Si—(CH₂)₂—S—Si(Et)₂-S—(CH₂)₂—Si(OEt)₃,
(EtO)₃Si—(CH₂)₂—S—Si(Bu)₂-S—(CH₂)₂—Si(OEt)₃,
(PrO)₃Si—(CH₂)₂—S—Si(Me)₂-S—(CH₂)₂—Si(OPr)₃,
(PrO)₃Si—(CH₂)₂—S—Si(Et)₂-S—(CH₂)₂—Si(OPr)₃,
(PrO)₃Si—(CH₂)₂—S—Si(Bu)₂-S—(CH₂)₂—Si(OPr)₃,
(MeO)₃Si—CH₂—S—Si(Me)₂-S—CH₂—Si(OMe)₃,
(MeO)₃Si—CH₂—S—Si(Et)₂-S—CH₂—Si(OMe)₃,
(MeO)₃Si—CH₂—S—Si(Bu)₂-S—CH₂—Si(OMe)₃,
(EtO)₃Si—CH₂—S—Si(Me)₂-S—CH₂—Si(OEt)₃,
(EtO)₃Si—CH₂—S—Si(Et)₂-S—CH₂—Si(OEt)₃,
(EtO)₃Si—CH₂—S—Si(Bu)₂-S—CH₂—Si(OEt)₃,
(PrO)₃Si—CH₂—S—Si(Me)₂-S—CH₂—Si(OPr)₃,
(PrO)₃Si—CH₂—S—Si(Et)₂-S—CH₂—Si(OPr)₃,
(PrO)₃Si—CH₂—S—Si(Bu)₂-S—CH₂—Si(OPr)₃,
(MeO)₃Si—CH₂—CMe₂-CH₂—S—Si(Me)₂-S—CH₂—CMe₂-CH₂—Si(OMe)₃,
(MeO)₃Si—CH₂—CMe₂-CH₂—S—Si(Et)₂-S—CH₂—CMe₂-CH₂—Si(OMe)₃,
(MeO)₃Si—CH₂—CMe₂-CH₂—S—Si(Bu)₂-S—CH₂—CMe₂-CH₂—Si(OMe)₃,
(EtO)₃Si—CH₂—CMe₂-CH₂—S—Si(Me)₂-S—CH₂—CMe₂-CH₂—Si(OEt)₃,
(EtO)₃Si—CH₂—CMe₂-CH₂—S—Si(Et)₂-S—CH₂—CMe₂-CH₂—Si(OEt)₃,
(EtO)₃Si—CH₂—CMe₂-CH₂—S—Si(Bu)₂-S—CH₂—CMe₂-CH₂—Si(OEt)₃,
(PrO)₃Si—CH₂—CMe₂-CH₂—S—Si(Me)₂-S—CH₂—CMe₂-CH₂—Si(OPr)₃,
(PrO)₃Si—CH₂—CMe₂-CH₂—S—Si(Et)₂-S—CH₂—CMe₂-CH₂—Si(OPr)₃,
(PrO)₃Si—CH₂—CMe₂-CH₂—S—Si(Bu)₂-S—CH₂—CMe₂-CH₂—Si(OPr)₃,
(MeO)₃Si—CH₂—C(H)Me-CH₂—S—Si(Me)₂-S—CH₂—C(H)Me-CH₂—Si(OMe)₃,
(MeO)₃Si—CH₂—C(H)Me-CH₂—S—Si(Et)₂-S—CH₂—C(H)Me-CH₂—Si(OMe)₃,
(MeO)₃Si—CH₂—C(H)Me-CH₂—S—Si(Bu)₂-S—CH₂—C(H)Me-CH₂—Si(OMe)₃,
(EtO)₃Si—CH₂—C(H)Me-CH₂—S—Si(Me)₂-S—CH₂—C(H)Me-CH₂—Si(OEt)₃,
(EtO)₃Si—CH₂—C(H)Me-CH₂—S—Si(Et)₂-S—CH₂—C(H)Me-CH₂—Si(OEt)₃,
(EtO)₃Si—CH₂—C(H)Me-CH₂—S—Si(Bu)₂-S—CH₂—C(H)Me-CH₂—Si(OEt)₃,
(PrO)₃Si—CH₂—C(H)Me-CH₂—S—Si(Me)₂-S—CH₂—C(H)Me-CH₂—Si(OPr)₃,
(PrO)₃Si—CH₂—C(H)Me-CH₂—S—Si(Et)₂-S—CH₂—C(H)Me-CH₂—Si(OPr)₃,
(PrO)₃Si—CH₂—C(H)Me-CH₂—S—Si(Bu)₂-S—CH₂—C(H)Me-CH₂—Si(OPr)₃,
(MeO)₂(Me)Si—(CH₂)₃—S—Si(Me)₂-S—Si(Me)₂-S—(CH₂)₃—Si(OMe)₂(Me),
(MeO)₂(Me)Si—(CH₂)₃—S—Si(Et)₂-S—(CH₂)₃—Si(OMe)₂(Me),
(MeO)₂(Me)Si—(CH₂)₃—S—Si(Bu)₂-S—(CH₂)₃—Si(OMe)₂(Me),
(EtO)₂(Me)Si—(CH₂)₃—S—Si(Me)₂-S—(CH₂)₃—Si(OEt)₂(Me),
(EtO)₂(Me)Si—(CH₂)₃—S—Si(Et)₂-S—(CH₂)₃—Si(OEt)₂(Me),
(EtO)₂(Me)Si—(CH₂)₃—S—Si(Bu)₂-S—Si(Bu)₂-S—(CH₂)₃—Si(OEt)₂(Me),
(PrO)₂(Me)Si—(CH₂)₃—S—Si(Me)₂-S—(CH₂)₃—Si(OPr)₂(Me),
(PrO)₂(Me)Si—(CH₂)₃—S—Si(Et)₂-S—(CH₂)₃—Si(OPr)₂(Me),
(PrO)₂(Me)Si—(CH₂)₃—S—Si(Bu)₂-S—(CH₂)₃—Si(OPr)₂(Me),
(MeO)₂(Me)Si—(CH₂)₂—S—Si(Me)₂-S—(CH₂)₂—Si(OMe)₂(Me),
(MeO)₂(Me)Si—(CH₂)₂—S—Si(Et)₂-S—(CH₂)₂—Si(OMe)₂(Me),
(MeO)₂(Me)Si—(CH₂)₂—S—Si(Bu)₂-S—(CH₂)₂—Si(OMe)₂(Me),
(EtO)₂(Me)Si—(CH₂)₂—S—Si(Me)₂-S—(CH₂)₂—Si(OEt)₂(Me),
(EtO)₂(Me)Si—(CH₂)₂—S—Si(Et)₂-S—(CH₂)₂—Si(OEt)₂(Me),
(EtO)₂(Me)Si—(CH₂)₂—S—Si(Bu)₂-S—(CH₂)₂—Si(OEt)₂(Me),
(PrO)₂(Me)Si—(CH₂)₂—S—Si(Me)₂-S—(CH₂)₂—Si(OPr)₂(Me),
(PrO)₂(Me)Si—(CH₂)₂—S—Si(Et)₂-S—(CH₂)₂—Si(OPr)₂(Me),
(PrO)₂(Me)Si—(CH₂)₂—S—Si(Bu)₂-S—(CH₂)₂—Si(OPr)₂(Me),
(MeO)₂(Me)Si—CH₂—S—Si(Me)₂-S—CH₂—Si(OMe)₂(Me),
(MeO)₂(Me)Si—CH₂—S—Si(Et)₂-S—CH₂—Si(OMe)₂(Me),
(MeO)₂(Me)Si—CH₂—S—Si(Bu)₂-S—CH₂—Si(OMe)₂(Me),
(EtO)₂(Me)Si—CH₂—S—Si(Me)₂-S—CH₂—Si(OEt)₂(Me),
(EtO)₂(Me)Si—CH₂—S—Si(Et)₂-S—CH₂—Si(OEt)₂(Me),
(EtO)₂(Me)Si—CH₂—S—Si(Bu)₂-S—CH₂—Si(OEt)₂(Me),
(PrO)₂(Me)Si—CH₂—S—Si(Me)₂-S—CH₂—Si(OPr)₂(Me),
(PrO)₂(Me)Si—CH₂—S—Si(Et)₂-S—CH₂—Si(OPr)₂(Me),
(PrO)₂(Me)Si—CH₂—S—Si(Bu)₂-S—CH₂—Si(OPr)₂(Me),
(MeO)₂(Me)Si—CH₂—CMe₂-CH₂—S—Si(Me)₂-S—CH₂—CMe₂-CH₂—Si(OMe)₂(Me),
(MeO)₂(Me)Si—CH₂—CMe₂-CH₂—S—Si(Et)₂-S—CH₂—CMe₂-CH₂—Si(OMe)₂(Me),
(MeO)₂(Me)Si—CH₂—CMe₂-CH₂—S—Si(Bu)₂-S—CH₂—CMe₂-CH₂—Si(OMe)₂(Me),
(EtO)₂(Me)Si—CH₂—CMe₂-CH₂—S—Si(Me)₂-S—CH₂—CMe₂-CH₂—Si(OEt)₂(Me),
(EtO)₂(Me)Si—CH₂—CMe₂-CH₂—S—Si(Et)₂-S—CH₂—CMe₂-CH₂—Si(OEt)₂(Me),
(EtO)₂(Me)Si—CH₂—CMe₂-CH₂—S—Si(Bu)₂-S—CH₂—CMe₂-CH₂—Si(OEt)₂(Me),
(PrO)₂(Me)Si—CH₂—CMe₂-CH₂—S—Si(Me)₂-S—CH₂—CMe₂-CH₂—Si(OPr)₂(Me),
(PrO)₂(Me)Si—CH₂—CMe₂-CH₂—S—Si(Et)₂-S—CH₂—CMe₂-CH₂—Si(OPr)₂(Me),
(PrO)₂(Me)Si—CH₂—CMe₂-CH₂—S—Si(Bu)₂-S—CH₂—CMe₂-CH₂—Si(OPr)₂(Me), (MeO)₂(Me)Si—CH₂—C(H)Me-CH₂—S—Si(Me)₂-S—CH₂—C(H)Me-CH₂—Si(OMe)₂(Me),
(MeO)₂(Me)Si—CH₂—C(H)Me-CH₂—S—Si(Et)₂-S—CH₂—C(H)Me-CH₂—Si(OMe)₂(Me),
(MeO)₂(Me)Si—CH₂—C(H)Me-CH₂—S—Si(Bu)₂-S—CH₂—C(H)Me-CH₂—Si(OMe)₂(Me),
(EtO)₂(Me)Si—CH₂—C(H)Me-CH₂—S—Si(Me)₂-S—CH₂—C(H)Me-CH₂—Si(OEt)₂(Me),
(EtO)₂(Me)Si—CH₂—C(H)Me-CH₂—S—Si(Et)₂-S—CH₂—C(H)Me-CH₂—Si(OEt)₂(Me),
(EtO)₂(Me)Si—CH₂—C(H)Me-CH₂—S—Si(Bu)₂-S—CH₂—C(H)Me-CH₂—Si(OEt)₂(Me),
(PrO)₂(Me)Si—CH₂—C(H)Me-CH₂—S—Si(Me)₂-S—CH₂—C(H)Me-CH₂—Si(OPr)₂(Me),
(PrO)₂(Me)Si—CH₂—C(H)Me-CH₂—S—Si(Et)₂-S—CH₂—C(H)Me-CH₂—Si(OPr)₂(Me),
(PrO)₂(Me)Si—CH₂—C(H)Me-CH₂—S—Si(Bu)₂-S—CH₂—C(H)Me-CH₂—Si(OPr)₂(Me),
(MeO)₃Si—(CH₂)₃—S—Sn(Me)₂-S—(CH₂)₃—Si(OMe)₃,
(MeO)₃Si—(CH₂)₃—S—Sn(Et)₂-S—(CH₂)₃—Si(OMe)₃,
(MeO)₃Si—(CH₂)₃—S—Sn(Bu)₂-S—(CH₂)₃—Si(OMe)₃,
(EtO)₃Si—(CH₂)₃—S—Sn(Me)₂-S—(CH₂)₃—Si(OEt)₃,
(EtO)₃Si—(CH₂)₃—S—Sn(Et)₂-S—(CH₂)₃—Si(OEt)₃,
(EtO)₃Si—(CH₂)₃—S—Sn(Bu)₂-S—(CH₂)₃—Si(OEt)₃,
(PrO)₃Si—(CH₂)₃—S—Sn(Me)₂-S—(CH₂)₃—Si(OPr)₃,
(PrO)₃Si—(CH₂)₃—S—Sn(Et)₂-S—(CH₂)₃—Si(OPr)₃,
(PrO)₃Si—(CH₂)₃—S—Sn(Bu)₂-S—(CH₂)₃—Si(OPr)₃,
(MeO)₃Si—(CH₂)₂—S—Sn(Me)₂-S—(CH₂)₂—Si(OMe)₃,
(MeO)₃Si—(CH₂)₂—S—Sn(Et)₂-S—(CH₂)₂—Si(OMe)₃,
(MeO)₃Si—(CH₂)₂—S—Sn(Bu)₂-S—(CH₂)₂—Si(OMe)₃,
(EtO)₃Si—(CH₂)₂—S—Sn(Me)₂-S—(CH₂)₂—Si(OEt)₃,
(EtO)₃Si—(CH₂)₂—S—Sn(Et)₂-S—(CH₂)₂—Si(OEt)₃,
(EtO)₃Si—(CH₂)₂—S—Sn(Bu)₂-S—(CH₂)₂—Si(OEt)₃,
(PrO)₃Si—(CH₂)₂—S—Sn(Me)₂-S—(CH₂)₂—Si(OPr)₃,
(PrO)₃Si—(CH₂)₂—S—Sn(Et)₂-S—(CH₂)₂—Si(OPr)₃,
(PrO)₃Si—(CH₂)₂—S—Sn(Bu)₂-S—(CH₂)₂—Si(OPr)₃,
(MeO)₃Si—CH₂—S—Sn(Me)₂-S—CH₂—Si(OMe)₃,
(MeO)₃Si—CH₂—S—Sn(Et)₂-S—CH₂—Si(OMe)₃,
(MeO)₃Si—CH₂—S—Sn(Bu)₂-S—CH₂—Si(OMe)₃,
(EtO)₃Si—CH₂—S—Sn(Me)₂-S—CH₂—Si(OEt)₃,
(EtO)₃Si—CH₂—S—Sn(Et)₂-S—CH₂—Si(OEt)₃,
(EtO)₃Si—CH₂—S—Sn(Bu)₂-S—CH₂—Si(OEt)₃,
(PrO)₃Si—CH₂—S—Sn(Me)₂-S—CH₂—Si(OPr)₃,
(PrO)₃Si—CH₂—S—Sn(Et)₂-S—CH₂—Si(OPr)₃,
(PrO)₃Si—CH₂—S—Sn(Bu)₂-S—CH₂—Si(OPr)₃,
(MeO)₃Si—CH₂—CMe₂-CH₂—S—Sn(Me)₂-S—CH₂—CMe₂-CH₂—Si(OMe)₃,
(MeO)₃Si—CH₂—CMe₂-CH₂—S—Sn(Et)₂-S—CH₂—CMe₂-CH₂—Si(OMe)₃,
(MeO)₃Si—CH₂—CMe₂-CH₂—S—Sn(Bu)₂-S—CH₂—CMe₂-CH₂—Si(OMe)₃,
(EtO)₃Si—CH₂—CMe₂-CH₂—S—Sn(Me)₂-S—CH₂—CMe₂-CH₂—Si(OEt)₃,
(EtO)₃Si—CH₂—CMe₂-CH₂—S—Sn(Et)₂-S—CH₂—CMe₂-CH₂—Si(OEt)₃,
(EtO)₃Si—CH₂—CMe₂-CH₂—S—Sn(Bu)₂-S—CH₂—CMe₂-CH₂—Si(OEt)₃,
(PrO)₃Si—CH₂—CMe₂-CH₂—S—Sn(Me)₂-S—CH₂—CMe₂-CH₂—Si(OPr)₃,
(PrO)₃Si—CH₂—CMe₂-CH₂—S—Sn(Et)₂-S—CH₂—CMe₂-CH₂—Si(OPr)₃,
(PrO)₃Si—CH₂—CMe₂-CH₂—S—Sn(Bu)₂-S—CH₂—CMe₂-CH₂—Si(OPr)₃,
(MeO)₃Si—CH₂—C(H)Me-CH₂—S—Sn(Me)₂-S—CH₂—C(H)Me-CH₂—Si(OMe)₃,
(MeO)₃Si—CH₂—C(H)Me-CH₂—S—Sn(Et)₂-S—CH₂—C(H)Me-CH₂—Si(OMe)₃,
(MeO)₃Si—CH₂—C(H)Me-CH₂—S—Sn(Bu)₂-S—CH₂—C(H)Me-CH₂—Si(OMe)₃,
(EtO)₃Si—CH₂—C(H)Me-CH₂—S—Sn(Me)₂-S—CH₂—C(H)Me-CH₂—Si(OEt)₃,
(EtO)₃Si—CH₂—C(H)Me-CH₂—S—Sn(Et)₂-S—CH₂—C(H)Me-CH₂—Si(OEt)₃,
(EtO)₃Si—CH₂—C(H)Me-CH₂—S—Sn(Bu)₂-S—CH₂—C(H)Me-CH₂—Si(OEt)₃,
(PrO)₃Si—CH₂—C(H)Me-CH₂—S—Sn(Me)₂-S—CH₂—C(H)Me-CH₂—Si(OPr)₃,
(PrO)₃Si—CH₂—C(H)Me-CH₂—S—Sn(Et)₂-S—CH₂—C(H)Me-CH₂—Si(OPr)₃,
(PrO)₃Si—CH₂—C(H)Me-CH₂—S—Sn(Bu)₂-S—CH₂—C(H)Me-CH₂—Si(OPr)₃,
(MeO)₂(Me)Si—(CH₂)₃—S—Sn(Me)₂-S—(CH₂)₃—Si(OMe)₂(Me),
(MeO)₂(Me)Si—(CH₂)₃—S—Sn(Et)₂-S—(CH₂)₃—Si(OMe)₂(Me),
(MeO)₂(Me)Si—(CH₂)₃—S—Sn(Bu)₂-S—(CH₂)₃—Si(OMe)₂(Me),
(EtO)₂(Me)Si—(CH₂)₃—S—Sn(Me)₂-S—(CH₂)₃—Si(OEt)₂(Me),
(EtO)₂(Me)Si—(CH₂)₃—S—Sn(Et)₂-S—(CH₂)₃—Si(OEt)₂(Me),
(EtO)₂(Me)Si—(CH₂)₃—S—Sn(Bu)₂-S—(CH₂)₃—Si(OEt)₂(Me),
(PrO)₂(Me)Si—(CH₂)₃—S—Sn(Me)₂-S—(CH₂)₃—Si(OPr)₂(Me),
(PrO)₂(Me)Si—(CH₂)₃—S—Sn(Et)₂-S—(CH₂)₃—Si(OPr)₂(Me),
(PrO)₂(Me)Si—(CH₂)₃—S—Sn(Bu)₂-S—(CH₂)₃—Si(OPr)₂(Me),
(MeO)₂(Me)Si—(CH₂)₂—S—Sn(Me)₂-S—(CH₂)₂—Si(OMe)₂(Me),
(MeO)₂(Me)Si—(CH₂)₂—S—Sn(Et)₂-S—(CH₂)₂—Si(OMe)₂(Me),
(MeO)₂(Me)Si—(CH₂)₂—S—Sn(Bu)₂-S—(CH₂)₂—Si(OMe)₂(Me),
(EtO)₂(Me)Si—(CH₂)₂—S—Sn(Me)₂-S—(CH₂)₂—Si(OEt)₂(Me),
(EtO)₂(Me)Si—(CH₂)₂—S—Sn(Et)₂-S—(CH₂)₂—Si(OEt)₂(Me),
(EtO)₂(Me)Si—(CH₂)₂—S—Sn(Bu)₂-S—(CH₂)₂—Si(OEt)₂(Me),
(PrO)₂(Me)Si—(CH₂)₂—S—Sn(Me)₂-S—(CH₂)₂—Si(OPr)₂(Me),
(PrO)₂(Me)Si—(CH₂)₂—S—Sn(Et)₂-S—(CH₂)₂—Si(OPr)₂(Me),
(PrO)₂(Me)Si—(CH₂)₂—S—Sn(Bu)₂-S—(CH₂)₂—Si(OPr)₂(Me),
(MeO)₂(Me)Si—CH₂—S—Sn(Me)₂-S—CH₂—Si(OMe)₂(Me),
(MeO)₂(Me)Si—CH₂—S—Sn(Et)₂-S—CH₂—Si(OMe)₂(Me),
(MeO)₂(Me)Si—CH₂—S—Sn(Bu)₂-S—CH₂—Si(OMe)₂(Me),
(EtO)₂(Me)Si—CH₂—S—Sn(Me)₂-S—CH₂—Si(OEt)₂(Me),
(EtO)₂(Me)Si—CH₂—S—Sn(Et)₂-S—CH₂—Si(OEt)₂(Me),
(EtO)₂(Me)Si—CH₂—S—Sn(Bu)₂-S—CH₂—Si(OEt)₂(Me),
(PrO)₂(Me)Si—CH₂—S—Sn(Me)₂-S—CH₂—Si(OPr)₂(Me),
(PrO)₂(Me)Si—CH₂—S—Sn(Et)₂-S—CH₂—Si(OPr)₂(Me), (PrO)$_2$(Me)Si—CH$_2$—S—Sn(Bu)$_2$-S—CH$_2$—Si(OPr)$_2$ (Me),
(MeO)$_2$(Me)Si—CH$_2$—CMe$_2$-CH$_2$—S—Sn(Me)$_2$-S—CH$_2$—CMe$_2$-CH$_2$—Si(OMe)$_2$(Me),
(MeO)$_2$(Me)Si—CH$_2$—CMe$_2$-CH$_2$—S—Sn(Et)$_2$-S—CH$_2$—CMe$_2$-CH$_2$—Si(OMe)$_2$(Me),
(MeO)$_2$(Me)Si—CH$_2$—CMe$_2$-CH$_2$—S—Sn(Bu)$_2$-S—CH$_2$—CMe$_2$-CH$_2$—Si(OMe)$_2$(Me),
(EtO)$_2$(Me)Si—CH$_2$—CMe$_2$-CH$_2$—S—Sn(Me)$_2$-S—CH$_2$—CMe$_2$-CH$_2$—Si(OEt)$_2$(Me),
(EtO)$_2$(Me)Si—CH$_2$—CMe$_2$-CH$_2$—S—Sn(Et)$_2$-S—CH$_2$—CMe$_2$-CH$_2$—Si(OEt)$_2$(Me),
(EtO)$_2$(Me)Si—CH$_2$—CMe$_2$-CH$_2$—S—Sn(Bu)$_2$-S—CH$_2$—CMe$_2$-CH$_2$—Si(OEt)$_2$(Me),
(PrO)$_2$(Me)Si—CH$_2$—CMe$_2$-CH$_2$—S—Sn(Me)$_2$-S—CH$_2$—CMe$_2$-CH$_2$—Si(OPr)$_2$(Me),
(PrO)$_2$(Me)Si—CH$_2$—CMe$_2$-CH$_2$—S—Sn(Et)$_2$-S—CH$_2$—CMe$_2$-CH$_2$—Si(OPr)$_2$(Me),
(PrO)$_2$(Me)Si—CH$_2$—CMe$_2$-CH$_2$—S—Sn(Bu)$_2$-S—CH$_2$—CMe$_2$-CH$_2$—Si(OPr)$_2$(Me),
(MeO)$_2$(Me)Si—CH$_2$—C(H)Me-CH$_2$—S—Sn(Me)$_2$-S—CH$_2$—C(H)Me-CH$_2$—Si(OMe)$_2$(Me),
(MeO)$_2$(Me)Si—CH$_2$—C(H)Me-CH$_2$—S—Sn(Et)$_2$-S—CH$_2$—C(H)Me-CH$_2$—Si(OMe)$_2$(Me),
(MeO)$_2$(Me)Si—CH$_2$—C(H)Me-CH$_2$—S—Sn(Bu)$_2$-S—CH$_2$—C(H)Me-CH$_2$—Si(OMe)$_2$(Me),
(EtO)$_2$(Me)Si—CH$_2$—C(H)Me-CH$_2$—S—Sn(Me)$_2$-S—CH$_2$—C(H)Me-CH$_2$—Si(OEt)$_2$(Me),
(EtO)$_2$(Me)Si—CH$_2$—C(H)Me-CH$_2$—S—Sn(Et)$_2$-S—CH$_2$—C(H)Me-CH$_2$—Si(OEt)$_2$(Me),
(EtO)$_2$(Me)Si—CH$_2$—C(H)Me-CH$_2$—S—Sn(Bu)$_2$-S—CH$_2$—C(H)Me-CH$_2$—Si(OEt)$_2$(Me),
(PrO)$_2$(Me)Si—CH$_2$—C(H)Me-CH$_2$—S—Sn(Me)$_2$-S—CH$_2$—C(H)Me-CH$_2$—Si(OPr)$_2$(Me),
(PrO)$_2$(Me)Si—CH$_2$—C(H)Me-CH$_2$—S—Sn(Et)$_2$-S—CH$_2$—C(H)Me-CH$_2$—Si(OPr)$_2$(Me),
(PrO)$_2$(Me)Si—CH$_2$—C(H)Me-CH$_2$—S—Sn(Bu)$_2$-S—CH$_2$—C(H)Me-CH$_2$—Si(OPr)$_2$(Me).

The chain end-modifying compound includes compounds of Formula 8 as generally defined above.

In one embodiment, s is an integer selected from 2 and 3; n is an integer selected from 0 and 1; R$^{1a}$ is selected from (C$_1$-C$_4$) alkyl; R$^2$ is independently selected from (C$_1$-C$_{10}$) alkyl; Y is (C$_1$-C$_{12}$) alkyl, even more preferably a (C$_1$-C$_5$) alkyl, and most preferably a (C$_1$-C$_5$) alkyl. In another embodiment, Y is a (C$_7$-C$_{25}$) alkylaryl, more preferably a (C$_7$-C$_{16}$) alkylaryl, and most preferably a (C$_7$-C$_{12}$) alkylaryl.

In yet another embodiment, R$^7$, R$^8$ and R$^{11}$ are preferably independently selected from (C$_1$-C$_5$) alkyl.

In one embodiment, R$^{11}$ is selected from (C$_1$-C$_{16}$) alkyl; R$^{1a}$ is selected from (C$_1$-C$_4$) alkyl; R$^2$, R$^7$ and R$^8$ are the same or different, and are each independently selected from hydrogen (H) and (C$_1$-C$_{16}$) alkyl; and alkyl especially includes Me, Et, Pr and Bu.

In one embodiment, Y is selected from a (C$_1$-C$_{16}$) divalent alkyl group and a (C$_1$-C$_{16}$) divalent aralkyl group.

In one embodiment, Y is alkylene. In a further embodiment, the alkylene is selected from —CH$_2$— (methylene), -(CH$_2$)$_2$— (ethylidene), -(CH$_2$)$_3$— (propylidene) and —(CH$_2$)$_4$-(butylidene).

In one embodiment, Y is a divalent aralkylene group. In a further embodiment, the aralkylene group is selected from —CH$_2$—C$_6$H$_4$—CH$_2$— (xylidene) and —C$_6$H$_4$—C(CH$_3$)$_2$—C$_6$H$_4$—.

In one embodiment, R$^{1a}$, R$^2$, R$^7$, R$^8$ and R$^{11}$ are each independently an alkyl. In a further embodiment, the alkyl is selected from CH$_3$— (methyl), CH$_3$—CH$_2$— (ethyl), CH$_3$—(CH$_2$)$_2$-(propyl), CH$_3$—(CH$_2$)$_3$(n-butyl) and CH$_3$—C(CH$_3$)$_2$(tert-butyl).

In one embodiment of Formula 8, Y is selected from the group consisting of linear C$_1$-C$_{10}$ alkyl (divalent), cyclic C$_6$-C$_{12}$ alkyl (divalent), C$_6$-C$_{15}$ aryl (divalent) and C$_7$-C$_{12}$ alkylaryl (divalent).

In one embodiment of Formula 8, n is an integer of 0 or 1; s is an integer of 2 or 3.

In one embodiment of the chain end-modifying compound of Formula 8, M$^1$ is a silicon atoms; s is an integer selected from 2 and 3; and n is an integer selected from 0 and 1. Specific preferred species of the chain end-modifying compound of Formula 8 include the following compounds and their corresponding Lewis base adducts:

(MeO)$_3$Si—(CH$_2$)$_3$—S—SiMe$_3$, (EtO)$_3$Si—(CH$_2$)$_3$—S—SiMe$_3$, (PrO)$_3$Si—(CH$_2$)$_3$—S—SiMe$_3$, (BuO)$_3$Si—(CH$_2$)$_3$—S—SiMe$_3$, (MeO)$_3$Si—(CH$_2$)$_2$—S—SiMe$_3$, (EtO)$_3$Si—(CH$_2$)$_2$—S—SiMe$_3$, (PrO)$_3$Si—(CH$_2$)$_2$—S—SiMe$_3$, (BuO)$_3$Si—(CH$_2$)$_2$—S—SiMe$_3$, (MeO)$_3$Si—CH$_2$—S—SiMe$_3$, (EtO)$_3$Si—CH$_2$—S—SiMe$_3$, (PrO)$_3$Si—CH$_2$—S—SiMe$_3$, (BuO)$_3$Si—CH$_2$—S—SiMe$_3$, (MeO)$_3$Si—CH$_2$—CMe$_2$-CH$_2$—S—SiMe$_3$, (EtO)$_3$Si—CH$_2$—CMe$_2$-CH$_2$—S—SiMe$_3$, (PrO)$_3$Si—CH$_2$—CMe$_2$-CH$_2$—S—SiMe$_3$, (BuO)$_3$Si—CH$_2$—CMe$_2$-CH$_2$—S—SiMe$_3$, ((MeO)$_3$Si—CH$_2$—C(H)Me-CH$_2$—S—SiMe$_3$, (EtO)$_3$Si—CH$_2$—C(H)Me-CH$_2$—S—SiMe$_3$, (PrO)$_3$Si—CH$_2$—C(H)Me-CH$_2$—S—SiMe$_3$, (BuO)$_3$Si—CH$_2$—C(H)Me-CH$_2$—S—SiMe$_3$, (MeO)$_2$(Me)Si—(CH$_2$)$_3$—S—SiMe$_3$, (EtO)$_2$(Me)Si—(CH$_2$)$_3$—S—SiMe$_3$, (PrO)$_2$(Me)Si—(CH$_2$)$_3$—S—SiMe$_3$, (BuO)$_2$(Me)Si—(CH$_2$)$_3$—S—SiMe$_3$, (MeO)$_2$(Me)Si—(CH$_2$)$_2$—S—SiMe$_3$, (EtO)$_2$(Me)Si—(CH$_2$)$_2$—S—SiMe$_3$, (PrO)$_2$(Me)Si—(CH$_2$)$_2$—S—SiMe$_3$, (BuO)$_2$(Me)Si—(CH$_2$)$_2$—S—SiMe$_3$, (MeO)$_2$(Me)Si—CH$_2$—S—SiMe$_3$, (EtO)$_2$(Me)Si—CH$_2$—S—SiMe$_3$, (PrO)$_2$(Me)Si—CH$_2$—S—SiMe$_3$, (BuO)$_2$(Me)Si—CH$_2$—S—SiMe$_3$, (MeO)$_2$(Me)Si—CH$_2$—CMe$_2$-CH$_2$—S—SiMe$_3$, (EtO)$_2$(Me)Si—CH$_2$—CMe$_2$-CH$_2$—S—SiMe$_3$, (PrO)$_2$(Me)Si—CH$_2$—CMe$_2$-CH$_2$—S—SiMe$_3$, (BuO)$_2$(Me)Si—CH$_2$-Me$_2$-CH$_2$—S—SiMe$_3$, ((MeO)$_2$(Me)Si—CH$_2$—C(H)Me-CH$_2$—S—SiMe$_3$, (EtO)$_2$(Me)Si—CH$_2$—C(H)Me-CH$_2$—S—SiMe$_3$, (PrO)$_2$(Me)Si—CH$_2$—C(H)Me-CH$_2$—S—SiMe$_3$, (BuO)$_2$(Me)Si—CH$_2$—C(H)Me-CH$_2$—S—SiMe$_3$, (MeO) (Me)$_2$Si—(CH$_2$)$_3$—S—SiMe$_3$, (EtO) (Me)$_2$Si—(CH$_2$)$_3$—S—SiMe$_3$, (PrO) (Me)$_2$Si—(CH$_2$)$_3$—S—SiMe$_3$, (BuO) (Me)$_2$Si—(CH$_2$)$_3$—S—SiMe$_3$, (MeO) (Me)$_2$Si—(CH$_2$)$_2$—S—SiMe$_3$, (EtO) (Me)$_2$Si—(CH$_2$)$_2$—S—SiMe$_3$, (PrO) (Me)$_2$Si—(CH$_2$)$_2$—S—SiMe$_3$, (BuO) (Me)$_2$Si—(CH$_2$)$_2$—S—SiMe$_3$, (MeO) (Me)$_2$Si—CH$_2$—S—SiMe$_3$, (EtO) (Me)$_2$Si—CH$_2$—S—SiMe$_3$, (PrO) (Me)$_2$Si—CH$_2$—S—SiMe$_3$, (BuO) (Me)$_2$Si—CH$_2$—S—SiMe$_3$, (MeO) (Me)$_2$Si—CH$_2$—CMe$_2$-CH$_2$—S—SiMe$_3$, (EtO) (Me)$_2$Si—CH$_2$—CMe$_2$-CH$_2$—S—SiMe$_3$, (PrO) (Me)$_2$Si—CH$_2$—CMe$_2$-CH$_2$—S—SiMe$_3$, (BuO) (Me)$_2$Si—CH$_2$—CMe$_2$-CH$_2$—S—SiMe$_3$, ((MeO) (Me)$_2$Si—CH$_2$—C(H)Me-CH$_2$—S—SiMe$_3$, (EtO) (Me)$_2$Si—CH$_2$—C(H)Me-CH$_2$—S—SiMe$_3$, (PrO) (Me)$_2$Si—CH$_2$—C(H)Me-CH$_2$—S—SiMe$_3$, (BuO) (Me)$_2$Si—CH$_2$—C(H)Me-CH$_2$—S—SiMe$_3$, (MeO)$_3$Si—(CH$_2$)$_3$—S—SiEt$_3$, (EtO)$_3$Si—(CH$_2$)$_3$—S—SiEt$_3$, (PrO)$_3$Si—(CH$_2$)$_3$—S—SiEt$_3$, (BuO)$_3$Si—(CH$_2$)$_3$—S—SiEt$_3$, (MeO)$_3$Si—(CH$_2$)$_2$—S—SiEt$_3$, (EtO)$_3$Si—(CH$_2$)$_2$—S—SiEt$_3$, (PrO)$_3$Si—(CH$_2$)$_2$—S—SiEt$_3$, (BuO)$_3$Si—(CH$_2$)$_2$—S—SiEt$_3$, (MeO)$_3$Si—CH$_2$—S—SiEt$_3$, (EtO)$_3$Si—CH$_2$—S—SiEt$_3$, (PrO)$_3$Si—CH$_2$—S—SiEt$_3$, (BuO)$_3$Si—CH$_2$—S—SiEt$_3$, (MeO)$_3$Si—CH$_2$—CMe$_2$-CH$_2$—S—SiEt$_3$, (EtO)$_3$Si—CH$_2$—CMe$_2$-CH$_2$—S—SiEt$_3$, (PrO)$_3$Si—CH$_2$—CMe$_2$-CH$_2$—S—SiEt$_3$, (BuO)$_3$Si—CH$_2$—CMe$_2$-CH$_2$—S—SiEt$_3$, ((MeO)$_3$Si—CH$_2$—C(H)Me-CH$_2$—S—SiEt$_3$, (EtO)$_3$Si—CH$_2$—C(H)Me-CH$_2$—S—SiEt$_3$, (PrO)$_3$Si—CH$_2$—C(H)Me-CH$_2$—S—SiEt$_3$, (BuO)$_3$Si—CH$_2$—C(H)Me-CH$_2$—S—SiEt$_3$, (MeO)$_2$(Me)Si—(CH$_2$)$_3$—S—SiEt$_3$, (EtO)$_2$(Me)Si—(CH$_2$)$_3$—S—SiEt$_3$, (PrO)$_2$(Me)Si—(CH$_2$)$_3$—S—SiEt$_3$, (BuO)$_2$(Me)Si—(CH$_2$)$_3$—S—SiEt$_3$, (MeO)$_2$(Me)Si—(CH$_2$)$_2$—S—SiEt$_3$, (EtO)$_2$(Me)Si—(CH$_2$)$_2$—S—SiEt$_3$, (PrO)$_2$(Me)Si—(CH$_2$)$_2$—S—SiEt$_3$, (BuO)$_2$(Me)Si—(CH$_2$)$_2$—S—SiEt$_3$, (MeO)$_2$(Me)Si—CH$_2$—S—SiEt$_3$, (EtO)$_2$(Me)Si—CH$_2$—S—SiEt$_3$, (PrO)$_2$(Me)Si—CH$_2$—S—SiEt$_3$, (BuO)$_2$(Me)Si—CH$_2$—S—SiEt$_3$, (MeO)$_2$(Me)Si—CH$_2$—CMe$_2$-CH$_2$—S—SiEt$_3$, (EtO)$_2$(Me)Si—CH$_2$—CMe$_2$-CH$_2$—S—SiEt$_3$, (PrO)$_2$(Me)Si—CH$_2$—CMe$_2$-CH$_2$—S—SiEt$_3$, (BuO)$_2$(Me)Si—CH$_2$—CMe$_2$-CH$_2$—S—SiEt$_3$, ((MeO)$_2$(Me)Si—CH$_2$—C(H)Me-CH$_2$—S—SiEt$_3$, (EtO)$_2$(Me)Si—CH$_2$—C(H)Me-CH$_2$—S—SiEt$_3$, (PrO)$_2$(Me)Si—CH$_2$—C(H)Me-CH$_2$—S—SiEt$_3$, (BuO)$_2$(Me)Si—CH$_2$—C(H)Me-CH$_2$—S—SiEt$_3$, (MeO) (Me)$_2$Si—(CH$_2$)$_3$—S—SiEt$_3$, (EtO) (Me)$_2$Si—(CH$_2$)$_3$—S—SiEt$_3$, (PrO) (Me)$_2$Si—(CH$_2$)$_3$—S—SiEt$_3$, (BuO) (Me)$_2$Si—(CH$_2$)$_3$—S—SiEt$_3$, (MeO) (Me)$_2$Si—(CH$_2$)$_2$—S—SiEt$_3$, (EtO) (Me)$_2$Si—(CH$_2$)$_2$—S—SiEt$_3$, (PrO) (Me)$_2$Si—(CH$_2$)$_2$—S—SiEt$_3$, (BuO) (Me)$_2$Si—(CH$_2$)$_2$—S—SiEt$_3$, (MeO) (Me)$_2$Si—CH$_2$—S—SiEt$_3$, (EtO) (Me)$_2$Si—CH$_2$—S—SiEt$_3$, (PrO) (Me)$_2$Si—CH$_2$—S—SiEt$_3$, (BuO) (Me)$_2$Si—CH$_2$—S—SiEt$_3$, (MeO) (Me)$_2$Si—CH$_2$—CMe$_2$-CH$_2$—S—SiEt$_3$, (EtO) (Me)$_2$Si—CH$_2$—CMe$_2$-CH$_2$—S—SiEt$_3$, (PrO) (Me)$_2$Si—CH$_2$—CMe$_2$-CH$_2$—S—SiEt$_3$, (BuO) (Me)$_2$Si—CH$_2$—CMe$_2$-CH$_2$—S—SiEt$_3$, ((MeO) (Me)$_2$Si—CH$_2$—C(H)Me-CH$_2$—S—SiEt$_3$, (EtO) (Me)$_2$Si—CH$_2$—C(H)Me-CH$_2$—S—SiEt$_3$, (PrO) (Me)$_2$Si—CH$_2$—C(H)Me-CH$_2$—S—SiEt$_3$, and (BuO) (Me)$_2$Si—CH$_2$—C(H)Me-CH$_2$—S—SiEt$_3$.

The chain end-modifying compound of Formula 8 may be prepared as described in WO 2007/047943 and WO 2009/148932.

The compounds of Formula 7 and 8 also include their corresponding Lewis base adducts (for example with solvent molecules tetrahydrofuran, diethylether, dimethoxyethane coordinated with silicon atoms).

The chain end-modifying compounds include the sulfanylsilane compounds described in U.S. Pat. No. 6,229,036, WO 2007/047943 and WO 2009/148932 (each are fully incorporated herein by reference, including the methods for preparing sulfanylsilane compounds).

The chain end-modifying compounds may be added intermittently (or at regular or irregular intervals) or continuously during the polymerization, but are preferably added at a conversion rate of the polymerization of more than 80 percent, and more preferably at a conversion rate of more than 90 percent. Preferably, a substantial amount of the polymer chain ends is not terminated prior to the reaction with the chain end-modifying compound; that is, the living polymer chain ends are present, and capable of reacting with the chain end-modifying compound. The chain end modification reaction may occur before, after or during the addition of the coupling agent. Preferably the chain end modification reaction is completed after the addition of the coupling agent. See, for example, WO 2009/148932, incorporated herein by reference.

In one embodiment, more than 20 percent, preferably more than 35 percent, and even more preferably more than 50 percent of the polymer chains, as determined by GPC, formed in the course of the polymerization process, are linked with a chain end-modifying compound in the process of polymer chain end modification.

In one embodiment, more than 20 percent of the polymer chain ends, as determined by GPC, are reacted with coupling agent(s), prior to the addition of the chain end-modifying compound(s). In yet other embodiments, more than 35 percent of the polymer chain ends are reacted with coupling agent(s), prior to the addition of the chain end-modifying compound(s).

In one embodiment, between 20 and 35 percent of the living polymer chain ends, as determined by GPC, are reacted with coupling agent(s), prior to the addition of chain end-modifying compound(s). In other embodiments, between 35 and 50 percent of the living polymer chain ends, as determined by GPC, are reacted with coupling agent(s), prior to the addition of chain end-modifying compound(s). In yet other embodiment, between 50 and 80 percent of the living polymer chain ends are reacted with coupling agent(s), prior to the addition of chain end-modifying compound(s).

In one embodiment, more than 50 percent, preferably more than 60 percent, and more preferably more than 75 percent, as determined by GPC, of the alpha-modified living macromolecular compounds (still remaining after the coupling reaction) react with an end-modification agent. A chain end-modified macromolecular compound according to the invention comprises a functionality derived from an amine polymerization initiator compound and a functionality derived from the chain end-modifying compound.

Process of Chain End Modification

The chain end-modifying compound may be directly added to the polymer solution without dilution; however, it may be beneficial to add the compound in dissolved form, such as in an inert solvent (e.g. cyclohexane). The amount of chain end-modifying compound added to the polymerization varies, depending upon the monomer species, coupling agent, chain end-modifying compound, reaction conditions, and desired end properties, but is generally from 0.05 to 5 mol-equivalent, preferably from 0.1 to 2.0 mol-equivalent, and most preferably from 0.2 to 1.5 mol-equivalent, per mol equivalent of alkali metal in the initiator compound. The polymer chain end modification reaction may be carried out in a temperature range of from 0° C. to 150° C., preferably of from 15° C. to 120° C., and even more preferably of from 40° C. to 100° C. There is no limitation for the duration of the chain end modification reaction. However, with respect to an economical polymerization process, for example, in the case of a batch polymerization process, the chain end modification reaction is usually stopped at about 5 to 60 minutes after the addition of the modifier.

The method for making the modified macromolecular compound in accordance with the present invention comprises at least the following step (i) and optionally steps (ii) and/or (iii). Step (i): reacting the amino silane polymerization initiator compound as represented by Formulas 4, 4a, 4b, 4c, 5, 5a, 5b or 5c (each formula as described above), and preferably by Formula 4a or 5a, wherein $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ are each independently selected from ($C_1$-$C_{18}$) alkyl and wherein q is 1 and r is 2, with one or more monomer types, and preferably monomers selected from butadiene, styrene, isoprene, alpha methyl-styrene and combinations thereof, in a polymerization solvent to form a Composition A. Suitable polymerization solvents include non-polar aliphatic and non-polar aromatic solvents, preferably hexane, heptane, butane, pentane, isopar, cyclohexane, toluene and benzene. Optional step (iia): reacting Composition A with at least one type of coupling agent selected from the group consisting of the following: $SnCl_4$, $(R_1)_3SnCl$, $(R_1)_2SnCl_2$, $R_1SnCl_3$, $SiCl_4$, $(R_1)_3SiCl$, $(R_1)_2SiCl_2$, $R_1SiCl_3$, $Cl_3Si$—$SiCl_3$, $Cl_3Si$—O—$SiCl_3$, $Cl_3Sn$—$SnCl_3$, $Cl_3Sn$—O—$SnCl_3$. $Sn(OMe)_4$, $Si(OMe)_4$, $Sn(OEt)_4$ and $Si(OEt)_4$. Optional step (ii): reacting the resulting polymer, i.e. one of the Compositions A and B, with at least one type of chain end-modifying compound of Formula 6, including compounds of Formula 7 and Formula 8, to form the chain end-modified polymer, i.e. the modified macromolecular compound. In optional step (iii), the polymerization reaction is terminated by addition of a protonating agent. As a protonating agent in the present invention, one or more compounds capable of transferring a proton to and thus deactivating the living polymer chain end can be used, such as water, organic acids (e.g., carboxylic acids), inorganic acids (e.g., hydrochloric acid, sulfuric acid), and alcohols (e.g. methanol). Preferably, methanol is used as the protonating agent. The protonating agent additionally renders metal organic residues derived from the polymerization initiator compound, from chain end modifier compounds or from metallated polymer chain ends less reactive and thus less dangerous.

In a preferred embodiment, the amino silane polymerization initiator compound is reacted first with monomers to form alpha-modified living polymers (step (i)). Some of these macromolecular compounds are optionally reacted with coupling agent(s) to form branched modified macromolecular compound(s) (optional step (iia)). In step (ii), some or all of the alpha-modified living polymers are reacted with the chain end-modifying compound to form linear modified macromolecular compounds.

In one embodiment, the amino silane polymerization initiator compound is the compound of Formula 4a, 4b or 4c.

In one embodiment, the amino silane polymerization initiator compound is the compound of Formula 5a, 5b or 5c.

In one embodiment, the amino silane polymerization initiator compound is the compound of Formula 4a or 5a.

In another embodiment, the coupling agent is selected from the following: $SnCl_4$, $(R_1)_3SnCl$, $(R_1)_2SnCl_2$, $R_1SnCl_3$, $SiCl_4$, $(R_1)_3SiCl$, $(R_1)_2SiCl_2$, $R_1SiCl_3$, $Cl_3Si$—$SiCl_3$, $Cl_3Si$—O—$SiCl_3$, $Cl_3Sn$—$SnCl_3$, $Cl_3Sn$—O—$SnCl_3$ and combinations thereof. Examples of tin and silicon alkoxide coupling agents include: $Sn(OMe)_4$, $Si(OMe)_4$, $Sn(OEt)_4$ and $Si(OEt)_4$.

In a further embodiment, the chain end-modifying compound is the compound of Formula 7, wherein $M^1$ is a silicon atom; $R^2$, $R^7$, $R^8$ and $R^9$ are each independently selected from $(C_1-C_{18})$ alkyl and Y is divalent and is $(C_1-C_{18})$ alkyl.

In a further embodiment, the chain end-modifying compound is the compound of Formula 7, wherein $M^1$ is a tin atom; $R^2$, $R^7$, $R^8$ and $R^9$ are each independently selected from $(C_1-C_{18})$ alkyl and Y is divalent and is $(C_1-C_{18})$ alkyl.

In a further embodiment, the chain end-modifying compound is the compound of Formula 8, wherein $M^1$ is a silicon atom; $R^2$, $R^7$, $R^8$ and $R^{11}$ are each independently selected from $(C_1-C_{18})$ alkyl and Y is divalent and is $(C_1-C_{18})$ alkyl.

In a further embodiment, the chain end-modifying compound is the compound of Formula 8, wherein $M^1$ is a tin atom; $R^2$, $R^7$, $R^8$ and $R^{11}$ are each independently selected from $(C_1-C_{18})$ alkyl and Y is divalent and is $(C_1-C_{18})$ alkyl.

Monomers

As described above, the elastomeric diene polymer chain P comprises monomer units derived from at least one of butadiene, isoprene, styrene and alpha-methylstyrene. Nevertheless, monomers useful in preparing the modified macromolecular compounds generally include conjugated olefins and olefins selected from α-olefins, internal olefins, cyclic olefins, polar olefins and nonconjugated diolefins, and the elastomeric diene polymer chain P may comprise monomer units derived from such monomers. Such monomers may also result in further modified or non-modified polymers which may thus be present in the first and second polymer compositions of the present invention. Suitable conjugated unsaturated monomers are preferably conjugated dienes, such as 1,3-butadiene, 2-alkyl-1,3-butadiene, preferably, isoprene (2-methyl-1,3-butadiene), 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene, 1,3-cyclooctadiene. Preferred olefins are $C_{2-20}$ α-olefins, including, but not limited to, long chain macromolecular α-olefins, more especially an aromatic vinyl compound. Preferred aromatic vinyl compounds are styrene, including $C_{1-4}$ alkyl substituted styrene, such as 2-methylstyrene, 3-methylstyrene, 4-methylstyrene, 2,4-dimethylstyrene, 2,4,6-trimethylstyrene, α-methylstyrene and stilbene, 2,4-diisopropylstyrene, 4-tert-butylstyrene, vinyl benzyl dimethylamine, (4-vinylbenzyl)dimethyl aminoethyl ether, N,N-dimethylaminoethyl styrene, tert-butoxystyrene, vinylpyridine, and mixtures thereof. Suitable polar olefins included acrylonitrile, methacrylates, methylmethacrylate. Suitable nonconjugated olefins include $C_{4-20}$ diolefins, especially norbornadiene, ethylidenenorbornene, 1,4-hexadiene, 1,5-hexadiene, 1,7-octadiene, 4-vinylcyclohexene, divinylbenzene including 1,2-divinylbenzene, 1,3-divinylbenzene and 1,4-divinylbenzene and mixtures thereof. Preferred conjugated dienes include butadiene, isoprene and cyclopentadiene, and preferred aromatic α-olefins include: styrene and 4-methylstyrene.

Polymerization

General information about the polymerization technologies including polymerization initiator compounds; polar coordinator compounds and accelerators, each to increase the reactivity of the initiator, to randomly arrange aromatic vinyl compounds, to randomly arrange 1,2-polybutadiene or 1,2-polyisoprene or 3,4-polyisoprene units introduced in the polymer chain; the amounts of each compound; monomer(s); and suitable process conditions are described in WO 2009/148932 fully incorporated herein by reference. Solution polymerizations normally take place at lower pressures, preferably below 10 MPa, preferably in a temperature range of from 0 to 120° C. The polymerization is generally conducted in batchwise, continuous or semi-continuous polymerization conditions. The polymerization process is preferably conducted as a solution polymerization, wherein the polymer formed is substantially soluble in the reaction mixture, or as a suspension/slurry polymerization, wherein the polymer formed is substantially insoluble in the reaction medium. Examples of preferred polar coordinator compounds and of accelerators are listed in WO 2009/148932.

Modified Macromolecular Compounds

Exemplary modified macromolecular compounds (i.e. alpha-modified/omega-modified macromolecular compounds) are represented by the following Formulas P1 to P6 and Lewis base adducts thereof:

(Formula P1)

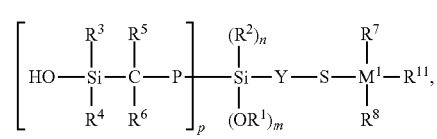

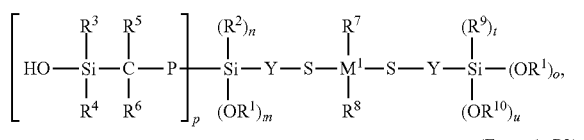
(Formula P2)

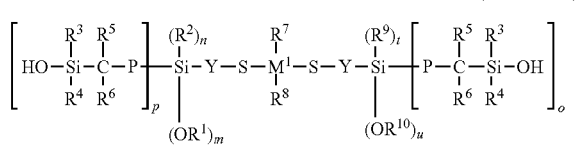
(Formula P3)

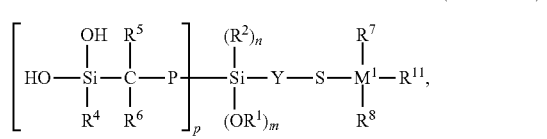
(Formula P4)

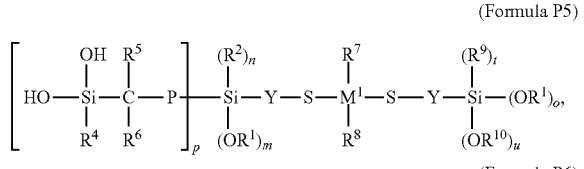
(Formula P5)

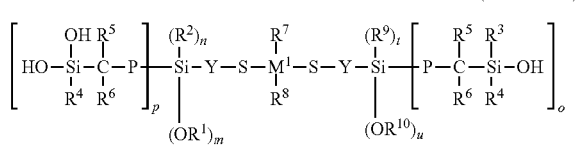
(Formula P6)

In the above formulas, P is a polymer chain comprising monomer units derived from at least one of the following monomer groups: butadiene, isoprene, styrene and alpha-methylstyrene, the number of monomer units per macromolecule ranging from usually 10 to 50.000, preferably from 20 to 40.000; and the substituent groups are as generally defined for Formula 1 above.

In one preferred embodiment, $M^1$ is a tin atom; Y is divalent and is $(C_1$-$C_{18})$ alkyl; $R^5$ and $R^6$ are each independently selected from hydrogen and $(C_1$-$C_{18})$ alkyl; and $R^7$ and $R^8$ are each independently selected from $(C_1$-$C_{18})$ alkyl; and $R^3$ and $R^4$ are each independently selected from —OH and $(C_1$-$C_{18})$ alkyl; p and o are each independently selected from an integer of 1 and 2; m and u are each independently selected from an integer of 1 and 2; n and t are each independently selected from an integer of 0 and 1.

In one preferred embodiment, $M^1$ is a silicon atom; Y is divalent and is $(C_1$-$C_{18})$ alkyl; $R^5$ and $R^6$ are each independently selected from hydrogen and $(C_1$-$C_{18})$ alkyl and; $R^7$ and $R^8$ are each independently selected from $(C_1$-$C_{18})$ alkyl; and $R^3$ and $R^4$ are each independently selected from —OH and $(C_1$-$C_{18})$ alkyl; p and o are each independently selected from an integer of 1 and 2; m and u are each independently selected from an integer of 1 and 2; n and t are each independently selected from an integer of 0 and 1.

In one preferred embodiment, $M^1$ is a tin atom; Y is divalent and is $(C_1$-$C_{18})$ alkyl; $R^5$ is hydrogen and $R^6$ is selected from hydrogen and $(C_1$-$C_{18})$ alkyl; and $R^3$, $R^4$, $R^7$ and RB are each independently selected from $(C_1$-$C_{18})$ alkyl; and p and o are each independently selected from an integer of 1 and 2; m and u are each independently selected from an integer of 1 and 2; n and t are each independently selected from an integer of 0 and 1.

In one preferred embodiment, $M^1$ is a silicon atom; Y is divalent and is $(C_1$-$C_{18})$ alkyl; $R^5$ is hydrogen and $R^6$ is selected from hydrogen and $(C_1$-$C_{18})$ alkyl; and $R^3$, $R^4$, $R^7$ and $R^8$ are each independently selected from $(C_1$-$C_{18})$ alkyl; and p and o are each independently selected from an integer of 1 and 2; m and u are each independently selected from an integer of 1 and 2; n and t are each independently selected from an integer of 0 and 1.

From the above listed Formulas P1 to P6, the Formulas P1, P2 and P3 are preferred.

Specific preferred modified macromolecular compounds include the following ones (and their corresponding Lewis base adducts):

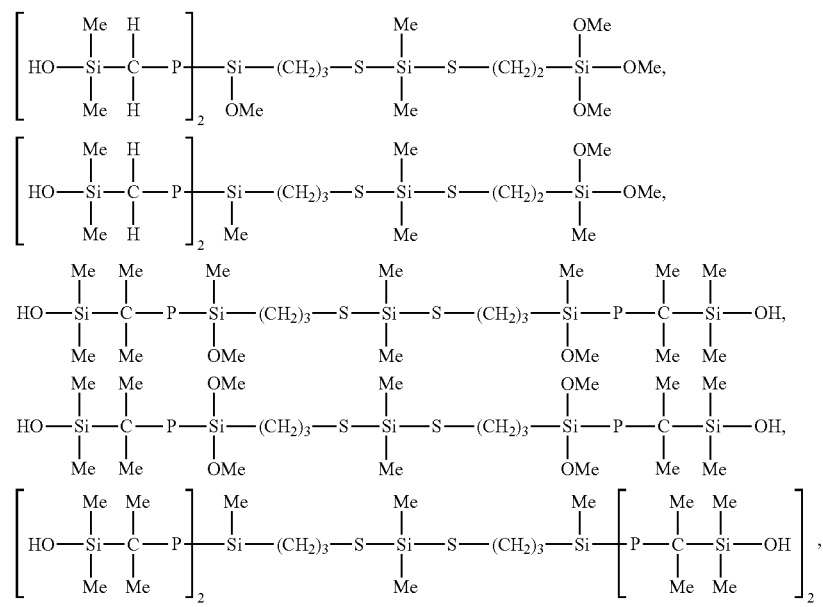

-continued

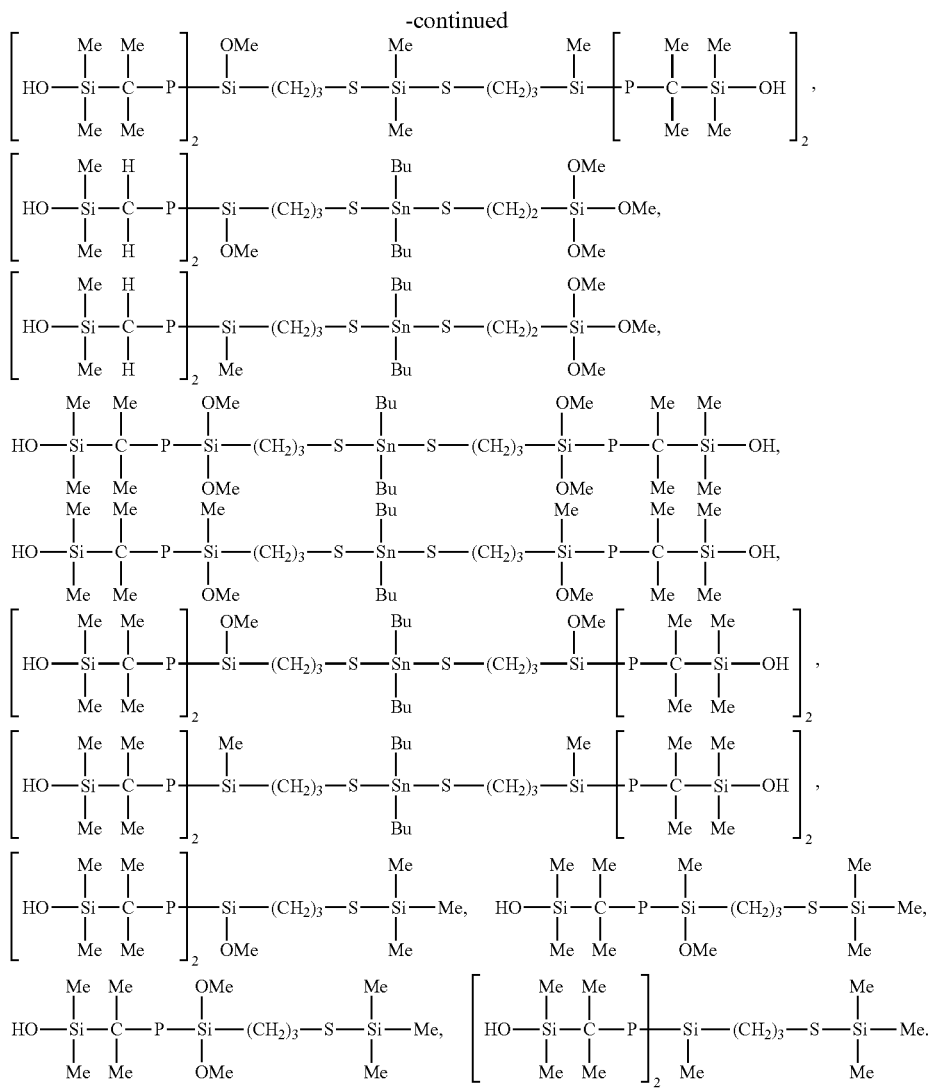

While not wishing to be bound by theory, the trihydrocarbylsilyl, including trialkylsilyl, triaralkylsilyl and triarylsilyl; trihydrocarbylstannyl, including trialkylstannyl, triaralkylstannyl and triarylstannyl; dihydrocarbylsilendiyl, including dialkylsilendeyl, diaralkylsilendiyl and diarylsilendiyl; dihydrocarbylstannendiyl, including dialkylstannendiyl, diaralkylstannendiyl and diarylstannendiyl groups in Formulas P1, P2, P3, P4, P5 and P6 are each believed to function as a protective group, which prevents unintended subsequent reaction. These "protective" groups, ($-Si'R^7R^8R^{11}$), ($-Sn'R^7R^8R^{11}$), ($-Si'R^7R^8-$) and ($-Sn'R^7R^8-$), may be removed by exposure to a compound containing $-OH$ groups, such as water, alcohols, anionic acids or organic acids (for example hydrochloric acid, sulfuric acid or carboxylic acids), thus forming an "un-protected" thiol ($-SH$) group. Such conditions are typically present during vulcanization. Depending on the polymer "work up" conditions, both the unprotected and/or protected modified polymers may be present. For example, steam stripping of a polymer solution containing the modified macromolecule of Formula P1, P2, P3, P4, P5 and P6 will remove a certain percentage of the protecting trihydrocarbyl groups, including trialkyl, triaralkyl, or triarylsilyl groups, resulting in the unprotected thiol ($-SH$) group and forming a certain percentage of compounds of Formula P7 (including Lewis base adducts):

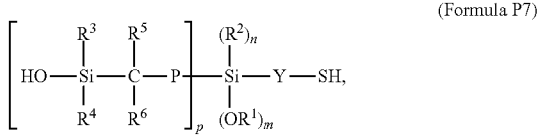

(Formula P7)

wherein the substituent groups are as generally defined for Formula 1 above and the number of monomer units per macromolecule ranges from usually 10 to 50,000 g/mol, preferably from 20 to 40,000 g/mol.

In one preferred embodiment, Y is divalent and is ($C_1$-$C_{18}$) alkyl; $R^5$ and $R^6$ are each independently selected from hydrogen and ($C_1$-$C_{18}$) alkyl; and $R^3$ and $R^4$ are each independently selected from $-OH$ and ($C_1$-$C_{18}$) alkyl; p is selected from an integer of 1 and 2; m is selected from an integer of 1 and 2; n is selected from an integer of 0 and 1.

In one preferred embodiment, Y is divalent and is ($C_1$-$C_{18}$) alkyl; $R^5$ is selected from hydrogen and $R^6$ is selected from hydrogen and ($C_1$-$C_{18}$) alkyl; and $R^3$ and $R^4$ are each independently selected from ($C_1$-$C_{18}$) alkyl; and p is selected from an integer of 1 and 2; m is selected from an integer of 1 and 2; n is selected from an integer of 0 and 1.

The percentage of thiol groups can be very different, depending on to the structure of the R-group in the (—Si'$R^7R^8R^{11}$), (—Sn'$R^7R^8R^{11}$), (—Si'$R^7R^8$—) and (—Sn'$R^7R^8$—) moieties of the macromolecular compound of Formula 1, Embodiments 1 and 2 and Formulas P1 to P6. Alternatively, a water-free work up procedure can be used for the preparation of the modified macromolecular compounds.

Specific preferred modified macromolecular compounds based on Formula 7 include the following ones (and their corresponding Lewis base adducts):

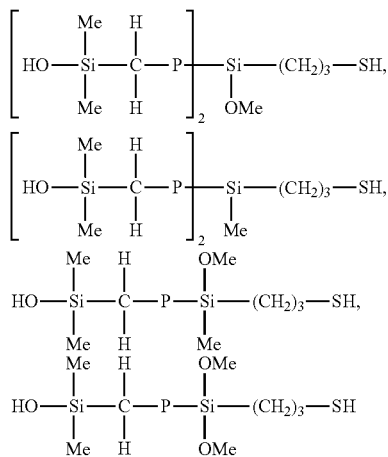

The resulting alpha-modified macromolecular compound comprises one or more silanol groups, typically in a total amount from 0.0001 to 1.50 mmol/gram of polymer (total amount of polymer obtained in the polymerization reaction), preferably from 0.0005 to 0.9 mmol/gram, and more preferably from 0.0010 to 0.5 mmol/gram, and even more preferably from 0.0020 to 0.1 mmol/gram of polymer.

The resulting alpha-modified macromolecular compound preferably comprises sulfide groups, and the sulfide groups typically comprise trihydrocarbylsilyl or dihydrocarbyl protective groups and thiol groups in a total amount of from 0.0001 to 0.50 mmol/gram of polymer (total amount of polymer obtained in the polymerization reaction), preferably from 0.0005 to 0.30 mmol/gram, and more preferably from 0.0010 to 0.20 mmol/gram, and even more preferably from 0.0020 to 0.10 mmol/gram of polymer. In another embodiment, the sulfide groups are present in an amount ranging from 0.0001 to 0.50 mmol/gram of polymer, preferably ranging from 0.0005 to 0.30 mmol/gram, and more preferably ranging from 0.0010 to 0.20 mmol/gram, and even more preferably from ranging from 0.0020 to 0.10 mmol/gram of polymer. In another embodiment, the thiol groups are present in an amount ranging from 0.0001 to 0.50 mmol/gram of polymer, preferably ranging from 0.0005 to 0.30 mmol/gram, and more preferably ranging from 0.0010 to 0.20 mmol/gram, and even more preferably from ranging from 0.0020 to 0.10 mmol/gram of polymer.

For most applications, the modified macromolecular compound is preferably a homopolymer derived from a conjugated diolefin, a copolymer derived from a conjugated diolefin monomer with an aromatic vinyl monomer, and/or a terpolymer of one or two types of conjugated diolefins with one or two types of aromatic vinyl compounds.

Although there are no specific limitations regarding the content of 1,2-bonds and/or 3,4-bonds (hereinafter called "vinyl bonds") of the conjugation diolefin portion of the elastomeric polymer, for most applications the vinyl bond content is preferably from 10 to 90% by weight and particularly preferably from 15 to 80% by weight (based on the total weight of the polymer obtained in the polymerization reaction). If the vinyl bond content in a polymer is less than 10% by weight, the resulting product may have inferior wet skid resistance. If the vinyl content in the elastomeric polymer exceeds 90% by weight, the product may exhibit compromised tensile strength and abrasion resistance and a relatively large hysteresis loss.

Although there are no specific limitations regarding the amount of aromatic vinyl monomer used in the modified macromolecular compound, in most applications the aromatic vinyl monomers constitute from 5 to 60% by weight of the total monomer content, and more preferably from 10 to 50% by weight (based on the total weight of the polymer). Values of less than 5% by weight may lead to reduced wet skid properties, abrasion resistance, and tensile strength; whereas values of more than 60% by weight may lead to increased hysteresis loss. The modified macromolecular compound may be a block or random copolymer, and preferably 40% by weight or more of the aromatic vinyl compound units are linked singly, and 10% by weight or less are "blocks" in which eight or more aromatic vinyl compounds are linked successively. Copolymers falling outside this range often exhibit increased hysteresis. The length of successively linked aromatic vinyl units can be measured by an ozonolysis-gel permeation chromatography method developed by Tanaka et al. (Polymer, Vol. 22, Pages 1721-1723 (1981)).

While this is dependant on the specific polymer and desired end use, the modified macromolecular compounds of the present invention, in the form as obtained from the polymerization reaction, preferably have a Mooney viscosity (ML 1+4, 100° C., as measured in accordance with ASTM D 1646 (2004) in the range of from 0 to 150, preferably from 0 to 100, and more preferably in the range of from 20 to 100, as determined using a Monsanto MV2000 instrument. If the Mooney viscosity (ML 1+4, 100° C.) of the polymer is more than 150 MU, the processability (filler incorporation and heat build up in the internal mixer, banding on the roll mill, extrusion rate, extrudate die swell, smoothness, etc.) is likely to be negatively affected because the compounding machinery used by the tire manufacturers are not designed to handle such high Mooney rubber grades, and the cost of processing increases. In some cases a Mooney viscosity (ML 1+4, 100° C.) of less than 20 may not be preferred du to increased tack and cold flow of the uncrosslinked elastomeric polymer, resulting in difficult handling, poor green strength and poor dimensional stability during storage. In some further cases, when the modified polymers are used as a softener, compatibilizer or processing aid in polymer formulations, a Mooney viscosity (ML 1+4, 100° C.) of less than 20 may be preferred.

The preferred molecular weight distribution of the modified macromolecular compounds as obtained from the polymerization reaction, represented by the ratio of the weight average molecular weight to the number average molecular weight ($M_w/M_n$), ranges from 1.0 to 10.0, preferably from 1.1 to 8.0 and more preferably from 1.2 to 4.5.

Reactive Compounding

In a preferred embodiment, the first polymer composition, comprising at least one modified macromolecular compound of the invention, is combined and reacted with filler(s) selected from silica, carbon-silica dual phase filler, carbon black, carbon nano-tube filler, lignin, glass filler, layered silicates, such as magadiite, in some preferred embodiments comprising silica as main filler component, and vulcanization agent and, optionally, additional components, including, but not limited to, processing aids, oils, vulcanization agents, silane coupling agents and unmodified uncrosslinked elastomeric polymers, thus forming a second polymer composition comprising filler.

The first polymer composition comprises at least one modified macromolecular compound and optionally one or both of the following (i) oil (resulting in what is often referred to as oil extended polymer) and (ii) polymer which is not identical with the modified macromolecular compounds according to the invention. Polymers which are not identical with modified macromolecular compounds may be by-produced in the process of preparation of the modified macromolecular compound (see above) and may result from blending modified macromolecular compound(s) (for example in the form as obtained after polymerization) in solution with another polymer solution not containing macromolecular compound(s) of the present invention, followed by solvent removal. The first polymer composition preferably comprises at least 20% by weight of the modified macromolecular compound(s) of the invention, more preferably at least 30% by weight and even more preferably at least 45% by weight, based on the total polymer contained in the composition. The remaining portion of the polymer in the polymer composition is unmodified polymer or polymer modified not according to the invention. Examples of preferred unmodified polymers are listed in WO 2009/148932 and preferably include styrene-butadiene copolymer, natural rubbers, polyisoprene and polybutadiene. It is desirable that the unmodified polymers have a Mooney viscosity (ML 1 5+4, 100° C. as measured in accordance with ASTM D 1646 (2004), as discussed above) in the range of from 20 to 200, preferably from 25 to 150.

Oils

Oils may be used in combination with the uncrosslinked modified macromolecular compounds to reduce viscosity or Mooney values, or to improve processability of the first polymer compositions and performance properties of (vulcanized) second polymer compositions.

One or more oils can be added to the polymer prior to the end of the preparation process for the modified macromolecular compound and/or as a separate component of the first or second polymer composition. For representative examples and classification of the oils see WO 2009/148932 and U.S. 2005/0159513, each of which is incorporated herein by reference in its entirety.

Representative oils include but are not limited to MES (Mild Extraction Solvate), TDAE (Treated Distillate Aromatic Extract), RAE (Residual Aromatic Extract) including but not limited to T-RAE and S-RAE, DAE including T-DAE and NAP (light and heavy naphthenic oils), including but not limited to Nytex 4700, Nytex 8450, Nytex 5450, Nytex 832, Tufflo 2000, and Tufflo 1200. In addition, native oils, including but not limited to vegetable oils, can be used as extender oils. Representative oils also include functionalized variations of the aforementioned oils, particularly epoxidized or hydroxylated oils. The aforementioned oils comprise varying concentrations of polycyclic aromatic compounds, paraffinics, naphthenics and aromatics and have different glass transition temperatures. The above mentioned types of oils have been characterized (*Kautschuk Gummi Kunststoffe*, vol. 52, pages 799-805). In some embodiments, the MES, RAE and TDAE are extender oils for rubber.

Processing Aids

Processing aids can optionally be added to the first polymer compositions of the present invention. Processing aids are usually added to reduce the first polymer composition viscosity. As a result, the mixing period is decreased and/or the number of mixing steps is reduced and, consequently, less energy is consumed and/or a higher throughput in the course of the rubber compound extrusion process is achieved. Representative processing aids which can optionally be used as a component in the first polymer compositions in accordance with the present teachings are described in *Rubber Handbook, SGF, The Swedish Institution of Rubber Technology* 2000 and in Werner Kleemann, Kurt Weber, *Elastverarbeitung-Kennwerte und Berechnungsmethoden*, Deutscher Verlag für Grundstoffindustrie (Leipzig, 1990), each of which is incorporated herein by reference in its entirety. Representative possessing aids which can optionally be used as component in the first polymer composition are as follows:

(A) fatty acids including but not limited to oleic acid, priolene, pristerene and stearic acid;

(B) fatty acid salts including but not limited to Aktiplast GT, PP, ST, T, T-60, 8, F; Deoflow S; Kettlitz Dispergator FL, FL Plus; Dispergum 18, C, E, K, L, N, T, R; Polyplastol 6, 15, 19, 21, 23; Struktol A50P, A60, EF44, EF66, EM16, EM50, WA48, WB16, WB42, WS180, WS280 and ZEHDL;

(C) dispersing agents and processing aids including but not limited to Aflux 12, 16, 42, 54, 25; Deoflow A, D; Deogum 80; Deosol H; Kettlitz Dispergator DS, KB, OX; Kettlitz-Mediaplast 40, 50, Pertac/GR; Kettlitz-Dispergator SI; Struktol FL and WB 212; and (D) dispersing agents for highly active white fillers including but not limited to Struktol W33 and WB42.

Bifunctionalized silanes and monofunctional silanes (herein also called "silane coupling agents") are also occasionally referred to as processing aids but are separately described below.

Silane Coupling Agents

In some embodiments, a silane coupling agent (used for compatibilization of polymer and indicated fillers) is added to the composition which contains the modified macromolecular compound as described herein and silica, layered silicate (such as but not limited to magadiite) or carbon-silica dual-phase filler, which may be used as filler component. The typical amount of a silane coupling agent is from about 1 to about 20 parts by weight and, in some embodiments, from about 5 to about 15 parts by weight for 100 parts by weight of the total amount of silica and/or carbon-silica dual-phase filler.

Silane coupling agents can be classified according to *Fritz Röthemeyer, Franz Sommer: Kautschuk Technologie*, (Carl Hanser Verlag 2006):

(A) bifunctionalized silanes including but not limited to Si 230 $(EtO)_3Si(CH_2)_3Cl$, Si 225 $(EtO)_3SiCH=CH_2$, A189 $(EtO)_3Si(CH_2)_3SH$, Si 69 $[(EtO)_3Si(CH_2)_3S_2]2$, Si 264 $(EtO)_3Si-(CH_2)_3SCN$ and Si 363 $(EtO)Si((CH_2-CH_2-O)_5(CH_2)_{12}CH_3)_2(CH_2)_3SH)$ (Evonic Industries AG); and (B) monofunctional silanes including but not limited to Si 203 $(EtO)_3-Si-C_3H_7$, and Si 208 $(EtO)_3-Si-C_8H_{17}$.

Further examples of silane coupling agents are given in WO 2009/148932 and include but are not limited to bis-(3-hydroxy-dimethylsilyl-propyl)tetrasulfide, bis-(3-hydroxy-dimethylsilyl-propyl)-disulfide, bis-(2-hydroxy-dimethylsilyl-ethyl)tetrasulfide, bis-(2-hydroxy-dimethylsilyl-ethyl)disulfide, 3-hydroxy-dimethylsilyl-propyl-N,N-dimethylthiocarbamoyl-tetrasulfide and 3-hydroxy-dimethylsilyl-propylbenzothiazole tetrasulfide.

Vulcanization Agents

Sulfur, sulfur-containing compounds acting as sulfur-donors, sulfur-accelerator systems and peroxides are the most common vulcanizing agents. Examples of sulfur-containing compounds acting as sulfur-donors include but are not limited to dithiodimorpholine (DTDM), tetramethylthiuramdisulphide (TMTD), tetraethylthiuramdisulphide (TETD), and dipentamethylenthiuramtetrasulphide (DPTT). Examples of sulfur accelerators include but are not limited to amine derivates, guanidine derivates, aldehydeamine condensation products, thiazoles, thiuram sulphides, dithiocarbamates and thiophosphates. Examples of peroxides used as vulcanizing agents include but are not limited to di-tert.-butyl-peroxides, di-(tert.-butyl-peroxy-trimethyl-cyclohexane), di-(tert.-butyl-peroxy-isopropyl-)benzene, dichloro-benzoylperoxide, dicumylperoxides, tert.-butyl-cumyl-peroxide, dimethyl-di(tert.-butyl-peroxy)hexane, dimethyl-di(tert.-butyl-peroxy)hexine and butyl-di(tert.-butyl-peroxy)valerate (*Rubber Handbook, SGF, The Swedish Institution of Rubber Technology* 2000).

Further examples and additional information regarding vulcanizing agents can be found in Kirk-Othmer, *Encyclopedia of Chemical technology* 3$^{rd}$, Ed., (Wiley Interscience, N. Y. 1982), volume 20, pp. 365-468, (specifically "Vulcanizing Agents and Auxiliary Materials" pp. 390-402).

A vulcanizing accelerator of the sulfene amide-type, guanidine-type, or thiuram-type can be used together with a vulcanizing agent as required. Other additives such as zinc white, vulcanization auxiliaries, aging preventives, processing adjuvants and the like may optionally be added. A vulcanizing agent is typically added to the polymer composition in an amount of from 0.5 to 10 parts by weight and, in some embodiments, from 1 to 6 parts by weight per 100 parts by weight of the total elastomeric polymer. Examples of vulcanizing accelerators and the amount of accelerator added with respect to the total polymer are given in WO 2009/148932. Sulfur-accelerator systems may or may not comprise zinc oxide. Preferably zinc oxide is used as a component of the sulfur-accelerator system.

Fillers

The second polymer composition of the present invention includes at least one filler, which serves as a reinforcement agent. Carbon black, silica, carbon-silica dual-phase filler, clay (layered silicates), calcium carbonate, magnesium carbonate, lignin, carbon nano tubes, amorphous fillers, such as glass particle based fillers, starch based fillers and the like and combinations thereof are examples of suitable fillers. Examples of fillers are described in WO 2009/148932 which is fully incorporated herein by reference. In some embodiments, the combined use of carbon black and silica, the use of carbon-silica dual-phase-fillers alone or the combined use of carbon-silica dual-phase-filler and carbon black and/or silica are employed. Carbon black is manufactured by a furnace method, and in some embodiments a nitrogen adsorption specific surface area of 50-200 m$^2$/g and DBP oil absorption of 80-200 ml/100 grams, for example, FEF; HAF, ISAF, or SAF class carbon black, is used. In some embodiments, high agglomeration type carbon black is used. Carbon black is typically added in an amount of from 2 to 100 parts by weight, in some embodiments from 5 to 100 parts by weight, in some embodiments from 10 to 100 parts by weight, and in some embodiments from 10 to 95 parts by weight per 100 parts by weight of the total elastomeric polymer.

Examples of silica fillers include but are not limited to wet process silica, dry process silica, synthetic silicate-type silica and combinations thereof. Silica with a small particle diameter and high surface area exhibits a high reinforcing effect. Small diameter, high agglomeration-type silica (i.e., having a large surface area and high oil absorptivity) exhibits excellent dispersibility in the elastomeric polymer composition, representing desirable properties and superior processability. An average particle diameter of silica, in terms of a primary particle diameter, is in some embodiments from 5 to 60 nm, and in some embodiments from 10 to 35 nm. Moreover, the specific surface area of the silica particles (measured by the BET method) is in some embodiments from 35 to 300 m$^2$/g. For examples of silica filler diameters, particle sizes and BET surfaces, see WO 2009/148932. Silica is added in an amount of from 10 to 100 parts by weight, in some embodiments from 30 to 100 parts by weight, and in some embodiments from 30 to 95 parts by weight for 100 parts by weight of the total elastomeric polymer. Silica fillers can be used in combinations with other fillers including but not limited to carbon black, carbon-silica dual-phase-filler, clay, calcium carbonate, carbon nano tubes, magnesium carbonate and combinations thereof.

Carbon black and silica may be added together, in which case the total amount of carbon black and silica added is from 30 to 100 parts by weight and, in some embodiments, from 30 to 95 parts by weight per 100 parts by weight of the total elastomeric polymer. As long as such fillers are homogeneously dispersed in the elastomeric composition, increasing quantities (within the above ranges) result in compositions having excellent rolling and extruding processability and vulcanized products exhibiting favorable hysteresis loss properties, rolling resistance, improved wet skid resistance, abrasion resistance and tensile strength.

Carbon-silica dual-phase-filler may be used either independently or in combination with carbon black and/or silica in accordance with the present teachings. Carbon-silica dual-phase-filler can exhibit the same effects as those obtained by the combined use of carbon black and silica, even in the case where it is added alone. Carbon-silica dual-phase-filler is so called silica-coated-carbon black made by coating silica over the surface of carbon black, and is commercially available under the trademark CRX2000, CRX2002 or CRX2006 (products of Cabot Co.). Carbon-silica dual-phase-filler is added in the same amounts as described above with respect to silica. Carbon-silica dual-phase-filler can be used in combinations with other fillers including but not limited to carbon black, silica, clay, calcium carbonate, carbon nanotubes, magnesium carbonate and combinations thereof. In some embodiments, carbon black and silica, either individually or in combination, are used.

Silica, carbon black or carbon black-silica dual-phase-fillers or combinations thereof can be used in combination with natural fillers including but not limited to starch or lignin.

Polymer Composition

The second polymer composition comprising filler in accordance with the present invention can be prepared by kneading the above-described first polymer composition (containing at least one modified macromolecular compound according to the invention as defined above and including oil-containing first polymer composition varieties), and unmodified polymers (including oil extended varieties), fillers (carbon black, silica, carbon-silica dual-phase filler, etc.), optionally processing aids, oils, silane coupling agents, and other additives, in a kneader at 140° C. to 180° C., to form a second polymer composition containing filler.

Alternatively, second polymer compositions in accordance with the present invention can be prepared by kneading a polymer composition already containing at least one of the fillers (for example, carbon black, silica, carbon-silica dual-phase filler, etc.), formed as result of the polymer manufacturing process, and optionally processing aids, oils, silane coupling agents, fillers (for example, carbon black, silica, carbon-silica dual-phase filler, etc.) and other additives in a kneader at 140° C. to 180° C. to form a "first stage" second polymer composition containing filler. The formation of the "first stage" second polymer composition may comprise one or more mixing steps, preferably 2 to 7 mixing steps.

After cooling, vulcanizing agents, such as sulfur, vulcanizing accelerators, optionally zinc oxide and the like are added to the aforementioned filler-containing "first stage" second polymer composition, and the resulting mixture, also referred to as "second stage" second polymer composition, is blended using a Brabender mixer, Banbury mixer or open roll mill to form the desired shape, and the mixture is vulcanized at 140° C. to 180° C., to obtain a "vulcanized polymer composition" or "vulcanized elastomeric polymer composition" in the form of a vulcanized article.

Alternatively, vulcanizing agents, such as sulfur, vulcanizing accelerators, optionally zinc oxide and the like also can be added to the aforementioned first polymer composition, and the resulting mixture is blended using a Brabender mixer, Banbury mixer or open roll mill to form the desired shape, and the mixture is vulcanized at 140° C. to 180° C., to obtain a "vulcanized polymer composition" or "vulcanized elastomeric polymer composition" in the form of a vulcanized article.

The vulcanized polymer compositions of the present invention exhibit low rolling resistance, low dynamic heat build up and superior wet skid performance. As a result, the polymer compositions of the present invention are well suited for use in preparing tires, tire treads, side walls, and tire carcasses as well as other industrial products such as belts, hoses, vibration dampers and footwear components.

Polymer Chain P and Further Polymers

When the modified macromolecular compound of the present invention is prepared by a polymerization reaction of monomer mediated by a polymerization initiator according to Formula 4 or Formula 5, the polymer chain P is produced. In a further optional modification step involving a compound of Formula 6, the polymer chain P can be further modified. If the polymerization reaction is conducted by using a combination of the polymerization initiator according to Formula 4 or Formula 5 and a further initiator such as alkyllithium, e.g., butyllithium, the resulting polymer composition comprises both the modified macromolecular compound(s) of the invention and further non-modified polymers.

Examples of the polymer chain P and of the further polymers include homopolymers of conjugated dienes, especially butadiene or isoprene, and random or block co- and terpolymers of at least one conjugated diene, especially butadiene or isoprene, with at least one conjugated diene or with at least one aromatic α-olefin, and especially styrene and 4-methylstyrene, aromatic diolefin, especially divinylbenzene. Especially preferred is the random copolymerization, optionally terpolymerization, of at least one conjugated diene with at least one aromatic α-olefin, and optionally at least one aromatic diolefin or aliphatic α-olefin, and especially butadiene or isoprene with styrene, 4-methylstyrene and/or divinylbenzene. Additionally, especially preferred is the random copolymerization of butadiene with isoprene.

Examples of suitable polymer chains P and further polymers include the following: BR—polybutadiene; butadiene/C1-C4-alkyl acrylate copolymers; IR—polyisoprene; SBR—styrene/butadiene copolymers with styrene contents of 1 to 60, preferably 10 to 50 weight percent, including SSBR wherein the polymer is prepared in solution; SIR—styrene/isoprene copolymers with styrene contents of 1 to 60, preferably 10 to 50 weight percent including SSIR wherein the polymer is prepared in solution; BRIR—butadiene/isoprene copolymers with isoprene contents of 1 to 60, preferably 10 to 50 weight percent including BRIR wherein the polymer is prepared in solution; IIR—isobutylene/isoprene copolymers; IBR—isoprene/butadiene copolymers; NBR—butadiene/acrylonitrile copolymers; HNBR—partially hydrogenated or fully hydrogenated NBR rubber; and mixtures of theses rubbers; EPDM. The acronym "EPDM" represents an ethylene/propylene/diene copolymer.

In one embodiment, the polymer chain P or further polymer is a polybutadiene.

In another embodiment, the polymer chain P or further polymer is a butadiene/C1-C4-alkyl acrylate copolymer.

In another embodiment, the polymer chain P or further polymer is a butadiene/styrene copolymer.

In another embodiment, the polymer chain P or further polymer is a butadiene/styrene copolymer (SSBR) prepared in solution.

In another embodiment, the polymer chain P or further polymer is a isoprene/styrene copolymer (SSIR) prepared in solution.

In another embodiment, the polymer chain P or further polymer is a butadiene/isoprene copolymer (BRIR) prepared in solution.

In another embodiment, the polymer chain P or further polymer is a polychloroprene.

In another embodiment, the polymer chain P or further polymer is a polyisoprene, including synthetic polyisoprene and natural rubber.

In another embodiment, the polymer chain P or further polymer is a polystyrene.

In another embodiment, the polymer chain P or further polymer is a styrene/butadiene copolymer with a styrene unit content from 1 to 60 weight percent, preferably from 10 to 50 weight percent, based on the total weight of the copolymer.

In another embodiment, the polymer chain P or further polymer is a styrene/butadiene copolymer with a 1,2-polybutadiene unit content from 5 to 70 weight percent, preferably from 50 to 70, or 5 to 25 weight percent, based on the total weight of polybutadiene unit fraction of the copolymer.

In another embodiment, the polymer chain P or further polymer is a styrene/isoprene copolymer with a styrene unit content from 1 to 60 weight percent, preferably from 10 to 50 weight percent, based on the total weight of the copolymer.

In another embodiment, the polymer chain P or further polymer is a styrene/isoprene copolymer with a 1,2-polyisoprene unit content from 5 to 70 weight percent, preferably from 50 to 70, or 5 to 25 weight percent, based on the total weight of polybutadiene unit fraction of the copolymer.

In another embodiment, the polymer chain P or further polymer is a butadiene/isoprene copolymer with an isoprene unit content from 0.1 to 70 weight percent, preferably from 5 to 50 weight percent, based on the total weight of the copolymer.

In another embodiment, the polymer chain P or further polymer is a isobutylene/isoprene copolymer. In another embodiment, the polymer chain P or further polymer is a partially hydrogenated butadiene.

In another embodiment, the polymer chain P or further polymer is a partially hydrogenated styrene-butadiene copolymer.

INDUSTRIAL APPLICATIONS

The cross-linked (vulcanized) polymer compositions of the present invention exhibit reduced heat build up, reduced tan δ values at 60° C., higher tan δ at 0° C. or higher tan δ at −10° C., and a good balance of physical properties, including one or more of the following: abrasion resistance, tensile strength, modulus and tear, while compounds comprising the uncrosslinked elastomeric polymers (compounds prior to vulcanization) maintain good processing characteristics. They uncrosslinked compositions are useful in preparing tire treads having lower rolling resistance, higher wet grip, higher ice grip and lower heat built-up, while maintaining good wear properties.

The present invention also provides an article comprising at least one component formed from a composition in accordance with the present invention. In some embodiments, the article is a tire. In some embodiments, the article is a tire tread. In some embodiments, the article is a tire sidewall. In some embodiments, the article is an automotive part. In some embodiments, the article is a footwear component. In some embodiments, the inventive article is a belt, a gasket, a seal or a hose.

For producing vehicle tires, the following polymers are of particular interest for use in the polymer composition: natural rubber; emulsion SBR and solution SBR rubbers with a glass transition temperature above −50° C.; polybutadiene rubber with a high cis-1,4-unit content (>90%), such as obtained by using catalysts based on nickel, cobalt, titanium, vanadium, gadolinium or neodymium; and polybutadiene rubber with a vinyl content of 0 to 75%; and combinations thereof.

Furthermore, for producing vehicle tires, the following polymers are of particular interest for use in the polymer composition: polybutadiene rubber with a high trans-1,4-unit content (>75%), or SBR containing, for example, between 5 and 45 wt % styrene and a high trans-1,4-polybutadiene content (>75%) of the polybutadiene fraction of the copolymer (each type of polymer, SBR or BR, may be obtained with one or more initiator compounds comprising earth alkaline metal compounds, such as described in U.S. Pat. Nos. 6,693,160; 6,627,715; 6,489,415; 6,103,842; 5,753,579; 5,086,136; and 3,629,213, each of which is hereby incorporated herein by reference in its entirety; or by using catalysts based on cobalt, such as described in U.S. Pat. Nos. 6,310,152; 5,834,573; 5,753,761; 5,448,002 and 5,089,574, and U.S. Patent Application Publication No. 20030065114, each of which is hereby incorporated herein by reference in its entirety; or by using catalysts based on vanadium, such as described in European Patent Application No. 1367069; Japanese Patent Application No. 11301794 and U.S. Pat. No. 3,951,936, each of which is hereby incorporated herein by reference in its entirety; or by using catalysts based on neodymium, such as described in European Patent Application Nos. EP0964008 and EP0924214 and in U.S. Pat. Nos. 6,184,168; 6,018,007; 4,931,376; 5,134,199 and 4,689,368, each of which is hereby incorporated herein by reference in its entirety).

The compositions of the present invention may also be used to form high impact polystyrene (HIPS) and butadiene modified acrylonitrile-styrene copolymer (ABS). For example, see WO 2009/148932, incorporated herein by reference.

Definitions

Throughout this specification, atoms in chemical formulae are abbreviated with their usual elemental symbol, e.g. C=carbon, N=nitrogen, O=oxygen, Si=silicon, S=sulfur, H=hydrogen. As an exception, the letter P stands for an elastomeric diene polymer chain as defined herein.

The term "linear modified macromolecular compound" (or alpha-modified/omega-modified macromolecular compound) refers to a compound that is formed when one alpha-modified living polymer molecule reacts (terminates) with one equivalent of chain end-modifying agent. The linear modified macromolecular compound comprises defined polar groups or moieties at the alpha end (silanol group derived from an amine-protected amino silane polymerization initiator compound) and at the omega end (group derived from a sulfanylsilane chain end-modifying agent) of the polymer molecule. The term "alpha-modified" refers to modification of the polymer at the alpha end with an amino silane polymerization initiator compound as described herein.

The term "branched modified macromolecular compound" (or alpha-modified/branched modified macromolecular compound) refers to a compound that is formed when at least two living polymer molecules (at least one of the two polymer molecules being alpha-modified) react (terminate) with one equivalent of chain end-modifying agent. A "branched modified macromolecular compound" comprises at least two polymer chains linked to the coupling point at their omega chain end positions, while at least one of the linked chains comprises at least one silanol group (group derived from an amino silane polymerization initiator compound) at the alpha position. This coupling point is also referred to as a "central capped position". In a branched modified macromolecular compound, a polar group derived from an amino silane polymerization initiator compound is located at the "free" end of at least one polymer chain (or at least one polymer arm) end, thus not at the polymer chain (or polymer arm) end attached to the central capped position. Polar groups (derived from an initiator compound according to the invention) may, or may not, be present at each free end.

The amino silane polymerization initiator of Formula 4 or 5 reacts with monomers to form an "amino-silane alpha-modified" living polymer. The reaction of at least two living polymer molecules (at least one of them comprising an amino silane group of the alpha end of the macromolecular compound) with one equivalent of chain end-modifying agent results in a branched modified macromolecular compound. Here, the "alpha-modified" macromolecular compound (a reacted living alpha-modified macromolecular compound) is linked to a silicon atom derived from the chain end-modifying compound. The reaction of one "alpha-modified living polymer molecule" with one chain end-modifying compound of Formula 6 results in a linear modified macromolecular compound. Here, the "alpha-modified" macromolecular compound (a reacted living alpha-modified macromolecular compound) is linked via one valence on a silicon atom, each derived from the chain end-modifying compound.

As discussed above, the term "linear modified macromolecular compound" is also referred to as an "alpha-modified/omega-modified macromolecular compound" in order to indicate that the macromolecule is modified at its alpha (first) end with a moiety derived from an amino silane polymerization initiator compound, and also at its omega (last) end with a moiety derived from the chain end-modifying compound. The term "branched modified macromolecular compound" is also referred to as an "alpha-modified/branched modified macromolecular compound" in order to indicate that the macromolecule is modified at its alpha (first) end with a moiety derived from an amino silane initiator compound, and also within its chain by a moiety derived from the chain end-modifying compound, to form a point of branching. In this case, the chain end-modifying agent comprises more than one reactive group capable of reacting with living "alpha-modified" polymer chains. "Linear modified macromolecular compounds" and "alpha-modified/branched modified macromolecular compounds" are contacted with a protonating agent for terminating the polymerization reaction. The use of the protonating agent provides the structure of the polar groups derived from the amino silane polymerization initiator and from the chain end-modifying compound. For example, the amine present in the alpha amino silane group of the modified macromolecular compound is removed, leading to the formation of an alpha silanol-modified macromolecular compound. As discussed above, a position within the polymer resulting from the reaction of a chain end-modifying agent with at least two anionic living polymer chains (or alpha-modified living macromolecular compounds) is referred to as a "central cap" or "central capped position" and is located within the alpha-modified branched macromolecular compound.

It is noted that macromolecular compounds used for the preparation of branched modified macromolecular compounds or linear modified macromolecular compounds may already contain polymer chain branches. Such polymer chain branches may be formed prior to the coupling reaction and prior to the chain end modification reaction. For example, such polymer branches may be formed in the course of the monomer polymerization process, or may be formed after contacting the living polymer with Lewis bases, such as used as a randomizer agent or as an accelerator of the polymerization rate. Such polymer branches can also be formed in the course of chain transfer reactions, initiated through the presence of an amino silane polymerization initiator, precursor molecules of the amino silane polymerization initiator. It is furthermore noted that branching points in macromolecular compounds not containing "central caps" can also be formed when a radical is formed at one position of a macromolecular compound, as result of exposure to UV radiation or exposure to elevated temperature. A macromolecule containing a free radical can react with another polymer chain leading to interchain carbon-carbon bond formation. The terms "linear modified macromolecular compounds" and "branched modified macromolecular compounds" do not exclude the presence of branches formed by these occasional side reactions discussed and the presence of branches formed through use of coupling agents as described herein. For example, branches can be formed when silicon or tin tetrahalides, tetraalkoxy silane, divinylaromatic or divinylaliphatic compounds are added to the polymerization mixture.

A sufficient amount of linear modified macromolecular compounds and branched modified macromolecular compounds is produced by using at least one amino silane polymerization initiator compound and at least one chain end-modifying compound to provide a first (uncrosslinked) polymer composition having an increased content of functionalized macromolecular compounds. The use of the first polymer composition in a second polymer composition, further comprising filler particles, will increase the interaction of the modified polymers with the filler particles as well as increase the interaction of the modified polymers with unsaturations in polymer backbones. These interactions are particularly desirable when the polymer composition is vulcanized to produce a vulcanized or crosslinked elastomeric polymer composition. Polymers having an unsaturated polymer backbone include the modified polymers of the invention, or other polymers containing unsaturated carbon-carbon bonds, which are added to the first polymer composition or to a second "filler-containing" composition. The distribution of filler particles in the second polymer composition will be improved, and the hysteresis loss in the corresponding vulcanizate will be decreased.

As used herein, the term "alkyl" refers to at least one aliphatic group and may also refer to two or more aliphatic groups. The alkyl group may be linear, branched, cyclic or a combination thereof, and may be saturated or unsaturated. In some embodiments, the alkyl group is linear, branched, cyclic or a combination thereof, and saturated. In some embodiments, the alkyl group is linear and saturated or branched and saturated. The term "alkyl" is understood to include both straight chain aliphatic hydrocarbon groups (for example, methyl (Me), ethyl (Et), n-propyl (Pr), n-butyl (Bu), n-pentyl, n-hexyl, etc.), branched aliphatic hydrocarbon groups (for example, isopropyl, tert-butyl, etc.) and carbon-based non-aromatic aliphatic hydrocarbon groups. In some embodiments, "alkyl" refers to saturated linear, branched or cyclic (or combinations thereof) aliphatic hydrocarbon groups, and unsaturated, linear, branched or cyclic (or combinations thereof) aliphatic hydrocarbon groups.

The term "aryl" as used herein refers to at least one aromatic ring, and may also refer to two or more aromatic rings. The term "aryl" is understood to include phenyls, biphenyls and other benzenoid compounds, each optionally substituted with alkyl, alkoxy or other heteroatoms, such as oxygen-, nitrogen-, sulfur- and/or phosphorus-containing moieties The term "alkoxy" is understood to include methoxy (MeO), ethoxy (EtO), propoxy (PrO), butoxy (BuO), isopropoxy (iPrO), isobutoxy (iBuO), pentoxy, and the like.

As used herein, the term "aralkyl" refers to a group containing at least one aromatic ring and at least one alkyl group. The term "aralkyl" is understood to mean an aryl group bonded to an alkyl.

The designation of $(C_a-C_b)$, for example $(C_1-C_{12})$, as used herein, is intended to mean a range of the number of carbon atoms of from a to b and includes all individual values and subranges from a to b.

The term "hydrocarbon groups" is understood to include any group, including saturated, unsaturated, linear, branched, cyclic and aromatic groups, which only consists of the elements hydrogen and carbon.

EXAMPLES

The following Examples are provided in order to further illustrate the invention, and are not to be construed as limiting. The Examples include the preparation of the aminosilane polymerization initiator compounds; the preparation of sulfanylsilane chain end modifiers; the preparation and testing of modified elastomeric polymers (i.e. polymer compositions comprising the modified macromolecular compound of the present invention); and the preparation and testing of uncrosslinked polymer compositions, including the first polymer composition and second polymer composition, as well as of cross-linked or cured polymer compositions, also referred to as vulcanized polymer composition. Unless stated otherwise, all parts and percentages are expressed on a weight basis. The term "overnight" refers to a time of approximately 16-18 hours, and "room temperature" refers to a temperature of about 20-25° C.

The polymerizations were performed under exclusion of moisture and oxygen, in a nitrogen atmosphere. Various methods were used to test and measure the examples. A description of each technique is provided below.

The vinyl content in the conjugated diolefin part was additionally determined by IR absorption spectrum (Morello method, IFS 66 FT-IR spectrometer of Bruker Analytic GmbH). The IR samples were prepared using $CS_2$ as swelling agent.

Bonded styrene content: A calibration curve was prepared by IR absorption spectrum (IR (IFS 66 FT-IR spectrometer of Bruker Analytik GmbH). The IR samples were prepared using $CS_2$ as swelling agent.). For the IR determination of the bound styrene in styrene-butadiene copolymers, four bands are assessed: a) band for trans-1,4-polybutadiene units at 966 $cm^{-1}$, b) band for cis-1,4-polybutadiene units at 730 $cm^{-1}$, c) band for 1,2-polybutadiene units at 910 $cm^{-1}$ and band for bound styrene (styrene aromatic bond) at 700 $cm^{-1}$. The band heights are normalized according to the appropriate extinction coefficients and summarized to a total of 100%. The normalization is done via $^1$H- and $^{13}$C-NMR. The styrene content was alternatively determined by NMR (NMR (Avance 400 device ($^1$H=400 MHz; $^{13}$C=100 MHz) of Bruker Analytik GmbH)).

The 1D NMR spectra were collected on a BRUKER Avance 200 NMR spectrometer (BRUKER BioSpin GmbH), using a "5 mm Dual detection probe." The field homogeneity was optimized by maximizing the deuterium lock signal. The samples were shimmed by optimizing the deuterium lock signal. The samples were run at room temperature (298 K). The following deuterated solvents were used: $C_6D_6$(7.16 ppm for $^1$H; 128.06 ppm for $^{13}$C-NMR), $CDCl_3$ (7.24 ppm for $^1$H; 77.03 ppm for $^{13}$C-NMR), $d^8$-THF (1.73, 3.58 ppm for $^1$H; 25.35 ppm for $^{13}$C), the signals of the remaining protons of deuterated solvents were each used as an internal reference.

For spectral processing, the BRUKER 1D WINNMR software (version 6.0) was used. Phasing, base line correction and spectral integration of the resulting spectra was done in the manual mode. For acquisition parameters see Table 1.

TABLE 1

| 1D-NMR acquisition parameters using BRUKER standard pulse sequences | | | |
|---|---|---|---|
| | 1H-NMR | 13C-NMR | 29Si-NMR |
| Observe frequency | 400.130 MHz | 100.613 MHz | 79.495 |
| Spectral width | 8278.146 Hz | 23980.814 Hz | 31847.133 Hz |
| BRUKER Pulse program | Zg30 | Zgpg30 | Zgig |
| Pulse angle | 30° | 30° | 30° |
| Relaxation delay | 1.0 s | 2.0 s | 60 s |
| Number of Data points for FT | 32K | 32K | 32K |
| Line broadening | 0.3 Hz | 1 Hz | 1 Hz |

TABLE 1-continued

| 1D-NMR acquisition parameters using BRUKER standard pulse sequences | | | |
|---|---|---|---|
| | 1H-NMR | 13C-NMR | 29Si-NMR |
| Number of accumulated scans | 64 | >1000 | >1000 |

GPC-Method: SEC calibrated with narrow distributed polystyrene standard.

Sample Preparation:
a1) Oil Free Polymer Samples:
About "9-11 mg" dried polymer sample (moisture content<0.6%) was dissolved in 10 mL tetrahydrofuran, using a brown vial of 10 mL size. The polymer was dissolved by shaking the vial for 20 min at 200 u/min.
a2) Oil Containing Polymer Samples:
About "12-14 mg" dried polymer sample (moisture content<0.6%) was dissolved in 10 mL tetrahydrofuran, using a brown vial of 10 mL size. The polymer was dissolved by shaking the vial for 20 min at 200 u/min.
b) Polymer solution was transferred into a 2 ml vial using a 0.45 μm disposable filter.
c) The 2 ml vial was placed on a sampler for GPC-analysis.
Elution rate: 1.00 mL/min
Injection volume: 100.00 μm (GPC-method B 50.00 μm)
The measurement was performed in THF at 40° C. Instrument: Agilent Serie 1100/1200;
Module setup: Iso pump, autosampler, thermostat, VW—Detector, RI—Detector, Degasser;
Columns PL Mixed B/HP Mixed B.

In each GPC-device 3 columns were used in an connected mode. The length of each of the columns: 300 mm; Column Type: 79911 GP-MXB, Plgel 10 μm MIXED-B GPC/SEC Columns, Fa. Agilent Technologies (eigentlicher Hersteller ist auch Polymer Laboratories) GPC Standards: EasiCal PS-1 Polystyrene Standards, Spatula A+B
Styrene Standard Manufacturer:

| | |
|---|---|
| Polymer Laboratories Now entity of Varian, Inc. Website: http://www.polymerlabs.com | Polymer Laboratories Varian Deutschland GmbH |

Polydispersity (Mw/Mn) was used as a measure for the width of molecular weight distribution. The calculation of Mw and Mn (weight average molecular weight (Mw) and number average molecular weight (Mn)) was based on one of two procedures.

The Mp1, Mp2, Mp3 correspond to the (maximum peak) molecular weight measured at the first, second or third peaks of the GPC curve [the first peak Mp1 (lowest molecular weight) is located on the right side of the curve, and the last peak (highest molecular weight) is located on the left side of the curve], respectively. Maximum peak molecular weight means the molecular weight of the peak at the position of maximum peak intensity. The Mp2 and Mp3 are two or three polymer chains coupled to one macromolecule. Mp1 is one polymer chain (base molecular weight—no coupling of two or more polymer chains to one macromolecule).

The total coupling rate represents the sum of the weight fractions of coupled polymers relative to the total polymer weight, including the sum of the weight fractions of all coupled polymers and the uncoupled polymer. The total coupling rate is calculated as shown below. CR(total)= (ΣArea fraction of all coupled peaks [Peak with maximum Mp2 to peak with highest indexed peak maximum])/(ΣArea fraction of all peaks [Peak with peak maximum Mp1 to peak with highest indexed peak maximum]).

The individual coupling rate (e.g. two polymer arms coupled corresponding to the peak with peak maximum Mp2) is calculated as depicted below:

CR(2arms)=(Area fraction of peak with peak maximum Mp2)/(ΣArea fraction of all peaks [Peak with peak maximum Mp1 to peak with highest indexed peak maximum]).

Rubber compounds were prepared by combining the components listed below in Tables 6 and 7 in a "380 cc Banbury mixer (Labstation 350S from Brabender GmbH&Co KG)," following a two-stage mixing process. Stage 1—mixed all components together, except the components of the vulcanization package, to form a stage 1 formulation. Stage 2—components of vulcanization package were mixed into stage 1 formulation to form a stage 2 formulation.

Mooney viscosity was measured according to ASTM D 1646 (2004), with a preheating time of one minute and a rotor operation time of 4 minutes, at a temperature of 100° C. [ML1+4(100° C.)], on a MV 2000E from Alpha Technologies UK. The rubber Mooney viscosity measurement is performed on dry (solvent free) raw polymer (unvulcanized rubber). The Mooney values of the raw polymers are listed in Table 5.

Measurement of unvulcanized rheological properties was performed according to ASTM D 5289-95 (reapproved 2001), using a rotor-less shear rheometer (MDR 2000 E from Alpha Technologies UK) to measure Time to Cure (TC). The rheometer measurement was performed at a constant temperature of 160° C. on an non-vulcanized second stage polymer formulation, according to Tables 8 and 10. The amount of polymer sample is about 4.5 g. Sample shape and shape preparation are standardized and defined by the measurement device (MDR 2000 E from Alpha Technologies UK).

The "TC 50" and "TC 90" values are the respective times required to achieve 50% and 90% conversion of the vulcanization reaction. The torque is measured as a function of time of reaction. The vulcanization conversion is automatically calculated from the generated torque versus time curve.

Tensile Strength, Elongation at Break and Modulus at 300% Elongation (Modulus 300) were measured according to ASTM D 412-98A (reapproved 2002), using a dumbbell die C test piece on a Zwick Z010. Of the standardized dumbbell die C test pieces, those of "2 mm thickness" were used. The tensile strength measurement was performed at room temperature, on a cured (vulcanized) second stage polymer sample, prepared according to Tables 9, and 11. Stage 2 formulations were vulcanized within 16-25 minutes at 160° C. to TC 95 (95% vulcanization conversion) (see cure data in Tables 8 and 10).

Heat build up was measured according to ASTM D 623, method A, on a Doli 'Goodrich'-Flexometer. The heat built up measurement was performed on a vulcanized second stage polymer samples according to Tables 8 and 10. Stage 2 formulations were vulcanized at 160° C. to TC 95 (95% vulcanization conversion) (see cure data in Tables 8 and 10).

Tan δ at 60° C. and tan δ at 0° C. as well as tan δ at −10° C. measurements were performed on cylindrical specimen, using a dynamic mechanical thermal spectrometer "Eplexor 150N," manufactured by Gabo Qualimeter Testanlagen GmbH (Germany), by applying a compression dynamic strain of 0.2%, at a frequency of 2 Hz, at the respective temperatures. The smaller the index at a temperature of 60° C., the lower the rolling resistance (lower=better). Tan δ (0° C.) was measured using the same equipment and load conditions at 0° C. The larger the index at this temperature, the better the wet skid resistance (higher=better). Tan δ at 60° C. and tan δ at 0° C. as well as tan δ at −10° C. were determined (see Tables 9 and 11). Stage 2 formulations were vulcanized at 160° C. to TC 95 (95% vulcanization conversion) (see cure data in Tables 8 and 10). The process leads to the formation of visually "bubble free," homogeneous cured rubber disc of "60 mm diameter" and "10 mm height." A specimen was drilled out of the aforementioned dish and has a size of "10 mm diameter" and "10 mm height."

DIN abrasion was measured according to DIN 53516 (1987-06-01). The larger the index, the lower the wear resistance (lower=better). The abrasion measurement was performed on a vulcanized, second stage polymer formulation according to Tables 8 and 10. In general, the higher the values for Elongation at Break, Tensile Strength, Modulus 300, and tan δ at 0° C., the better the sample performance; whereas the lower the Tan δ at 60° C., Heat Build Up and Abrasion, the better the sample performance.

Modifier Preparation: Six Amino Silane Polymerization Initiator Precursor compounds (Pr1 to Pr6), nine Amino Silane Polymerization Initiator Compounds (I2a, I2b, 13 to 19), one Coupling Modifier Agent and three Chain End modifier agents were each prepared as an example. The two Amino Silane Polymerization Initiator Precursor compounds Pr5 and Pr6 and four Amino Silane Polymerization Initiators 16, 17, 18 and 19 are made to provide comparative polymer examples, while Amino Silane Polymerization Initiator Precursor compounds Pr1 to Pr4 and Amino Silane Polymerization Initiators I2a, I2b, I3, I4 and I5 are made to provide examples for the subject invention. The structural formula and method of preparation (or source for obtaining) are provided below. The combined use of the subject amino silane polymerization initiator compounds selected from I2 (including I2a and I2b) to I6, optional coupling agents C1 and C2 and chain end modifier agents E1 to E4, particularly new chain end modifier agents E3 and E4, are representative for the present invention, whereas (i) the combined use of initiator compounds lacking polar heteroatoms in the anionic moiety of the initiator compound (such as alkyl lithium initiator compounds, e.g. n-butyl lithium), coupling agents and chain end modifier agents and the combined use of amino silane initiator compounds and coupling agents, while not including a coupling modifier agent or chain end modifier agents, is for comparative purposes.

Comparative examples I8 and I9 and polymers derived therefrom are made to demonstrate that (a) no modified lithium compound is formed according to examples 19A and 21 in WO 2011/082277, and that (b) the properties of example 28 in Table 6 of WO 2011/082277 could not be reproduced.

Preparation of Amino Silane Polymerization Initiator Precursor Compounds

Amino silane polymerization initiator precursor compound Pr1 was prepared as follows:

(Formula Pr1)

A 500 mL round bottom flask was charged with 250 mL cyclohexane and with 0.23 mol diethylamine. (Chloromethyl)dimethylchlorosilane (0.10 mol) was added drop wise under vigorous stirring at room temperature. The reaction mixture was stirred overnight at room temperature. The mixture was filtered to remove the precipitated ammonium salt and washed twice with cyclohexane (20 mL). All volatiles were removed under reduced pressure (10 mbar), and the crude product was distilled under vacuum to yield 13.7 g of a colorless oil. Boiling point of Pr1: 43° C. at 15 Torr; isolated yield: 76%; Purity>95% (NMR).

$^1$H-NMR (400 MHz, 23° C., $C_6D_6$): δ=2.64 (q, 4H, $NCH_2$), 2.52 (s, 2H, $ClCH_2$), 0.86 (t, 6H, $NCH_2CH_3$), 0.10 (s, 6H, $SiMe_2$) ppm; $^{13}$C-NMR (101 MHz, 23° C., $C_6D_6$) δ=40.30 ($NCH_2$), 30.98 ($ClCH_2$), 16.15 ($NCH_2CH_3$), −3.55 ($SiMe_2$) ppm.

Amino silane polymerization initiator precursor compound Pr2 was prepared as follows:

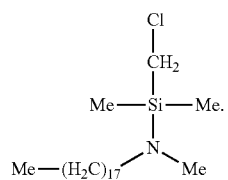

(Formula Pr2)

N-Methyloctadecylamine (0.018 mol) and 0.025 mol of triethylamine were dissolved in 100 mL cyclohexane. To this solution (chloromethyl)dimethylchlorosilane (0.018 mol) was added drop wise under vigorous stirring. The mixture was stirred overnight, filtered to remove the precipitated ammonium salt and washed twice with cyclohexane (10 mL). All volatiles were removed under reduced pressure (10 mbar) to yield 5.85 g of a colorless oil. Yield: 85%; Purity: ~90% (NMR).

$^1$H-NMR (400 MHz, 23° C., $C_6D_6$): δ=2.65 (t, 2H, $NCH_2$), 2.57 (s, 2H, $ClCH_2$), 2.35 (s, 3H, $NCH_3$), 1.42-1.18 (m, 32H, $NCH_2(CH_2)_{16}CH_3$), 0.92 (s, 3H, $NCH_2(CH_2)_{16}CH_3$) 0.13 (s, 6H, $SiMe_2$) ppm; $^{13}$C-NMR (101 MHz, 23° C., $C_6D_6$) δ=50.69 ($NCH_2$), 34.53 ($NCH_3$), 32.40 ($ClCH_2$), 30.63, 30.36-30.17, 29.90, 29.52, 27.39 (16 signals for $CH_2$ groups), 14.43 ($CH_2CH_3$), −3.78 ($SiMe_2$) ppm.

Amino silane polymerization initiator precursor compound Pr3 was prepared as follows:

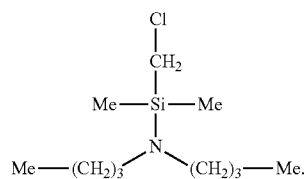

(Formula Pr3)

Dibutylamine (0.025 mol) and 0.035 mol of triethylamine were dissolved in 100 mL cyclohexane. To this solution (chloromethyl)dimethylchlorosilane (0.025 mol) was added drop wise under vigorous stirring. The mixture was stirred overnight, filtered to remove the precipitated ammonium salt and washed twice with cyclohexane (10 mL). All volatiles were removed under reduced pressure (10 mbar) to yield 3.40 g of a colorless oil. Yield: 85%; Purity: >90% (NMR).

$^1$H-NMR (400 MHz, 23° C., $C_6D_6$): δ=2.63 (t, 4H, $NCH_2$), 2.58 (s, 2H, $ClCH_2$), 1.34-1.27 (m, 4H, $NCH_2CH_2$), 1.15 (sext., 4H, $N(CH_2)_2CH_2$), 0.87 (t, 6H, $N(CH_2)_3CH_3$), 0.15 (s, 6H, $SiMe_2$) ppm; $^{13}$C-NMR (101 MHz, 23° C., $C_6D_6$) δ=46.51 (butyl-C), 32.79 (butyl-C), 31.04 ($ClCH_2$), 20.62 (butyl-C), 14.36 (butyl-C), −3.41 ($SiMe_2$) ppm.

Amino silane polymerization initiator precursor compound Pr4 was prepared as follows:

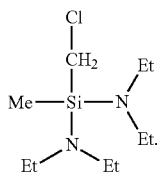

(Formula Pr4)

(Chloromethyl)methyldichlorosilane (0.025 mol) was dissolved in 60 mL diethylether and diethylamine (0.11 mol) was added drop wise under vigorous stirring at room temperature. The reaction mixture was stirred for two days at room temperature. The mixture was filtered to remove the precipitated ammonium salt and washed twice with diethylether (15 mL). All volatiles were removed under reduced pressure (10 mbar) to yield 5.05 g of a colorless oil which was used without further purification. Yield: 85%; Purity>90% (NMR).

$^1$H-NMR (400 MHz, 23° C., $C_6D_6$): δ=2.73 (dq, 8H, $NCH_2$), 2.67 (s, 2H, $ClCH_2$), 0.93 (t, 12H, $NCH_2CH$), 0.20 (s, 3H, $SiMe$) ppm; $^{13}$C-NMR (101 MHz, 23° C., $C_6D_6$) δ=39.43 ($NCH_2$), 29.71 ($ClCH_2$), 16.59 ($NCH_2CH_3$), −4.09 ($SiMe$) ppm.

Amino silane polymerization initiator precursor compound Pr5, described in WO 2011/031943, was prepared as follows:

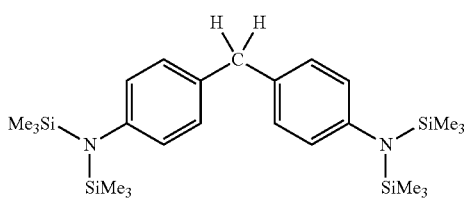

(Formula Pr5)

4,4'-Diaminodiphenylmethane (0.040 mol) and 0.10 mol triethylamine were dissolved in 100 mL dichloromethane and 0.10 mol chlorotrimethylsilane was added at 0° C. All volatiles were removed under vacuum. The residue was dissolved in about 80 mL cyclohexane and filtered to remove the ammonium salt. After removal of the solvent in vacuum a light-brown oil was obtained which was identified by NMR as N,N'-(bistrimethylsilyl)-4,4'-diaminodiphenylmethane. This oily intermediate was dissolved in 60 mL tetrahydrofuran and 0.088 mol of n-butyllithium was added drop wise at 0° C. After 1.5 h at 0° C. was added 0.092 mol chlorotrimethylsilane and the mixture was warmed to room temperature and stirred overnight. All volatiles were removed under vacuum and the residue was extracted with 60 mL cyclohexane. Removal of the solvent yields 19 g of a pale yellow crystalline solid. Yield: 98%; Purity>95% (NMR).

¹H-NMR (400 MHz, 23° C., C₆D₆): δ=6.97 (m, 4H, Aryl-H), 6.83 (m, 4H, Aryl-H), 3.79 (s, 2H, CH₂), 0.11 (s, 36H, SiMe₃) ppm; ¹³C-NMR (101 MHz, 23° C., C₆D₆) δ=145.94 (Aryl-C), 136.94 (Aryl-C), 130.42 (Aryl-C), 129.48 (Aryl-C), 40.94 (CH₂), 2.26 (SiMe₃) ppm.

Amino silane polymerization initiator precursor compound Pr6, described in WO 97/06192, was prepared as follows:

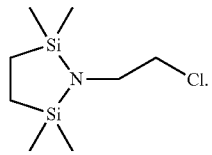

(Formula Pr6)

3-Chloropropylamine hydrochloride (0.020 mmol) was dissolved in 40 dichloromethane and 0.070 mol triethylamine was added. To this solution 0.020 mol of 1,2-bis(chlorodimethylsilyl)ethane dissolved in 10 mL dichloromethane was added under stirring. The mixture was stirred overnight at room temperature. All volatiles were removed in vacuum and the residue was extracted with 40 mL cyclohexane. After removal of the solvent, 3.60 g of a yellow oil was obtained. Yield: 74%; Purity: >95% (NMR).

¹H-NMR (400 MHz, 23° C., C₆D₆): δ=3.19 (t, 2H, NCH₂), 2.79 (t, 2H, ClCH₂), 1.62 (m, 2H, CH₂CH₂CH₂), 0.73 (s, 4H, Si(Cl₂)₂Si), 0.05 (s, 12H, SiMe₂) ppm; ¹³C-NMR (101 MHz, 23° C., C₆D₆) δ=42.60 (CH₂), 39.55 (CH₂), 37.04 (CH₂), 8.39 (Si(CH₂)₂Si), 0.02 (SiMe₂) ppm.

Amine silane polymerization initiator precursor compounds Pr7 and Pr8, described in WO 2011/082277, were purchased at ABCR:

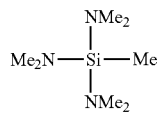

(Formula Pr7)

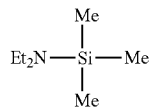

(Formula Pr8)

Amino Silane Polymerization Initiator Compounds
n-Butyllithium purchased from Aldrich as a 20 wt % solution in cyclohexane was denoted as "initiator I1."
Preparation of Amino Silane Polymerization Initiator Compounds
Preparation of Lithium Methyl Amino Silane*TMEDA compounds I2a and I2b
Preparation Step 1—Lithium Methyl Amino Silane Li1
Amine silane alkyl lithium Li1 was prepared as follows:

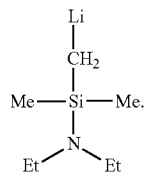

(Formula Li1)

Reaction of Amino Methyl Silane Pr1 with Lithium

The reaction was performed in an inert atmosphere. Lithium powder (4.00 mg, 0.60 mmol) and compound Pr1 (0.20 mmol, 36.0 mg) were stirred overnight in 2 mL cyclohexane. The mixture was filtered to remove lithium and formed lithium chloride and the solvent was removed to yield a white solid. The solid was dissolved in C₆D₆ and the NMR-analysis revealed the formation of the lithiated compound Li1, additionally no resonances for the starting material Pr1 could be detected.

¹H-NMR (400 MHz, 23° C., C₆D₆): δ=2.86 (q, 4H, NCH₂), 0.99 (t, 6H, NCH₂CH₃), 0.37 (s, 6H, SiMe₂), −1.71. (s, 2H, LiCH₂), ppm; ¹³C-NMR (101 MHz, 23° C., C₆D₆) δ=39.22 (NCH₂), 12.79 (NCH₂CH₃), 3.04 (br, LiCH₂), 0.23 (SiMe₂) ppm.

Preparation Step 2—Lithium Methyl Amino Silane*TMEDA I2a

Lithium Methyl Amino Silane*TMEDA I2a was prepared by reacting lithium methyl amino silane Li1 with TMEDA as follows:

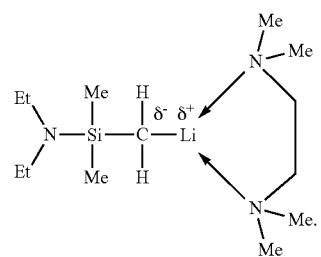

(Formula I2a)

The reaction was performed in an inert atmosphere. Lithium powder (4.00 mg, 0.60 mmol) and compound Pr1 (0.20 mmol, 36.0 mg) were stirred overnight in 2 mL cyclohexane. The mixture was filtered to remove lithium and formed lithium chloride and the solvent was removed to yield a white solid. The solid was dissolved in C₆D₆ and TMEDA (0.60 mmol, 70 mg) was added, the NMR-analysis indicates the formation of the compound I2a.

¹H-NMR (400 MHz, 23° C., C₆D₆): δ=2.97 (q, 4H, NCH₂), 1.12 (t, 6H, NCH₂CH₃), 0.35 (s, 6H, SiMe₂), −1.75. (s, 2H, LiCH₂) ppm, additionally signals for TMEDA at 2.25 (s) and 2.10 (s) ppm could be detected; ¹³C-NMR (101 MHz, 23° C., C₆D₆) δ=39.93 (NCH₂CH₃), 14.68 (NCH₂CH₃), 3.37 (SiMe₂), −7.20 (br, LiCH₂) ppm, additionally signals for TMEDA at 58.21 and 46.13 ppm could be detected Preparation Step 2—Lithium Methyl Amino Silane*DTHFP I2b Lithium Methyl Amino Silane*DTHFP I2b is was prepared by reacting lithium methyl amino silane Li1 with DTHFP as follows:

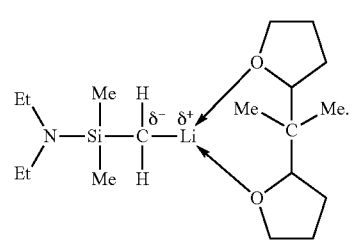

(Formula I2b)

The reaction was performed in an inert atmosphere. Lithium powder (4.00 mg, 0.60 mmol) and compound Pr1 (0.20 mmol, 36.0 mg) were stirred overnight in 2 mL cyclohexane. The mixture was filtered to remove lithium and formed lithium chloride and the solvent was removed to yield a white solid. The solid was dissolved in $C_6D_6$ and DTHFP (0.60 mmol, 111 mg) was added, the NMR-analysis indicates the formation of the compound I2b.

$^1$H-NMR (400 MHz, 23° C., $C_6D_6$): δ=3.20 (q, 4H, $NCH_2$), 1.21 (t, 6H, $NCH_2CH_3$), 0.32 (s, 6H, $SiMe_2$), −1.69. (s, 2H, $LiCH_2$), ppm, additionally signals for DTHFP at 3.54-3.86 (m), 1.57-1.42 (m), 1.02 (s), 0.88 (s) and 0.76 ppm could be detected; $^{13}$C-NMR (101 MHz, 23° C., $C_6D_6$) δ=40.78 ($NCH_2$), 16.46 ($NCH_2CH_3$), 3.84 ($SiMe_2$), −8.08 (br, $LiCH_2$) ppm, additionally signals for DTHFP at 85.15, 84.26, 68.28, 67.94, 40.42, 39.82, 26.79, 26.72, 26.36, 26.09, 19.91 and 18.21 ppm could be detected Preparation of Lithium Methyl Amino Silane I3

Preparation Step 1—Lithium Methyl Amino Silane Li2

Amine silane alkyl lithium Li2 was prepared as follows:

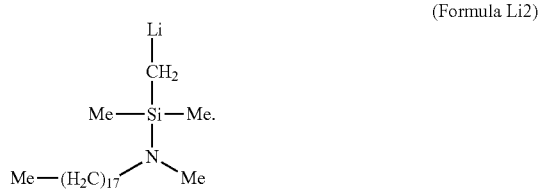

(Formula Li2)

Reaction of Amino Methyl Silane Pr2 with Lithium

The reaction was performed in an inert atmosphere. The reaction was performed in an inert atmosphere. Lithium powder (395 mg, 56.9 mmol) and compound Pr2 (5.59 g, 14.3 mmol) were dissolved in 80 mL cyclohexane and stirred overnight at 50° C. The mixture was filtered to remove lithium and formed lithium chloride and the solvent was removed to yield a light yellow oily solid. NMR-analysis of the residue revealed the formation of the lithiated compound Li2, additionally no resonances for the starting material Pr2 could be detected.

$^1$H-NMR (400 MHz, 23° C., $C_6D_6$): δ=2.71 (t, 2H, $NCH_2$), 2.42 (s, 3H, $NCH_3$), 1.40-1.32 (m, 32H, $NCH_2(CH_2)_{16}CH_3$), 0.92 (t, 3H, $NCH_2(CH_2)_{16}CH_3$) 0.32 (s, 6H, $SiMe_2$), −1.67 (s, 2H, $CH_2Li$) ppm; $^{13}$C-NMR (101 MHz, 23° C., $C_6D_6$) δ=50.76 ($NCH_2$), 35.97 ($NCH_3$), 32.47, 30.32-30.26, 29.96, 29.61, 28.27, 27.58, 23.23 (16 signals for $CH_2$ groups), 14.49 ($CH_2CH_3$), −0.35 ($SiMe_2$), −8.88 ($CH_2Li$) ppm.

Preparation Step 2—Lithium Methyl Amino Silane*TMEDA I3

The reaction of Lithium Methyl Amino Silane Li2 with TMEDA was performed in situ according to the general procedure for the copolymerization of styrene and butadiene (see below). Therefore Lithium Methyl Amino Silane*TMEDA I3 was formed upon addition of Lithium Methyl Amino Silane Li2 to the polymerization vessel already comprising tetramethylethylene diamine (TMEDA), cyclohexane solvent; butadiene monomer and styrene monomer. The amounts of Lithium Methyl Amino Silane Li2, of TMEDA and of the monomers are listed in Table 4.

Preparation of Lithium Methyl Amino Silane I4
Preparation Step 1—Lithium Methyl Amino Silane Li3
Lithium Methyl Amino Silane Li3 was prepared as follows:

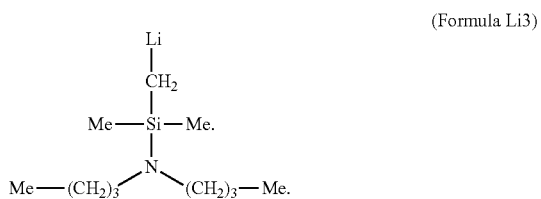

(Formula Li3)

Reaction of Amino Methyl Silane Pr3 with Lithium

The reaction was performed in an inert atmosphere. Lithium powder (12.0 mg, 1.60 mmol) and compound Pr3 (0.41 mmol, 96.0 mg) were stirred overnight in 4 mL cyclohexane. The mixture was filtered to remove lithium and formed lithium chloride and the solvent was removed to yield a light yellow oily solid. The residue was dissolved in $C_6D_6$ and the NMR-analysis revealed the formation of the lithiated compound Li3, additionally no resonances for the starting material Pr3 could be detected.

$^1$H-NMR (400 MHz, 23° C., $C_6D_6$): δ=2.93 (t, 4H, $NCH_2$), 1.61 (br, 4H, $NCH_2CH_2$), 1.29 (sext., 4H, $N(CH_2)_2CH_2$), 0.96 (t, 6H, $N(CH_2)_3CH_3$), 0.42 (s, 6H, $SiMe_2$), −1.59 (s, 2H, $CH_2Li$) ppm; $^{13}$C-NMR (101 MHz, 23° C., $C_6D_6$) δ=46.81 (butyl-C), 30.51 (butyl-C), 21.36 (butyl-C), 14.39 (butyl-C), 0.32 ($SiMe_2$), −8.75 (br, $CH_2Li$) ppm.

Preparation Step 2—Lithium Methyl Amino Silane*TMEDA I4

The reaction of Lithium Methyl Amino Silane Li3 with TMEDA was performed in situ according to the general procedure for the copolymerization of styrene and butadiene (see below). Therefore Lithium Methyl Amino Silane*TMEDA I4 was formed upon addition of Lithium Methyl Amino Silane Li3 to the polymerization vessel already comprising tetramethylethylene diamine (TMEDA), cyclohexane solvent; butadiene monomer and styrene monomer. The amounts of Lithium Methyl Amino Silane Li3, of TMEDA and of the monomers are listed in Table 4.

Preparation of Lithium Methyl Amino Silane I5
Preparation Step 1—Lithium Methyl Amino Silane Li4
Lithium Methyl Amino Silane Li4 was prepared as follows:

(Formula Li4)

Reaction of Amino Methyl Silane Pr4 with Lithium

The reaction was performed in an inert atmosphere. Lithium powder (6.00 mg, 0.86 mmol) and compound Pr4 (0.20 mmol, 47.0 mg) were stirred overnight in 2 mL cyclohexane. The mixture was filtered to remove lithium and formed lithium chloride and the solvent was removed to yield a white solid. The solid was dissolved in $C_6D_6$ and the NMR-analysis revealed that 75% of Pr4 was converted to the lithiated compound Li4, additionally resonances for the starting material Pr4 could be detected.

$^1$H-NMR (400 MHz, 23° C., $C_6D_6$): δ=3.02 (m, 8H, $NCH_2$), 1.09 (t, 12H, $NCH_2CH_3$), 0.39 (s, 3H, SiMe), -1.65. (s, 2H, $LiCH_2$), ppm; $^{13}$C-NMR (101 MHz, 23° C., $C_6D_6$) δ=39.85 ($NCH_2$), 14.98 ($NCH_2CH_3$), 0.53 ($SiMe_2$), -10.96 (br, $LiCH_2$), ppm.

Preparation Step 2—Lithium Methyl Amino Silane*TMEDA I5

The reaction of Lithium Methyl Amino Silane Li4 with TMEDA was performed in situ according to the general procedure for the copolymerization of styrene and butadiene (see below). Therefore Lithium Methyl Amino Silane*TMEDA I5 was formed upon addition of Lithium Methyl Amino Silane Li4 to the polymerization vessel already comprising tetramethylethylene diamine (TMEDA), cyclohexane solvent; butadiene monomer and styrene monomer. The amounts of Lithium Methyl Amino Silane Li4, of TMEDA and of the monomers are listed in Table 4.

Preparation of Bis(bis(trimethylsilyl)phenyl)methyl lithium*TMEDA I6

Bis(bis(trimethylsilyl)phenyl)methyl lithium*TMEDA I6 was prepared as follows:

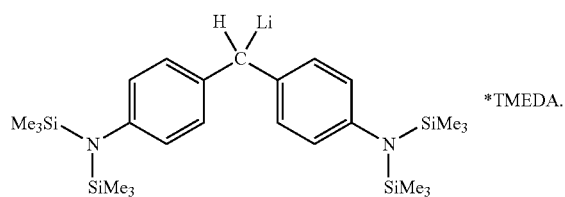

(Formula I6)

Reaction of Amino Methyl Silane Pr5 with n-Butyl Lithium

The reaction was performed in an inert atmosphere. 0.10 mmol, 50 mg of Pr5 was dissolved in $C_6D_6$ and 0.20 mmol, 23.0 mg TMEDA and 0.15 mmol, 9.60 mg n-BuLi were added. The mixture was heated at 60° C. for 2 days, NMR measurement revealed the complete conversion of Pr5 to the lithiated polymerization initiator compound 16.

$^1$H-NMR (400 MHz, 23° C., $C_6D_6$): δ=6.83 (m, 4H, Aryl-H), 6.70 (m, 4H, Aryl-H), 4.39 (s, 1H, $CH_2$), 0.27 (s, 36H, $SiMe_3$) ppm, additionally, signals for coordinated TMEDA could be detected at 1.94 and 1.90 ppm; $^{13}$C-NMR (101 MHz, 23° C., $C_6D_6$) δ=142.04 (Aryl-C), 131.66 (Aryl-C), 130.26 (Aryl-C), 116.67 (Aryl-C), 66.46 (CHLi), 2.65 ($SiMe_3$) ppm, additionally, signals for coordinated TMEDA could be detected at 57.17 and 45.57 ppm.

Preparation of Lithium Propyl Amino Disilane I7

Preparation Step 1—Lithium Propyl Amino Disilane Li5

Lithium Methyl Amino Silane Li5 was prepared as follows:

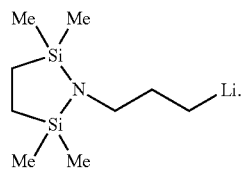

(Formula Li5)

Reaction of Amino Methyl Silane Pr6 with Lithium

The reaction was performed in an inert atmosphere. Lithium powder (9.00 mg, 1.30 mmol) and compound Pr6 (0.21 mmol, 50 mg) were stirred overnight in 3 mL cyclohexane. The mixture was filtered to remove lithium and formed lithium chloride and the solvent was removed under vacuum. The residue was dissolved in $C_6D_6$ and the NMR-analysis revealed the formation of the lithiated compound Li5, additionally no resonances for the starting material Pr6 could be detected.

$^1$H-NMR (400 MHz, 23° C., $C_6D_6$): δ=2.70-2.65 (m, $2H_1$, $NCH_2$), 1.47-1.41 (m, 2H, $CH_2CH_2CH_2$), 0.77-0.73 (m, 2H, $LiCH_2$), 0.69-0.65 (m, 4H, $Si(CH_2)_2Si$), 0.05 (s, 6H, $SiMe_2$), 0.03 (s, 6H, $SiMe_2$) ppm; $^{13}$C-NMR (101 MHz, 23° C., $C_6D_6$) δ=43.24 ($NCH_2$), 28.31 ($CH_2$), 12.35 (Si—$CH_2$), 11.11 ($LiCH_2$), 9.89 (Si—$CH_2$), -1.24 ($SiMe_2$), -1.82 ($SiMe_2$) ppm.

Preparation Step 2—Lithium Methyl Amino Silane*TMEDA I7

The reaction of Lithium Methyl Amino Silane Li5 with TMEDA was performed in situ according to the general procedure for the copolymerization of styrene and butadiene (see below). Therefore Lithium Methyl Amino Silane*TMEDA I7 was formed upon addition of Lithium Methyl Amino Silane Li5 to the polymerization vessel already comprising tetramethylethylene diamine (TMEDA), cyclohexane solvent; butadiene monomer and styrene monomer. The amounts of Lithium Methyl Amino Silane Li5, of TMEDA and of the monomers are listed in Table 4.

Preparation of Initiator System I8

The components methyl tris dimethylamino silane Pr7, sec. butyl lithium and triethylamine used to prepare the initiator system described in WO 2011/082277 are represented by Formula I8 below, and the initiator system was prepared according to the instructions given in said application:

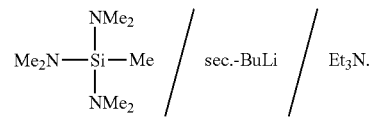

(Formula I8)

Reaction of Triamino Methyl Silane Pr7 with Sec. Butyl Lithium and Triethylamine The reaction was performed in an inert atmosphere. Sec.-BuLi (160 μL, 1.3 M solution solution in cyclohexane/hexane (92/8), 0.20 mmol) was added to a solution of tris(dimethylamino)methylsilane (41 μL, 0.20 mmol) and triethylamine (80 μL, 0.59 mmol). The mixture was heated at 50° C. for 2 hours. Cyclohexane was removed under reduced pressure and the liquid residue was dissolved in $C_6D_6$ and an NMR analysis was performed immediately. The $^1$H-NMR and $^{13}$C-NMR analyses revealed that no reaction took place and therefore only tris(dimethylamino)methylsilane, triethylamine, sec.-BuLi and cyclohexane could be detected.

Preparation of Initiator System I9

The components trimethyl dimethylamino silane Pr8, sec. butyl lithium and triethylamine used to prepare the initiator system described in WO 2011/082277 are represented by Formula I9 below, and the initiator system was prepared according to the instructions given in said application:

(Formula I9)

Reaction of Triamino Methyl Silane Pr8 with Sec. Butyl Lithium and Triethylamine The reaction was performed in an inert atmosphere. sec.-BuLi (160 μL, 1.3 M solution solution in cyclohexane/hexane (92/8), 0.20 mmol) was added to a solution of N,N-(diethylamino)trimethylsilane (38 μL, 0.20 mmol) and triethylamine (80 μL, 0.59 mmol). The mixture was heated at 50° C. for 2 hours. Cyclohexane was removed under reduced pressure and the liquid residue was dissolved in $C_6D_6$ and an NMR analysis was performed immediately. The $^1$H-NMR and $^{13}$C-NMR analyses revealed that no reaction took place and therefore only N,N-(Diethylamino)trimethylsilane, triethylamine, sec.-BuLi and cyclohexane could be detected.

Coupling Agents

Coupling Agent C1 (tin tetrachloride) was purchased from Aldrich.

$SnCl_4$ (Formula C1)

Coupling Agent C2 (tetramethoxy silane) was purchased from Aldrich.

$Si(OMe)_4$ (Formula C2)

Coupling Agent C3 (silicon tetrachloride) was purchased from Aldrich.

$Si(Cl)_4$ (Formula C3)

Chain End-Modifying Compounds

Chain End-Modifying Compound E1 was prepared by two preparation pathways as follows:

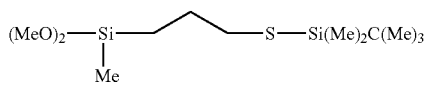

(Formula E1)

Preparation Pathway 1 (E1):

To a 100 mL Schlenk flask was charged 25 ml tetrahydrofuran (THF), 79.5 mg (10 mmol) lithium hydride, and subsequently, 1.18 g (10 mmol) gamma-mercaptopropyl (methyl) dimethoxysilane from the ABCR GmbH. The reaction mixture was stirred for 24 hours at room temperature, and another two hours at 50° C. Than tert-butyl dimethyl chloro silane (1.51 g (10 mmol)) was dissolved in 10 g THF, and the resulting solution was then added drop wise to the Schlenk flask. Lithium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 99% pure per GC, and therefore no further purification was necessary. A yield of 3.1 g (9.3 mmol) of Chain End-Modifying Compound E1 was obtained.

Preparation Pathway 2 (E1):

To a 100 mL Schlenk flask was charged 1.18 g (10 mmol) gamma-mercaptopropyl (methyl) dimethoxysilane from the ABCR GmbH, 25 ml tetrahydrofuran (THF), and subsequently, 0.594 g (11 mmol) sodium methanolate (NaOMe) dissolved in 10 mL THF. The reaction mixture was stirred for 18 hours at room temperature. Then tert-butyl dimethyl chloro silane (1.51 g (10 mmol)) was dissolved in 10 g THF, and the resulting solution was then added drop wise to the Schlenk flask. Sodium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 89% pure per GC. Further purification consisted in a fractionated distillation, and a yield of 2.6 g (7.9 mmol) of Chain End-Modifying Compound E1 was obtained.

Gamma-mercaptopropyl (methyl) dimethoxysilane Pr9 was purchased from the ABCR GmbH.

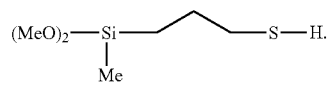

(Formula Pr9)

Chain End-Modifying Compound E2 was prepared as follows.

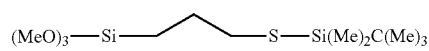

(Formula E2)

Preparation Pathway 1 (E2):

To a 100 mL Schlenk flask was charged 25 ml tetrahydrofuran (THF), 79.5 mg (10 mmol) lithium hydride, and subsequently, 1.96 g (10 mmol) gamma-mercaptopropyl trimethoxy silane [Silquest A-189] from the Cromton GmbH. The reaction mixture was stirred for 24 hours at room temperature, and another two hours at 50° C. Than tert-butyl dimethyl chloro silane (1.51 g (10 mmol)) was dissolved in 10 g THF, and the resulting solution was then added drop wise to the Schlenk flask. Lithium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 99% pure per GC, and therefore no further purification was necessary. A yield of 2.9 g (9.2 mmol) of Chain End-Modifying Compound (E2) was obtained.

Alternative Preparation Pathway 2 (E2):

To a 100 mL Schlenk flask was charged 1.96 g (10 mmol) gamma-mercaptopropyl trimethoxy silane [Silquest A-189] from the Cromton GmbH, 25 ml tetrahydrofuran (THF), and subsequently, 0.594 g (11 mmol) sodium methanolate (NaOMe) dissolved in 10 mL THF. The reaction mixture was stirred for 18 hours at room temperature. Then tert-butyl dimethyl chloro silane (1.51 g (10 mmol)) was dissolved in 10 g THF, and the resulting solution was then added drop wise to the Schlenk flask. Sodium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 89% pure per GC. Further purification consisted in a fractionated distillation, and a yield of 2.2 g (7.2 mmol) of Chain End-Modifying Compound E2 was obtained.

Gamma-mercaptopropyl trimethoxy silane Pr10 was purchased from Cromton GmbH.

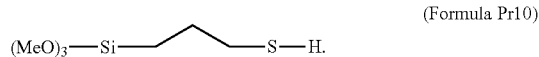
(Formula Pr10)

Chain End-Modifying Compound E3 was prepared by two preparation pathways as follows:

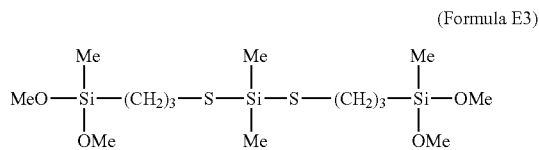
(Formula E3)

Preparation Pathway 1:

To a 100 mL Schlenk flask was charged 50 ml tetrahydrofuran (THF), 159 mg (20 mmol) lithium hydride, and subsequently, 3.6 g (20 mmol) gamma-mercaptopropyl (methyl) dimethoxysilane from the ABCR GmbH. The reaction mixture was stirred for 2 hours at 65° C. The reaction mixture was allowed to cool down to room temperature. Then a solution of dimethyl dichloro silane (1.30 g (10 mmol)) in 10 g THF was then added drop wise to the Schlenk flask. The reaction mixture was warmed up to 65° C. and kept at this temperature for 2 hours. Subsequently the THF solvent was removed under vacuum (reduced pressure) from the resulting mixture at room temperature and the residue was dissolved in 50 mL cyclohexane. Precipitated lithium chloride was separated from the reaction product dissolved in the cyclohexane by filtration. The cyclohexane solvent was removed under vacuum (under reduced pressure). The resulting colorless liquid solution proved to be 95% pure per GC, and therefore no further purification was necessary. A yield of 3.9 g (9.3 mmol) of Chain End-Modifying Compound E3 was obtained.

Preparation Pathway 2:

To a 250 mL Schlenk flask was charged 150 mL cyclohexane, 9.02 g (50 mmol) gamma-mercaptopropyl (methyl) dimethoxysilane from the ABCR GmbH, and subsequently, 3.23 g (25 mmol) dichlorodimethylsilane from Sigma-Aldrich. The reaction mixture was stirred overnight at 65° C. The reaction mixture was allowed to cool down to room temperature. The mixture was filtered and all volatiles were removed under reduced pressure to yield 9.20 g (88%) of compound E3. The resulting colorless liquid solution proved to be 95% pure per NMR, and therefore no further purification was necessary.

$^1$H-NMR (400 MHz, 23° C., $C_6D_6$): δ=3.32 (s, 12H, SiOCH$_3$), 2.57 (t, 4H, S—CH$_2$), 1.70 (m, 4H, CH$_2$CH$_2$CH$_2$), 0.66 (m, 4H, CH$_2$SiMe(OMe)$_2$), 0.43 (s, 6H, Si(OMe)CH$_3$), 0.01 (s, 6H, Si(OCH3)$_2$CH$_3$) ppm; $^{13}$C (101 MHz, 23° C., $C_6D_6$): δ=49.96 (OCH$_3$), 30.90 (S—CH$_2$), 26.67 (CH$_2$CH$_2$CH$_2$), 13.15 (CH$_2$SiMe(OMe)$_2$), 2.06 (SiCH$_3$), −5.48 (SiCH$_3$) ppm.

Chain End-Modifying Compound E4 was prepared by two preparation pathways as follows:

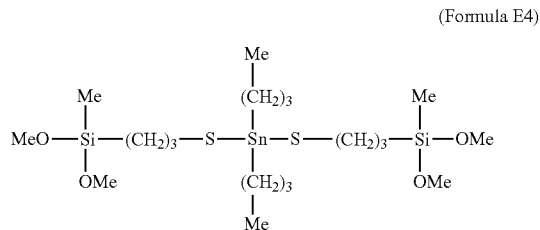
(Formula E4)

Preparation Pathway 1:

To a 100 mL Schlenk flask was charged 50 ml tetrahydrofuran (THF), 159 mg (20 mmol) lithium hydride, and subsequently, 3.6 g (20 mmol) gamma-mercaptopropyl (methyl) dimethoxysilane from the ABCR GmbH. The reaction mixture was stirred for 2 hours at 65° C. The reaction mixture was allowed to cool down to room temperature. Then a solution of di-n-butyl dichloro silane (3.3 g (10 mmol)) in 10 g THF was then added drop wise to the Schlenk flask. The reaction mixture was warmed up to 65° C. and kept at this temperature for 2 hours. Subsequently the THF solvent was removed under vacuum (reduced pressure) from the resulting mixture at room temperature and the residue was dissolved in 50 mL cyclohexane. Precipitated lithium chloride was separated from the reaction product dissolved in the cyclohexane by filtration. The cyclohexane solvent was removed under vacuum (under reduced pressure). The resulting colorless liquid solution proved to be 89% pure per GC, and therefore no further purification was necessary. A yield of 5.5 g (8.9 mmol) of Chain End-Modifying Compound E4 was obtained.

Preparation Pathway 2:

To a 100 mL Schlenk flask was charged 100 ml cyclohexane, 2.02 g (20 mmol) triethyl amine, and 3.6 g (20 mmol) gamma-mercaptopropyl (methyl) dimethoxysilane from the ABCR GmbH. The reaction mixture was stirred for 5 min at room temperature. Then a solution of di-n-butyl dichloro silane (3.30 g (10 mmol)) in 20 g cyclohexane was then added drop wise to the Schlenk flask. The reaction mixture was warmed up to 65° C. and kept at this temperature for 2 hours. Precipitated triethyl ammonium chloride was separated from the reaction product dissolved in the cyclohexane by filtration. Then cyclohexane solvent was removed under vacuum (under reduced pressure). The resulting colorless liquid solution proved to be 95% pure per GC, and therefore no further purification was necessary. A yield of 5.9 g (9.5 mmol) of Chain End-Modifying Compound E4 was obtained.

$^1$H-NMR (400 MHz, 23° C., $C_6D_6$): δ=3.35 (s, 12H, SiOCH$_3$), 2.82 (t, 4H, S—CH$_2$CH$_2$CH$_2$—Si), 1.87 (m, 4H, CH$_2$CH$_2$CH$_2$—Si), 1.61 (m, 4H, SnCH$_2$CH$_2$CH$_3$), 1.30 (m, 8H, SnCH$_2$CH$_2$CH$_2$ClH$_3$), 0.83 (t, 6H, SnCH$_2$CH$_2$CH$_2$CH$_3$), 0.78 (t, 4H, S—CH$_2$CH$_2$CH$_2$—Si), 0.06 (s, 6H, Si(OMe)$_2$CH) ppm; $^{13}$C (101 MHz, 23° C., $C_6D_6$): δ=49.95 (OCH$_3$), 31.01 (S—CH$_2$CH$_2$CH$_2$—Si), 28.70 (SCH$_2$CH$_2$CH$_2$) & (SnCH$_2$CH$_2$CH$_2$CH$_3$), 27.06 (SnCH$_2$CH$_2$CH$_2$CH$_3$), 17.90 (SnCH$_2$CH$_2$CH$_2$CH 3), 13.76 (SnCH$_2$CH$_2$CH$_2$CH$_3$), 13.21 (S—CH$_2$CH$_2$CH$_2$—Si), −5.47 (SiCH$_3$) ppm.

Randomizers

TMEDA (N,N,N',N'-Tetramethyl-ethylene-1,2-diamine) was purchased from Aldrich and was dried with molecular sieve prior to use.

DTHFP (DTHFP (2,2-di(2-tetrahydrofuryl)propane) was purchased from Pennakem and was dried with molecular sieve, pore size 4 Å, prior to use.

Homopolymerization of 1,3-Butadiene (Examples A, B and C, D):

Polymerizations for Examples A, B and C, D were performed in a double wall, two liter steel reactor, which was purged with nitrogen, before the addition of organic solvent, monomers, polar coordinator compound, initiator compound or other components. The polymerization reactor was tempered to 50° C., unless stated otherwise. The following components were than added in the following order: cyclohexane solvent (500 grams); tetramethylethylene diamine (TMEDA) (45.0 mmol) as polar coordinator compound, butadiene monomer, and the mixture was allowed to stir for one hour. N-butyl lithium (50.0 mmol) was added to start the polymerization reaction. The polymerization was performed at 50° C. for approximately 2 hours, after which time, a part of the polymer solution (66.6 wt % or 50 wt %) was removed from the reactor, and separately worked up as described below. Subsequently, the Chain End-Modifying Compound E2 or E1 was added. Subsequently the polymer solution was stirred for an additional 45 minutes at 50° C. For Examples B and D, no modifier was added. For the termination of the polymerization process, the polymer solution was transferred, after one hour, into a separate double wall, steel reactor, containing 50 mL methanol, and Irganox 1520 as stabilizer for the polymer (one liter of methanol contained two grams of Irganox). This mixture was stirred for 15 minutes. The polymerization solvent and other volatiles were then removed via vacuum.

Examples A & B

The polymerization reaction (for Example A) was performed using 54.1 g (1.00 mol) butadiene. After the removal of 66.6 wt % of the polymer solution, 5.91 grams (25.0 mmol) of Chain End-Modifying Compound E2 was added to the polymerization reactor. The same preparation was used for Example B, except that no modifier was added. The final polymer is characterized in Table 2.

Examples C & D

The polymerization reaction was performed using 10.0 g (0.185 mol) butadiene. After the removal of 50 wt % of the polymer solution, 12.5 mmol of Chain End-Modifying Compound E1 was added to the polymerization reactor. The same preparation was used for Example D, except that no modifier was added. The final polymer is characterized in Table 2.

TABLE 2

SEC Characterizations, $^1$H NMR Characterizations, and Elemental Analysis on Final Polymer***

| Ex. | Modifier | Mw [g/mol] | Mn [g/mol] | —S content [mmol/g polybutadiene]* | —OMe content [mol %]** | —SiMe$_3$ content [mmol/g polybutadiene]** |
|---|---|---|---|---|---|---|
| A | E2 | 4,560 | 3,460 | 0.20 | 0.0 | 0.17 |
| B | — | 2,350 | 2,080 | 0.0 | 0.0 | 0.0 |
| C | E1 | 930 | 575 | 0.83 | 0.1 | 0.89 |
| D | — | 520 | 430 | 0.0 | 0.0 | 0.0 |

*Elemental Analysis for Sulfur (X-Ray Fluorescence Spectroscopy)
**1 H NMR Spectroscopy
***GPC—Method B GC-MS investigation of Example A confirmed the existence of trimethyl silyl groups (—SiMe$_3$) (m/e=73), exemplary in three different polymer fractions, at retention times of 13.17 minutes, 13.25 minutes and 22.04, respectively. The (—SiMe$_3$) fragment was found in the majority of the polymer fractions, indicating the existence of at least one (—SiMe$_3$) group in the majority of the polymer chains.

As a separate study, an effective removal of the (—SiMe$_3$) protective group was demonstrated by first preparing hexadecyl-trimethylsilyl-sulfide, followed by the removal of (—SiMe$_3$) group with HCl. More specifically, 5.1 g (20 mmol) hexadecylthiol was dissolved in 25 mL cyclohexane. Triethylamine (2.15 g (21.25 mmol)) was then added, followed by 4.47 g (41.25 mmol) chloro-trimethyl-silane in 25 mL cyclohexane. The resulting reaction mixture was stirred for 24 hours, and than heated at 60° C. for three hours. The resulting solution was filtered, and the cyclohexane solvent removed via vacuum. Hexadecyl-trimethylsilyl-sulfide was formed (yield: 6.6 g (20.0 mmol)). The (—SiMe$_3$) group was confirmed via NMR spectroscopy (signal appeared in the $^1$H-NMR spectra at 0.23 ppm). Hexadecyl-trimethylsilyl-sulfide (1 gram (mmol)) was dissolved in 15 mL cyclohexane, and hydrochloric acid (2 grams, 36%) in 10 mL ethanol was added, and the mixture was stirred for 15 hours at room temperature. After removal of the organic layer through phase separation and extraction, the organic phase was dried using magnesium sulfate and filtrated. Removal of the organic solvent, and most of the formed hexachlorodisiloxane side product, via vacuum, led to the isolation of hexadecylthiol. As expected, the (—SiMe$_3$) signal in the $^1$H-NMR spectra at 0.23 ppm disappeared, and a new (—SiMe$_3$) signal of very low intensity at 0.13 ppm appeared, indicating the presence of a hexachlorodisiloxane side product.

Homopolymerization of Isoprene—Amino Silane Modified Polyisoprene

Preparation of (A) Amino Silane Modified Low Molecular Weight Polyisoprene (PI) Prior to Treatment with Water Procedure for Preparation of Low Molecular Weight Polyisoprene of the Generalized Structure Et$_2$N—Si(Me)-CH$_2$—PI The reaction was performed in an inert atmosphere in a dry box. Isoprene (5 mL, 50 mmol) was added to a solution of the amino silane polymerization initiator I2a, formed from lithium methyl amino silane Li1 (1 mmol) and TMEDA (300 μL, 2 mmol) in cyclohexane (30 mL), to start the isoprene polymerization. After 3 hours at room temperature the polymerization was quenched by the addition of methanol (50 μL, 1.25 mmol). A minor fraction of the polymer solution (5 ml) was separated and all volatiles were removed in the vacuum. The resulting polymer was characterized by $^1$H-NMR, $^{29}$Si-NMR and GPC analyses.

(B) Silanol Modified Low Molecular Weight Polyisoprene after Treatment with Water Procedure for the Hydrolysis of Amino Silane Modified Low Molecular Weight Polyisoprene of the Generalized Structure Et$_2$N—Si(Me$_2$)-CH$_2$—PI leading to Silanol Modified Low Molecular Weight Polyisoprene of the Generalized Structure HO—Si(Me$_2$)-CH$_2$—PI To the main fraction of the solution of the oligomer (A) was added 5 mL of water. The mixture was refluxed for 30 min. The organic phase was separated and analyzed by NMR-spectroscopy.

(C) Attempt to Polymerize Isoprene in the Absence of a Lewis Base, Such as TMEDA and DTHFP The reaction was performed in an inert atmosphere in a dry box. Isoprene (5 mL, 50 mmol) was added to a solution of the lithium methyl amino silane Li1 (1 mmol) in cyclohexane (30 mL), to start the isoprene polymerization. After 3 hours at room temperature the polymerization solution was quenched by the addition of 100 mL methanol. No precipitation or separation of polymer was observed. Accordingly the polymerization of isoprene could not be initiated without having a Lewis base such as TMEDA or DTHFP present.

The low molecular weight polymers prepared according to (A) and (B) were characterized by $^1$H-NMR, $^{29}$Si-NMR and GPC analyses:

Amino Silane Modified Polyisoprene (A):

$^1$H-NMR (400 MHz, 23° C., CDCl$_3$): δ=2.76 (q, NCH$_2$), 0.94 (t, NCH$_2$CH$_3$) 0.02 (br, SiCH$_3$) ppm; furthermore the characteristic resonances from the isoprene units could be detected.

$^{29}$Si-NMR (79 MHz, 23° C., CDCl$_3$): δ=3.0 (Si-NEt$_2$) ppm

Silanol Modified Polyisoprene (B):

$^1$H-NMR (400 MHz, 23° C., CDCl$_3$): δ=2.67 (q, NCH$_2$), 1.13 (t, NCH$_2$CH) 0.12-0.07 (m, SiCH$_3$) ppm; furthermore the characteristic resonances from the isoprene units could be detected.

$^{29}$Si-NMR (79 MHz, 23° C., CDCl$_3$): δ=15.9 (Si—OH) ppm.

TABLE 3

Polymer Characteristics

| Initiator | Mw [g/mol] | Mn [g/mol] | Mp1 [g/mol] | 1,2-content [%] | 3,4-content [%] | 1,4-content [%] |
|---|---|---|---|---|---|---|
| Polymer (A) | 12500 | 10100 | 15300 | 13.5 | 64.0 | 22.5 |
| Polymer (B) | 13100 | 9800 | 15500 | 13.1 | 65.3 | 21.6 |

The $^{29}$Si-NMR spectrum of the Amino Silane Modified Polyisoprene (A) exhibits a signal at 3.0 ppm. This chemical shift is characteristic for a silicon atom which is substituted by an amine and three alkyl chains, e.g. the silicon atom of the N,N-(diethylamino)trimethylsilane has a chemical shift of 4.8 ppm (comparative statement from spectral data source of Wiley Subscription Services; spectrum ID cc-01-SI_NMR-873). The hydrolysis of Polymer (A) leads to the Polymer (B). The $^{29}$Si-NMR spectrum show the complete disappearance of the characteristic signal of Polymer (A) at 3.0 ppm and a new signal has appeared with a chemical shift at 15.9 ppm. This signal is characteristic for a silicon atom which is substituted by a hydroxy group and three alkyl chains, e.g. the silicon atom of trimethylsilanol has a chemical shift of 15.1 ppm (comparative statement measured on trimethylsilanol purchased from Sigma Aldrich). Additionally, a significant change in the $^1$H-NMR spectrum could be observed. The signals at 2.76 and 0.94 ppm, typical for the protons of the ethyl group in the Et$_2$N—Si(Me$_2$)-CH$_2$-polymer chain end moiety, are not present in case of modified polyisoprene (B) and therefore two signals at 2.67 and 1.13 ppm were be observed which could be assigned to the diethylamine, which is the hydrolysis product of the Amino Silane Modified Polyisoprene (A) and water, the hydrolysis from (A) furthermore yielding the HO—Si(Me$_2$)-CH$_2$-chain end modified polyisoprene (B).

Batchwise Copolymerization of 1,3-Butadiene with Styrene (Examples 1-21)

The co-polymerizations were performed in a double wall, 10 liter steel reactor, which was first purged with nitrogen, before the addition of organic solvent, monomers, polar coordinator compound, initiator compound or other components. The polymerization reactor was tempered to 60° C., unless stated otherwise. The following components were then added in the following order: cyclohexane solvent (4600 grams); butadiene monomer, styrene monomer, tetramethylethylene diamine (TMEDA), and the mixture was stirred for one hour, followed by titration with n-butyl lithium to remove traces of moisture or other impurities. The polymerization initiator precursor compound (Li1-Li4) or the amino silane polymerization initiator compound (I1, I6-I9) was added into the polymerization reactor to initiate the polymerization reaction. The polymerization was performed for 80 minutes, not allowing the polymerization temperature to exceed 60° C. Afterwards, 0.5% of the total butadiene monomer amount was added, followed by the addition of the coupling agent, unless stated otherwise (see Table 4). The mixture was stirred for 20 minutes. Subsequently, 1.8% of the total butadiene monomer amount was added, followed by the addition of the chain end modifier, unless stated otherwise. For the termination of the polymerization process, the polymer solution was transferred, after 45 minutes, into a separate double wall, steel reactor, containing 100 mL ethanol, 1.4 g of concentrated HCl (concentration 36%), and 5 g IRGANOX 1520 as stabilizer for the polymer. This mixture was stirred for 15 minutes. The resulting polymer solution was than stripped with steam for one hour to remove solvent and other volatiles, and dried in an oven at 70° C. for 30 minutes, and then additionally for one to three days, at room temperature.

The resulting second and vulcanized polymer composition and several of its properties are summarized in Tables 8 to 11 below. Unless stated otherwise, quantities are expressed in mmols. Examples prepared under identical polymerization conditions (in the same polymerization reactor, on the same day, by the same operator) are designated with identical letters adjacent to the Example number (e.g. 1A, 2A). Unless stated otherwise, monomer conversions of more then 99% by weight were achieved for all experiments listed in Table 4. Monomer Conversion was measured as polymer solid content representing the weight of polymer after removal of the polymerization solvent and potentially available volatile components. The corresponding polymer solution sample was taken from the polymerization reactor shortly prior to termination of the polymerization process.

The use of a dash "-" in the tables below indicates that no component was added.

TABLE 4

Composition of Examples—amounts of reagents for polymerization.

| Ex. | N-butyl lithium initiator or Amino silane initiator or initiator precursor (mol) | Coupling agent (mmol) | Chain End Modifier (mmol) | Buta-diene (mol) | Sty-rene (mol) | TMEDA (mol) |
|---|---|---|---|---|---|---|
| 1 (Ref) | (I1) 4.732 | (C1) 0.335 | (E1) 4.164 | 12.95 | 1.791 | 9.484 |
| 2 | (Li1) 4.236 | (C1) 0.303 | (E1) 3.756 | 12.809 | 1.774 | 8.677 |
| 3 | (Li1) 4.521 | (-) | (E1) 3.926 (E2) 0.513 | 12.84 | 1.775 | 8.979 |
| 4 (CEx) | (16) 5.293 | (C1) 0.262 | (E1) 3.343 | 11.01 | 1.531 | 1.887 |
| 5 (CEx) | (17) 4.331 | (C1) 0.303 | (E1) 3.805 | 12.78 | 1.771 | 8.689 |

TABLE 4-continued

Composition of Examples—amounts of reagents for polymerization.

| Ex. | N-butyl lithium initiator or Amino silane initiator or initiator precursor (mol) | Coupling agent (mmol) | Chain End Modifier (mmol) | Buta-diene (mol) | Sty-rene (mol) | TMEDA (mol) |
|---|---|---|---|---|---|---|
| 6 (Ref) | (I1) 3.649 | (-) | (-) | 13.05 | 1.805 | 7.531 |
| 7 (Ref) | (I1) 3.472 | (-) | (E3) 4.223 | 13.02 | 1.802 | 7.080 |
| 8 | (Li1) 3.589 | (-) | (E3) 4.471 | 12.91 | 1.784 | 7.240 |
| 9 (Ref) | (Li1) 3.620 | (-) | (-) | 13.00 | 1.801 | 7.279 |
| 10 (CEx) | (18) 3.615 | (-) | (-) | 12.99 | 1.800 | 7.253 |
| 11 (CEx) | (19) 3.600 | (-) | (-) | 12.95 | 1.790 | 7.261 |
| 12 (Ref) | (I1) 3.493 | (-) | (E1) 4.199 | 13.01 | 1.798 | 7.263 |
| 13 | (Li1) 3.673 | (-) | (E1) 4.310 | 12.89 | 1.783 | 7.090 |
| 14 (Ref) | (I1) 4.436 | (-) | (E4) 5.621 | 13.01 | 1.798 | 9.222 |
| 15 | (Li1) 4.852 | (-) | (E4) 5.822 | 12.84 | 1.775 | 9.594 |
| 16 (Ref) | (I1) 1.994 | (E2) 0.417 | (E1) 1.896 | 10.57 | 1.468 | 8.855 |
| 17 | (Li1) 1.852 | (E2) 0.349 | (E1) 1.647 | 10.49 | 1.457 | 7.458 |
| 18 | (Li2) 3.593 | (-) | (E3) 4.313 | 13.55 | 1.796 | 7.059 |
| 19 | (Li3) 3.597 | (-) | (E3) 4.319 | 12.93 | 1.791 | 7.304 |
| 20 | (I6) 3.531 | (-) | (E3) 4.234 | 13.03 | 1.802 | 7.057 |
| 21 | (Li4) 3.336 | (-) | (E1) 4.184 | 11.78 | 1.630 | 6.727 |

TABLE 5

Polymer Characterizations

| Example | Mw [g/mol] | Mn [g/mol] | Mp1 [g/mol] | Coupling Rate[A] [%] | Mooney* viscosity [MU] | Mooney** Viscosity [MU] | Vinyl content[B] [wt %] | Styrene content[C] [wt %] |
|---|---|---|---|---|---|---|---|---|
| 1 (Ref) | 446002 | 323287 | 293615 | 25.1 | 55.0 | (-) | 62.1 | 21.7 |
| 2 | 377389 | 284425 | 283053 | 16.9 | 48.3 | (-) | 60.2 | 22.3 |
| 3 | 355639 | 290287 | 292477 | 16.9 | 51.0 | (-) | 62.0 | 20.8 |
| 4 (CEx) | 341908 | 240220 | 302056 | 10.4 | 41.6 | (-) | 58.2 | 27.0 |
| 5 (CEx) | 392362 | 286256 | 292428 | 19.0 | 55.4 | (-) | 61.6 | 20.24 |
| 6 (Ref) | 366657 | 332209 | 373048 | (-) | 70.9 | (-) | 63.0 | 20.8 |
| 7 (Ref) | 413766 | 362738 | 398247 | 5.5 | 80.0 | (-) | 63.1 | 20.8 |
| 8 | 431784 | 348031 | 371179 | 12.2 | 79.6 | (-) | 61.2 | 21.3 |
| 9 (Ref) | 380199 | 324194 | 390423 | 1.7 | 74.5 | (-) | 60.9 | 21.5 |
| 10 (CEx) | 361001 | 322045 | 370348 | (-) | 69.1 | (-) | 60.6 | 22.1 |
| 11 (CEx) | 385270 | 344906 | 392180 | (-) | 84.2 | (-) | 61.1 | 20.5 |
| 12 (Ref) | 380189 | 338209 | 369008 | 3.6 | 72.8 | (-) | 63.3 | 20.8 |
| 13 | 370513 | 327625 | 367373 | (-) | 64.2 | (-) | 61.8 | 21.1 |
| 14 (Ref) | 447310 | 352494 | 284193 | 54.1 | 87.2 | (-) | 63.3 | 20.7 |
| 15 | 439053 | 333542 | 295549 | 46.9 | 89.4 | (-) | 61.8 | 21.1 |
| 16 (Ref) | 709317 | 527700 | 540683 | 33.9 | (-) | 56.7 | 63.0 | 21.4 |
| 17 | 708690 | 527157 | 556645 | 29.5 | (-) | 56.2 | 64.1 | 21.1 |
| 18 | 464830 | 351249 | 340035 | 12.7 | 94.5 | (-) | 61.9 | 20.1 |
| 19 | 415637 | 348732 | 363937 | 11.6 | 81.2 | (-) | 61.9 | 21.2 |
| 20 | 428792 | 322940 | 382454 | 9.9 | 73.0 | (-) | 61.7 | 21.7 |
| 21 | 364937 | 311770 | 373792 | 1.9 | 68.8 | (-) | 62.0 | 21.2 |

*Mooney viscosity of oil free grade
**Mooney viscosity of TDAE oil containing grade
[A]determined by SEC
[B]vinyl content is that of the 1,2-polybutadiene unit content of the final copolymer, and is determined by IR Spectroscopy
[C]styrene content of the final copolymer, and is determined by IR Spectroscopy Continuous Copolymerization of 1,3-Butadiene with Styrene
Reactor Conditions The following example was performed by means of three continuous stirred tank reactors (CSTRs) connected in series. Each reactor had a volume of 5.8 liter, and was equipped with a helicoidal stirrer, suitable for mixing of high viscous solutions, the speed of the stirrer during all trials was 200 rpm. External water circulation in the reactor walls regulated the desired temperature. The reagents required for polymerization (styrene, butadiene, cyclohexane, DTHFP and lithium initiator precursor compound Li1 were fed into the head of the first reactor with mass flow-meters. Each flow-meter regulated the desired feed, and guaranteed a constant flow of the reagent. Cyclohexane was purified by passing it through an alumina column. The total monomer content in the cyclohexane solution was 12%.

In the description of the experiment the term "active initiator" (I2b formed from Li1 and DTHFP in situ) refers to the amount of initiator that takes part in the polymerization reaction and that is not deactivated by impurities contained in the reaction medium. The term "excess initiator" (I2b formed from Li1 and DTHFP in situ) refers to the amount of initiator that is charged to deactivate the impurities present in the system.

Continuous Copolymerization Example 1 (CCE 1)
Reagents

Cyclohexane (distilled) was used as a solvent. 1,3-butadiene (distilled) and styrene (dried via $CaH_2$) were used as monomers. DTHFP and 1,2-butadiene were diluted in cyclohexane. Initiator I2b, resulting from the reaction of initiator precursor Li with DTHFP inside of the polymerization reactor (1), was used as anionic initiator. Modifier E2 was used as chain end-modifying agent.

CCE 1 Description:

A styrene/butadiene copolymerization was performed using three reactors connected in series.

Both, the first and the second reactor, were used for the polymerization. Chain end modifier E2 was added in the third reactor. During the polymerization the E2/Li molar ratio amounted to 0.580 and the DTHFP/Li1 (polymerization active component ratio) molar ratio amounted to 2.610. The following amounts were added into the first polymerization reactor: 1.827 g/min styrene, 6.873 g/min butadiene, 63.8 g/min cyclohexane, 0.0588 mmol/min Li1 (component of the active initiator I2b), 0.02642 mmol/min Li1 (component of the initiator used to deactivate impurities); 0.1535 mmol/min DTHFP.

Modifier E2 was added in the third polymerization reactor with a flow rate of 0.03410 mmol/min (conc. of Modifier E2 solution 0.003501 mol/l). The temperature of the first reactor amounted to 68° C. and the temperature of the second and the third reactor amounted to 70° C. The residence time was 60 minutes in each reactor.

A total conversion of 97.78% was obtained at the outlet of the first reactor and a complete monomer conversion (no monomer could be detected by GC-Analysis in the polymer solution) was obtained at the outlet of both, the second and third reactor.

Methanol as terminating agent and IRGANOX 1520 (0.15 phr) as antioxidant were added to the polymeric solution in the line going out of the third reactor. The polymers coming out of the first and the second reactors were analyzed by GPC (with a polystyrene calibration). The following results were determined for the copolymer removed from the first polymerization reactor: Mn=221,204 g/mol, Mw=412,572 g/mol, (Mw/Mn)=1.870. The following results were determined for the copolymer removed from the second polymerization reactor: Mn=219,913 g/mol, Mw=406,230 g/mol, (Mw/Mn)=1.900. The following results were determined for the polymer obtained in the third polymerization reactor: Mn=251,372 g/mol, Mw=479,133 g/mol, (Mw/Mn)=1.910.

The microstructure was determined by $^1$H-NMR. The following results were determined for the polymer at the outlet of the first polymerization reactor: 20.5 wt % styrene (based on the total monomer concentration of the copolymer), 66.5 wt % vinyl (1,2-polybutadiene, calculated on the butadiene fraction of the copolymer).

The following results were obtained for the polymer in the second polymerization reactor: 20.4 wt % styrene (based on the total monomer concentration of the copolymer), 66.5 wt % vinyl (1,2-polybutadiene, calculated on the butadiene fraction of the copolymer).

The following results were obtained for the polymer in the third polymerization reactor: 20.3 wt % styrene (based on the total monomer concentration of the copolymer), 66.5 wt % vinyl (1,2-polybutadiene, calculated on the butadiene fraction of the copolymer).

The Mooney Viscosity (ML 1+4) of the finalized copolymer (measured after coagulation of a BHT stabilized polymer solution in ethanol and drying the rubber crumbs for 5 minutes on a mill at 120° C.) was 42.1 MU.

Continuous Copolymerization Example 2 (CCE 2)
Reagents

Cyclohexane (distilled) was used as a solvent. 1,3-butadiene (distilled) and styrene (dried via $CaH_2$) were used as monomers. DTHFP was diluted in cyclohexane. Initiator I2b, resulting from the reaction of initiator precursor Li1 with DTHFP, was used as anionic initiator. Coupling agent C3 was used for polymer chain coupling.

CCE 2 Description

A styrene/butadiene copolymerization was performed using three reactors connected in series. Both, the first and the second reactor, were used for the monomer polymerization. Coupling agent C3 was added into the third reactor. During the polymerization the C3/Li1 molar ratio amounted to 0.381 and the DTHFP/Li1 molar ratio (polymerization active component ratio) to 2.540. The following amounts were added into the first polymerization reactor: 1.827 g/min styrene, 6.873 g/min butadiene, 63.8 g/min cyclohexane, 0.0604 mmol/min Li1(component of the active initiator I2b); 0.02485 mmol/min Li1 (component of the initiator used to deactivate impurities); 0.1535 mmol/min DTHFP.

C3 was added in the third polymerization reactor with a flow rate of 0.02302 mmol/min (conc. of C3 solution: 0.002709 mol/l). The temperature of the first reactor amounted to 68° C. and the temperature of the second and the third reactor amounted to 70° C. The residence time was 60 minutes in each reactor.

A total conversion of 97.55% was obtained at the outlet of the first reactor and a complete monomer conversion (no monomer detected in the polymer solution by GC-Analysis) was obtained at the outlet of both, the second and third reactor.

Methanol as terminating agent and IRGANOX 1520 (0.15 phr) as antioxidant were added to the polymeric solution in the line out of the third reactor. The polymers coming out of the first, the second and the third reactor were analyzed by GPC (with a polystyrene calibration). The following results were obtained for the polymer obtained at the outlet of the first polymerization reactor: Mn=214,931 g/mol, Mw=401,196 g/mol, (Mw/Mn)=1.870. The following results were obtained for the polymer obtained at the outlet of the second polymerization reactor: Mn=217,945 g/mol, Mw=411,600 g/mol, (Mw/Mn)=1.890. The following results were obtained for the polymer obtained at the outlet of the third polymerization reactor: Mn=276,246 g/mol, Mw=600,799 g/mol, (Mw/Mn)=2.170.

The microstructure was determined by $^1$H-NMR. The following results were obtained for the polymer at the outlet of the first polymerization reactor: 20.4 wt % styrene) based on the total monomer concentration of the copolymer), 66.5 wt % vinyl (1,2-polybutadiene, calculated on the butadiene fraction of the copolymer).

The following results were obtained for the polymer in the second polymerization reactor: 20.4 wt % styrene (based on the total monomer concentration of the copolymer), 66.5 wt % vinyl (1,2-polybutadiene, calculated on the butadiene fraction of the copolymer).

The following results were obtained for the polymer in the third polymerization reactor: 20.3 wt % styrene (based on the total monomer concentration of the copolymer), 66.4 wt % vinyl (1,2-polybutadiene, calculated on the butadiene fraction of the copolymer).

The Mooney Viscosity (ML 1+4) of the finalized copolymer (measured after coagulation of a BHT stabilized polymer solution in ethanol and drying the rubber crumbs for 5 minutes on a mill at 120° C.) was 63.8.

Polymer Compositions

Polymer compositions were prepared by combining and compounding the components listed below in Table 6, in a 350 cc Banbury mixer, and vulcanized at 160° C. for 20 minutes.

Vulcanization process data and physical properties for the each composition example are provided in Tables 8 and 9.

TABLE 6

Polymer Composition using polymers 1-5B, 1C, 2C, 6-13D, 6E, 14E, 15E and 18-20J

| Components | | Amount (phr)[n] |
|---|---|---|
| Elastomeric polymer Example (solution styrene butadiene copolymer) | | 80.0 |
| High cis 1,4-polybutadiene | Buna cis 132-Schkopau[m] | 20.0 |
| Precipitated silica | Ultrasil 7000GR[f] | 80.0 |
| Silane | Si 75[f,i] | 6.9 |
| Stearic acid[j] | | 1.0 |
| Stabilizer system Ozone protecting wax Antiozonant | Antilux 654[h] Dusantox[g] 6PPD | 1.5 2.0 |
| Zinc oxide[k] | | 2.5 |
| Softener (Oil) | TDAE[e] | 20.0 |
| Sulfur[d,l] | | 1.4 |
| TBBS[b,d] | | 1.5 |
| DPG[c,d] | | 1.5 | a 2 stage mixing, Brabender 350S, Internal Banbury mixer
[b]N-tert-Butyl-2-benzothiazyl-sulfenamide; Rhein Chemie Rheinau GmbH
[c]Diphenylguanidine, Vulkacit D, Lanxess AG
[d]Second stage (curing system)
[e]VivaTec 500, Hansen & Rosenthal KG
[f]Evonic Degussa GmbH
[g]N-(1,3-dimethylbutyl)-N'-phenyl-1,4-benzenediamine, Duslo a.s.
[h]Light & ozone protective wax, Rhein Chemie Rheinau GmbH
[i]Bis(triethoxysilylpropyl)disulfan, sulfur equivalents per molecule: 2.35
[j]Cognis GmbH
[k]Grillo-Zinkoxid GmbH
[l]Solvay AG
[m]Styron Deutschland GmbH
[n]Based on sum weight of the styrene butadiene copolymer and high cis 1,4-polybutadiene Additional polymer compositions were prepared by combining and compounding the components listed below in Table 7, in a 350 cc Banbury mixer, and vulcanized at 160° C. for 20 minutes. Vulcanization process data and physical properties for the each composition example are provided in Tables 10 and 11.

TABLE 7

Polymer Composition using polymers 16F and 17F

| Components | | Amount (phr)[g] |
|---|---|---|
| Elastomeric polymer Example (solution styrene butadiene copolymer) | | 117.5 |
| High cis 1,4-polybutadiene | Buna cis 132-Schkopau[f] | 20.0 |
| Precipitated silica | U7000GR[e] | 80.0 |
| Silane | Si 75[e] | 6.9 |
| Stearic acid[e] | | 1.0 |
| Stabilizer system | | |
| Ozone protecting wax | Dusantox[e] 6 PPD | 2.0 |
| Antiozonant | Antilux 654[e] | 1.5 |
| Zinc oxide[e] | | 2.5 |
| Sulfur[d,e] | | 1.3 |
| TBBS[e,d] | | 1.6 |
| DPG[c,d] | | 1.9 | a 2 stage mixing, Brabender 350S, Banbury internal mixer
[c]Diphenylguanidine, Vulkacit D, Lanxess AG
[d]Second stage (vulcanization)
[e]Detailed specification see Table 6
[f]Dow Olefinverbund GmbH
[g]Based on sum weight of the styrene butadiene copolymer and high cis 1,4-polybutadiene

TABLE 8

Vulcanization Process Data & Silica Containing Polymer Vulcanizate Composition Property

| Example | TC 50 [min] | TC 90 [min] | TC 95 [min] | Heat build up [° C.] | DIN Abrasion 0.5 kg load [mm] |
|---|---|---|---|---|---|
| 1B (Ref.) | 6.77 | 16.91 | 21.92 | 117.0 | 129 |
| 2B | 7.21 | 16.38 | 21.24 | 107.3 | 119 |
| 3B | 7.29 | 16.37 | 21.33 | 104.7 | 128 |
| 4B (CEx) | 7.83 | 16.45 | 21.19 | 125.1 | 132 |
| 5B (CEx) | 5.78 | 15.78 | 20.99 | 122.0 | 143 |
| 1C (Ref) | 6.44 | 15.78 | 20.89 | 114.6 | 125 |
| 2C | 6.43 | 15.88 | 20.92 | 99.3 | 122 |
| 6D (Ref) | 7.51 | 16.24 | 21.14 | 126.8 | 152 |
| 7D (Ref) | 7.57 | 16.31 | 21.20 | 108.8 | 135 |
| 8D | 7.91 | 16.26 | 21.06 | 103.6 | 122 |
| 9D (Ref) | 7.76 | 16.44 | 21.20 | 109.2 | 135 |
| 10D (CEx) | 8.04 | 16.78 | 21.55 | 127.7 | 147 |
| 11D (CEx) | 7.42 | 15.77 | 20.68 | 122.8 | 152 |
| 12D (Ref) | 7.99 | 15.76 | 20.47 | 108.1 | 140 |
| 13D | 8.22 | 16.91 | 21.54 | 101.5 | 124 |
| 6E (Ref) | 7.00 | 15.50 | 20.50 | 124.6 | 129 |
| 14E (Ref) | 7.40 | 16.40 | 21.20 | 117.3 | 133 |
| 15E | 7.80 | 17.10 | 21.60 | 101.0 | 132 |
| 18J | 7.40 | 16.50 | 21.30 | 106.8 | 130 |
| 19J | 7.70 | 16.60 | 21.30 | 99.4 | 133 |
| 20J | 7.70 | 16.10 | 20.80 | 101.5 | 140 |

TABLE 9

Silica Containing Polymer Vulcanizate Composition Properties

| Example | Elongation at Break [%] | Tensile Strength [MPa] | Modulus 300 [MPa] | Tan δ at −10° C. | Tan δ at 0° C. | Tan δ at 60° C. | Temp. at Tan δ max [° C.] |
|---|---|---|---|---|---|---|---|
| 1B (Ref.) | 458 | 19.4 | 10.2 | 0.4632 | 0.3198 | 0.1232 | −22 |
| 2B | 407 | 20.7 | 11.3 | 0.5427 | 0.3350 | 0.0847 | −18 |
| 3B | 406 | 20.7 | 11.8 | 0.5304 | 0.3304 | 0.0761 | −18 |
| 4B (CEx) | 385 | 17.9 | 12.4 | 0.5842 | 0.3788 | 0.1042 | −16 |
| 5B (CEx) | 409 | 19.9 | 11.8 | 0.4633 | 0.3355 | 0.1168 | −20 |

TABLE 9-continued

Silica Containing Polymer Vulcanizate Composition Properties

| Example | Elongation at Break [%] | Tensile Strength [MPa] | Modulus 300 [MPa] | Tan δ at -10° C. | Tan δ at 0° C. | Tan δ at 60° C. | Temp. at Tan δ max [° C.] |
|---|---|---|---|---|---|---|---|
| 1C (Ref) | 396 | 18.6 | 12.0 | 0.4453 | 0.3250 | 0.1294 | -20 |
| 2C | 335 | 18.1 | 14.8 | 0.5289 | 0.3346 | 0.0801 | -18 |
| 6D (Ref) | 413 | 18.6 | 11.5 | 0.3480 | 0.2749 | 0.1286 | -22 |
| 7D (Ref) | 396 | 19.0 | 12.5 | 0.3934 | 0.2871 | 0.1002 | -22 |
| 8D | 360 | 19.2 | 14.3 | 0.4618 | 0.3111 | 0.0752 | -20 |
| 9D (Ref) | 422 | 19.9 | 11.7 | 0.4550 | 0.2926 | 0.0792 | -22 |
| 10D (CEx) | 480 | 20.0 | 10.2 | 0.3666 | 0.2787 | 0.1266 | -22 |
| 11D (CEx) | 425 | 19.2 | 11.7 | 0.3825 | 0.2761 | 0.1097 | -22 |
| 12D (Ret) | 405 | 18.8 | 11.3 | 0.4405 | 01941 | 0.0858 | -22 |
| 13D | 385 | 20.2 | 13.4 | 0.4792 | 0.3101 | 0.0688 | -22 |
| 6E (Ref) | 416. | 18.5 | 11.8 | 0.3683 | 0.2676 | 0.1170 | -22 |
| 14E (Ref) | 409 | 19.4 | 12.3 | 0.3843 | 0.2912 | 0.1285 | -22 |
| 15E | 363 | 19.2 | 13.6 | 0.5001 | 0.3000 | 0.0747 | -20 |
| 18J | 380 | 19.8 | 12.7 | 0.4555 | 0.2858 | 0.0694 | -24 |
| 19J | 385 | 21.4 | 13.5 | 0.4856 | 0.3005 | 0.0688 | -22 |
| 20J (CEx) | 383 | 19.2 | 13.2 | 0.4352 | 0.2972 | 0.0976 | -20 |

TABLE 10

Vulcanization Process Data & Silica Containing Polymer Vulcanizate Composition Properties (Oil Grade)

| Example | Compound Mooney [Mu] | TS 1 [min] | TS 2 [min] | TC 50 [min] | TC 90 [min] | TC 95 [min] | Heat build up [° C.] | DIN Abrasion 0.5 kg load [mm] |
|---|---|---|---|---|---|---|---|---|
| 16F (Ref) | 92.9 | 1.34 | 3.15 | 6.54 | 14.33 | 19.11 | 103.3 | 126 |
| 17F | 149.8 | 0.35 | 1.59 | 7.28 | 14.75 | 19.42 | 100.3 | 131 |

TABLE 11

Silica Containing Polymer Vulcanizate Composition Properties

| Example | Elongation at Break [%] | Tensile Strength [MPa] | Modulus 300 [MPa] | Tan δ at -10° C. | Tan δ at 0° C. | Tan δ at 60° C. | Temp. at Tan δ max [° C.] |
|---|---|---|---|---|---|---|---|
| 16F (Ref) | 430 | 18.5 | 10.7 | 0.4528 | 0.2970 | 0.0917 | -22 |
| 17F | 455 | 20.0 | 10.4 | 0.4955 | 0.3148 | 0.0805 | -20 |

Results

It was found that only amino silane polymerization initiators but not the lithium amino silane polymerization initiator precursor compounds were sufficiently active to start the polymerization reaction of isoprene. For example, amino silane polymerization initiator I2a (see the above procedure (A) for the preparation of amino silane modified low molecular weight polyisoprene) but not the lithium amino silane polymerization initiator precursor compound Li1(see the above procedure (C) for the preparation of amino silane modified low molecular weight polyisoprene) was sufficiently active to start the polymerization reaction of isoprene. The structure of the moieties at the "alpha position" of alpha-modified/omega-modified linear macromolecular compounds, or at the polymer arm ends of the alpha-modified/branched modified macromolecular compounds, is derived from the structure of the amino silane initiator compound(s) and corresponds to Formula 1 of the invention.

In order to demonstrate the formation of moieties at the polymer chain end derived from the amino silane polymerization initiator of the present invention, modified low molecular weight polyisoprene was made as an example. As product, an amino silane end-modified polyisoprene was primarily formed, which is converted into a silanol chain end-modified polyisoprene upon hydrolytic removal of the dihydrocarbylamine protective group. In the case of the chain end-modifying compounds of Formula 6, the reaction of the living anionic polymer chain ends with chain end modifier alkoxy silyl groups led to polymer chain end-silicon modifier bonds. Upon hydrolysis, the trihydrocarbyl silyl, trihydrocarbyl stannyl, dihydrocarbyl silandiyl and dihydrocarbyl stannandiyl protective groups may partially or quantitatively be removed, forming polymers comprising thiol chain end groups.

One important application of the present invention is the production of vulcanized (elastomeric) polymer compositions having lower heat build up, lower "Tan δ at 60° C." values and lower DIN abrasion resistance values, while "Tan δ at 0° C." values and "Tan δ at -10° C." values are higher or at a similar level. If one of the three values, which relate to a tire rolling resistance or abrasion resistance, is improved, the other two values, which relate to the tire wet grip performance and tire ice grip performance, should not be negatively affected in order to improve the key tire performance properties. Tire treads made from polymer compositions having lower heat build up and lower "Tan δ at 60° C." values have corresponding lower rolling resistance, while those having lower DIN abrasion values have lower abrasion resistance, while those with higher "Tan δ at 0° C." values have corresponding better wet skid properties, while those with higher "Tan δ at -10° C." values have corresponding better ice grip properties.

The vulcanized elastomeric polymer compositions based on polymers made by using the initiator compounds of the invention (see example 9D in Tables 8 and 9) have relatively lower (or reduced) values for tan δ at 60° C.; relatively higher (or increased) values for tan δ at 0° C.; relatively higher (or increased) values for tan δ at -10° C.; relatively decreased tire heat built up and relatively decreased DIN abrasion, when compared with a vulcanized elastomeric polymer compositions based on other polymers (see examples 6D, 10 and 11D in Tables 8 and 9). Exemplary vulcanized composition 9D, which is based on modified polymer 9, modified with amino silane initiator I2a of the invention, formed from Li1 lithium amino silane polymerization initiator precursor and TMEDA in situ, has a heat built up value 109.2° C. and a tan δ value at 60° C. of 0.0792, while vulcanized composition 6D, which is based on non-modified polymer 6, formed from n-butyl lithium initiator I1, has a relatively higher heat built up value of 126.8° C. and a relatively higher tan δ value at 60° C. of 0.1286. Furthermore, exemplary comparative vulcanized compositions 10D and 11D, which are based on modified polymer 10 and 11, modified with amino silane initiator I8 and I9 of the invention, formed from amino silane polymerization initiator precursor Pr7, sec. butyl lithium and triethylamine and from silane polymerization initiator precursor Pr8, sec. butyl lithium and triethylamine, have relatively higher heat built up values of 127.7° C. and 122.8 as well as relatively lower tan δ values at 60° C. of 0.1266 and 0.1097 respectively, when compared with above stated values of vulcanized composition 9D.

It was found that the combination of the amino silane polymerization initiator compounds and chain end modifiers and optional coupling agents, each as described herein, forms modified polymer vulcanizates with excellent low hysteresis energy loss, as reflected by a low value of tan delta at 60° C.; improved abrasion resistance; and reduced vulcanizate heat built-up upon mechanical stress, while grip properties on a wet surface, as reflected by tan delta at 0° C., and grip properties on an icy surface, as reflected by tan delta at −10° C., are improved or in a similar range. Compared with a traditional polymer preparation, the processes of the present invention, combining A) amino silane polymerization initiator compounds with B) a sulfanylsilane chain end modifier compound and optionally C) coupling agents provide an increased degree of polymer modification and an improved performance in the corresponding polymer vulcanizate.

As shown in Tables 8 and 10, "heat built up" during dynamic deformation and DIN abrasion of the vulcanized polymer compositions comprising modified polymers of the invention is reduced, while "tan δ at 60° C." is decreased (Tables 9 and 11). Polymer "heat built-up" reduction is believed to improve the durability of the resulting vulcanized polymer composition, to reduce the vulcanizate hysteresis energy loss, leading to a decreased rolling resistance, and to increase overall elasticity. "Tensile Strength" and "Modulus 300" are not or not significantly deteriorated in comparison with the reference polymer, suggesting the formation of a stable polymer network with a higher resistance under mechanical stress. "Elongation at Break" values are very acceptable considering the degree of improvement of the tan δ, heat built up and abrasion resistance values.

The invention claimed is:

1. A modified macromolecular compound of the following Formula A:

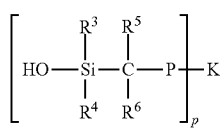

Formula A wherein
$R^3$ and $R^4$ are each independently selected from —OH, $(C_1\text{-}C_{18})$ alkyl, $(C_6\text{-}C_{18})$ aryl and $(C_7\text{-}C_{18})$ aralkyl;
$R^5$ and $R^6$ are each independently selected from hydrogen, $(C_1\text{-}C_{18})$ alkyl, $(C_6\text{-}C_{18})$ aryl and $(C_7\text{-}C_{18})$ aralkyl;
P is an elastomeric diene polymer chain comprising monomer units derived from at least one of the following monomers: butadiene, isoprene, styrene and alpha-methylstyrene; and
K represents a hydrogen atom or

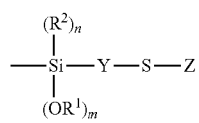

wherein
$R^1$ is independently selected from a hydrogen atom and $(C_1\text{-}C_4)$ alkyl;
$R^2$ is independently selected from (C1-C18) alkyl;
Y is at least divalent and is (C1-C18) alkyl, which may be substituted with one or more of the following groups: tertiary amine group, silyl group, (C7-C18) aralkyl group and $(C6\text{-}C_{18})$ aryl group; and
Z represents hydrogen or

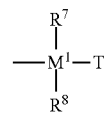

wherein
$M^1$ is a silicon atom or a tin atom; $R^7$ and $R^8$ are independently selected from $(C_1\text{-}C_{18})$ alkyl, $(C_6\text{-}C_{18})$ aryl and $(C_7\text{-}C_{18})$ aralkyl; and T represents $R^{11}$ or

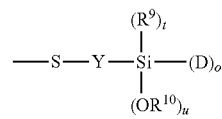

wherein
Y is as defined above;
$R^9$ is independently selected from $(C_1\text{-}C_{18})$ alkyl;
$R^{10}$ is independently selected from a hydrogen atom and $(C_1\text{-}C_4)$ alkyl;
$R^{11}$ is selected from (C1-C18) alkyl, (C6-C18) aryl and (C7-C18) aralkyl; and
D represents $OR^1$ or

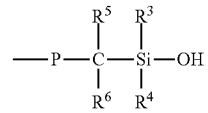

wherein
$R^1$, P, $R^3$, $R^4$, $R^5$ and $R^6$ are as defined above; and
p and o are each independently selected from an integer of 1, 2 and 3; m, n, t and u are each independently selected from an integer of 0, 1 and 2; and wherein p is 1 if K is H and otherwise p+m+n=3 and t+u+o=3.

2. The modified macromolecular compound according to claim 1, which has the following Formula 1:

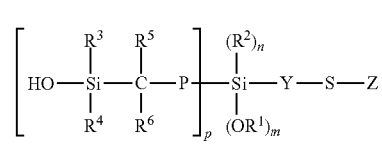

Formula 1 wherein $R^1$, $R^2$, $R^3$, $R^4$, $R^5$, $R^6$, Y, P and Z; and n, m and p are as defined in claim 1.

3. The modified macromolecular compound according to claim 2, wherein $R^3$ is selected from —OH and $(C_1\text{-}C_{18})$ alkyl; Z is represented by —$M^1(R^7)(R^8)(T)$; $M^1$ is a silicon atom or a tin atom; $R^7$ and $R^8$ are each independently selected from $(C_1\text{-}C_{18})$ alkyl; and T is represented by

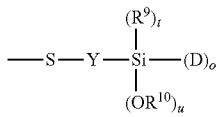

wherein Y, $R^9$, $R^{10}$ and D, and t, u and o are as defined in claim 1.

4. The modified macromolecular compound according to claim 2, wherein $R^3$ is selected from —OH and $(C_1\text{-}C_{18})$ alkyl; Z is represented by —$M^1(R^7)(R^8)(T)$; $M^1$ is a silicon atom or a tin atom; $R^7$ and $R^8$ are each independently selected from $(C_1\text{-}C_{18})$ alkyl; and T is represented by $R^{11}$, wherein $R^{11}$ is selected from $(C_1\text{-}C_{18})$ alkyl.

5. The modified macromolecular compound according to claim 1, wherein $M^1$ is a silicon atom.

6. The modified macromolecular compound according to claim 1, wherein $M^1$ is a tin atom.

7. The modified macromolecular compound according to claim 1, wherein Y is divalent and is $(C_1\text{-}C_{18})$ alkyl.

8. The modified macromolecular compound according to claim 1, wherein $R^3$ and $R^4$ are each independently selected from —OH and $(C_1\text{-}C_{18})$ alkyl; $R^5$ and $R^6$ are each independently selected from hydrogen and $(C_1\text{-}C_{18})$ alkyl; and $R^7$ and $R^8$ are each independently selected from $(C_1\text{-}C_{18})$ alkyl.

9. The modified macromolecular compound according to claim 8, wherein $R^3$, $R^4$, $R^7$ and $R^8$ are each independently selected from $(C_1\text{-}C_{18})$ alkyl; and $R^5$ and $R^6$ are each independently selected from hydrogen and $(C_1\text{-}C_{18})$ alkyl.

10. The modified macromolecular compound according to claim 1, wherein p and o are each independently selected from an integer of 1 and 2; m and u are each independently selected from an integer of 2 and 3; and n and t are each independently selected from and integer of 0 and 1.

11. A method of making the modified macromolecular compound as defined in claims 1, comprising the steps of:

(i) polymerizing in solution at least one elastomeric diene monomer with at least one amino silane polymerization initiator compound of Formula 4 or Formula 5

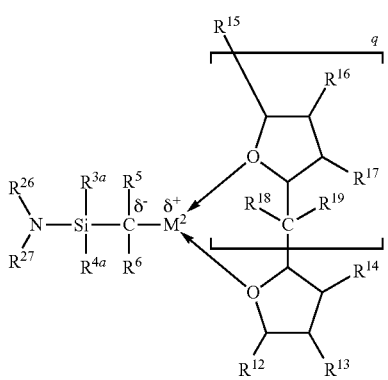

Formula 4

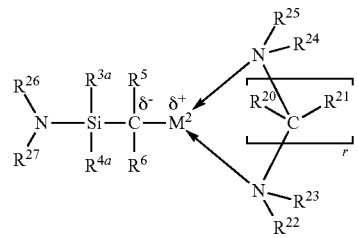

Formula 5 or Lewis base adducts thereof, wherein
$R^{3a}$ is independently selected from —$N(R^{28})R^{29}$, $(C_1\text{-}C_{18})$ alkyl, $(C_6\text{-}C_{18})$ aryl and $(C_7\text{-}C_{18})$ aralkyl;
$R^{4a}$ is independently selected from —$N(R^{30})R^{31}$, $(C_1\text{-}C_{18})$ alkyl, $(C_6\text{-}C_{18})$ aryl and $(C_7\text{-}C_{18})$ aralkyl;
$R^5$ and $R^6$ are as defined in claim 1;
$M^2$ is lithium, sodium or potassium;
$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ are each independently selected from hydrogen, $(C_1\text{-}C_{18})$ alkyl, $(C_6\text{-}C_{18})$ aryl and $(C_7\text{-}C_{18})$ aralkyl;
$R^{26}$, $R^{27}$, $R^{28}$, $R^{29}$, $R^{30}$ and $R^{31}$ are each independently selected from $(C_1\text{-}C_{18})$ alkyl, $(C_6\text{-}C_{18})$ aryl and $(C_7\text{-}C_{18})$ aralkyl;
q is selected from an integer of 1, 2, 3, 4 and 5; and
r is selected from an integer of 1, 2 and 3;

(ii) optionally reacting the polymer resulting from step (i) in solution with a chain end-modifying compound of Formula 6

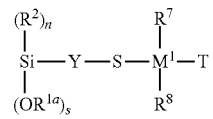

Formula 6 wherein
$R^{1a}$ is independently selected from $(C_1\text{-}C_4)$ alkyl;
$R^2$ is independently selected from $(C_1\text{-}C_{18})$ alkyl;
$R^7$ and $R^8$ are independently selected from $(C_1\text{-}C_{18})$ alkyl, $(C_6\text{-}C_{18})$ aryl and $(C_7\text{-}C_{18})$ aralkyl;
Y is at least divalent and is $(C_1\text{-}C_{18})$ alkyl, which may be substituted with one or more of the following groups: tertiary amine group, silyl group, $(C_7\text{-}C_{18})$ aralkyl group and $(C_6\text{-}C_{18})$ aryl group; $R^2$, $R^7$, $R^8$ and n are as defined above;
$M^1$ is a silicon atom or a tin atom;
n is an integer selected from 0, 1 and 2; s is an integer selected from 1, 2 and 3; and n+s=3; and
T represents $R^{11}$ or

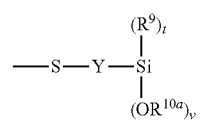

wherein
Y is as defined above;
$R^9$ is independently selected from $(C_1\text{-}C_{18})$ alkyl;
$R^{10a}$ is independently selected from $(C_1\text{-}C_4)$ alkyl;

t is an integer selected from 0, 1 and 2; v is an integer selected from 1, 2 and 3; and t+v=3; and contacting the polymer resulting from step (i) or (ii) with water.

12. The method according to claim 11, further comprising the following step for making the amino silane polymerization initiator compound of Formula 4 or Formula 5:

(ia) reacting a compound of the following Formula 9

Formula 9

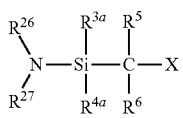

wherein

X is a chlorine atom, a bromine atom or a iodine atom; and $R^{3a}$, $R^{4a}$, $R^5$, $R^6$, $R^{26}$ and $R^{27}$ are as defined in claim 11;

an alkali metal selected from lithium, sodium and potassium; and a compound selected from Formula 10 and Formula 11

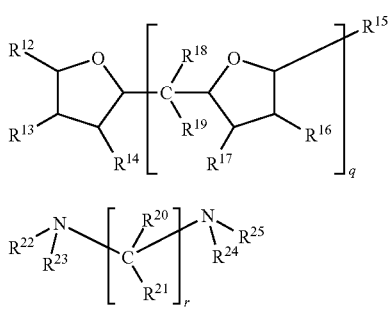

Formula 10

Formula 11 wherein $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$, q and r are as defined in claim 11.

13. The method according to claim 11, wherein the chain end-modifying compound used in step (ii) has the following Formula 7

Formula 7

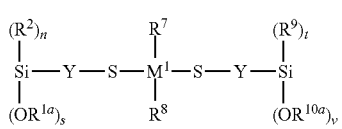

wherein $M^1$, Y, $R^{1a}$, $R^2$, n and s are as generally defined for Formula 6;

$R^7$, $R^8$ and $R^9$ are each independently selected from $(C_1-C_{18})$ alkyl;

$R^{10a}$ is independently selected from $(C_1-C_4)$ alkyl;

t is selected from an integer of 0, 1 and 2; v is selected from an integer of 1, 2 and 3; and t+v=3.

14. The method according to claim 13, wherein $M^2$ is lithium.

15. The method according to claim 13, wherein $R^{3a}$ is selected from $—N(R^{28})R^{29}$ and $(C_1-C_{18})$ alkyl, wherein $R^{28}$ and $R^{29}$ are each independently selected from $(C_1-C_{18})$ alkyl, $(C_6-C_{18})$ aryl and $(C_7-C_{18})$ aralkyl.

16. The method according to claim 13, wherein $R^{3a}$, $R^{4a}$, $R^{22}$, $R^{23}$, $R^{24}$, $R^{25}$, $R^{26}$ and $R^{27}$ are each independently selected from $(C_1-C_{18})$ alkyl and $R^5$, $R^6$, $R^{18}$, $R^{19}$, $R^{20}$ and $R^{21}$ are each independently selected from hydrogen and $(C_1-C_{18})$ alkyl and $R^{12}$, $R^{13}$, $R^{14}$, $R^{15}$, $R^{16}$ and $R^{17}$ are each independently selected from hydrogen and $(C_1-C_6)$ alkyl.

17. The method according to claim 13, wherein Y is divalent and is $(C_1-C_{18})$ alkyl.

18. The method according to claim 13, wherein q is 1 and r is 2.

19. The method according to claim 13, wherein s and v are each independently selected from an integer of 2 and 3; and n and t are each independently selected from an integer of 0 and 1.

20. A polymer composition comprising at least one modified macromolecular compound as defined in claim 1 and one or more further components selected from components which are added to or formed as a result of the polymerization process used for making the modified macromolecular compound and components which remain after solvent removal from the polymerization process.

21. The polymer composition according to claim 20, further comprising an oil.

22. The polymer composition according to claim 20 further comprising at least one filler.

23. The polymer composition according to claim 22, wherein the filler is one or more selected from carbon black, silica, carbon-silica dual-phase-filler, clay, calcium carbonate, magnesium carbonate, lignin, and glass particles.

24. The polymer composition according to claim 23, wherein the filler comprises silica.

25. The polymer composition according to claim 20 further comprising a vulcanization agent.

26. The polymer composition according to claim 20, further comprising at least one polymer selected from the group consisting of polybutadiene, butadiene-styrene copolymers, butadiene-isoprene copolymers, polyisoprene and butadiene-styrene-isoprene terpolymers.

27. A vulcanized polymer composition comprising the reaction product of at least the following:

1) at least one vulcanization agent; and 2) the polymer composition as defined in claim 20.

28. A method for making a vulcanized polymer composition comprising reacting at least the following components:

1) at least one vulcanization agent; and 2) the polymer composition as defined in claim 20.

29. An article comprising at least one component formed from the vulcanized polymer composition as defined in claim 27.

30. The article according to claim 29, which is selected from the group consisting of a tire, a tire tread, a tire side wall, a tire carcass, a belt, a hose, a vibration damper, and a footwear component.

31. An amino silane polymerization initiator compound of the following Formula 4 or Formula 5:

Formula 4

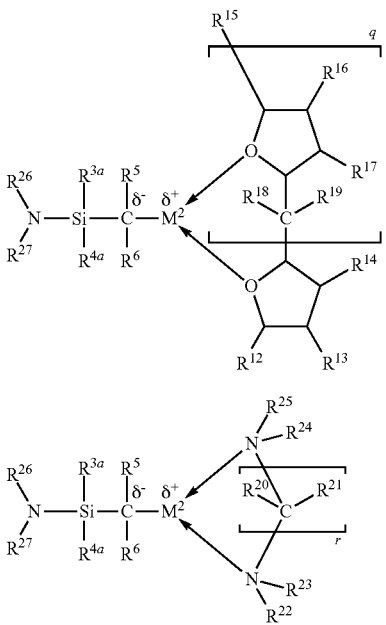

Formula 5

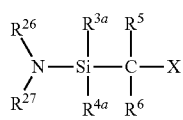

or Lewis base adducts thereof, wherein
$R^{3a}$ is independently selected from $-N(R^{28})R^{29}$, $(C_1$-$C_{18})$ alkyl, $(C_6$-$C_{18})$ aryl and $(C_7$-$C_{18})$ aralkyl;
$R^{4a}$ is independently selected from $-N(R^{30})R^{31}$, $(C_1$-$C_{18})$ alkyl, $(C_6$-$C_{18})$ aryl and $(C_7$-$C_{18})$ aralkyl;
$R^5$ and $R^6$ are as defined in claim 1;
$M^2$ is lithium, sodium or potassium;
$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$, are each independently selected from hydrogen, $(C_1$-$C_{18})$ alkyl, $(C_6$-$C_{18})$ aryl and $(C_7$-$C_{18})$ aralkyl;
$R^{26}$, $R^{27}$, $R^{28}$, $R^{29}$, $R^{30}$ and $R^{31}$ are each independently selected from $(C_1$-$C_{18})$ alkyl, $(C_6$-$C_{18})$ aryl and $(C_7$-$C_{18})$ aralkyl;
q is selected from an integer of 1, 2, 3, 4 and 5; and
r is selected from an integer of 1, 2 and 3.

32. A method of making the amino silane polymerization initiator of Formula 4 or Formula 5 as defined in claim 31, said method comprising the step of
reacting a compound of the following Formula 9

Formula 9

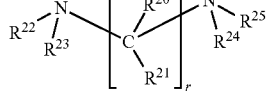

wherein
X is a chlorine atom, a bromine atom or a iodine atom; and
$R^{3a}$, $R^{4a}$, $R^5$, $R^6$, $R^{26}$ and $R^{27}$ are as defined in claim 31;
an alkali metal selected from lithium, sodium and potassium; and
a compound selected from the following Formula 10 and the following Formula 11

Formula 10

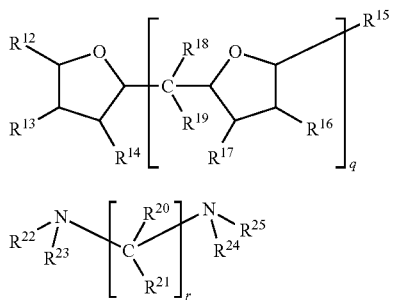

Formula 11 wherein
$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$, q and r are as defined in claim 31.

33. The amino silane polymerization initiator compound according to claim 31, wherein
X is a chlorine or bromine atom;
$R^{3a}$ is selected from $-N(R^{28})R^{29}$ and $(C_1$-$C_{18})$ alkyl;
$R^{4a}$ is selected from $-N(R^{30})R^{31}$ and $(C_1$-$C_{18})$ alkyl;
$R^5$ and $R^6$ are each independently selected from hydrogen and $(C_1$-$C_{18})$ alkyl;
$R^{12}$, $R^{13}$, $R^{14}$, $R^{15}$, $R^{16}$ and $R^{17}$ are each independently selected from hydrogen and $(C_1$-$C_6)$ alkyl;
$R^{18}$, $R^{19}$, $R^{20}$ and $R^{21}$ are each independently selected from hydrogen and $(C_1$-$C_{18})$ alkyl;
$R^{22}$, $R^{23}$, R24 and $R^{25}$ are each independently selected from $(C_1$-$C_{18})$ alkyl;
$R^{26}$, $R^{27}$, $R^{28}$, $R^{29}$, $R^{30}$ and $R^{31}$ are each independently selected from $(C_1$-$C_{18})$ alkyl; and
q is 1 and r is 2.

34. The amino silane polymerization initiator compound according to claim 33, wherein
X is a chlorine or bromine atom;
$R^{3a}$ is selected from $-N(R^{28})R^{29}$ and $(C_1$-$C_{18})$ alkyl;
$R^{4a}$ is selected from $(C_1$-$C_{18})$ alkyl;
$R^5$ and $R^6$ are each independently selected from hydrogen and $(C_1$-$C_{18})$ alkyl;
$R^{12}$, $R^{13}$, $R^{14}$, $R^{15}$, $R^{16}$, and $R^{17}$, are each independently selected from hydrogen and $(C_1$-$C_6)$ alkyl;
$R^{18}$, $R^{19}$, $R^{20}$ and $R^{21}$ are each independently selected from hydrogen and $(C_1$-$C_{18})$ alkyl;
$R^{22}$, $R^{23}$, $R^{24}$ and $R^{25}$ are each independently selected from $(C_1$-$C_{18})$ alkyl;
$R^{26}$, $R^{27}$, $R^{28}$ and $R^{29}$ are each independently selected from $(C_1$-$C_{18})$ alkyl; and
q is 1 and r is 2.

35. The amino silane polymerization initiator compound according to claim 34, wherein
X is a chlorine atom;
$R^{3a}$ and $R^{4a}$ are selected from $(C_1$-$C_{18})$ alkyl;
$R^5$ and $R^6$ are each independently selected from hydrogen and $(C_1$-$C_{18})$ alkyl;
$R^{12}$, $R^{13}$, $R^{14}$, $R^{15}$, $R^{16}$, $R^{17}$, $R^{18}$, $R^{19}$, $R^{20}$, and $R^{21}$, a are each independently selected from hydrogen and $(C_1$-$C_4)$ alkyl;
$R^{22}$, $R^{23}$, $R^{24}$ and $R^{25}$ are each independently selected from $(C_1$-$C_4)$ alkyl;
$R^{26}$ and $R^{27}$ are each independently selected from $(C_1$-$C_{18})$ alkyl;
q is 1 and r is 2; and
the alkali metal is lithium.

* * * * *